(12) United States Patent
Ruohola-Baker et al.

(10) Patent No.: US 9,624,471 B2
(45) Date of Patent: Apr. 18, 2017

(54) METHODS FOR MATURING CARDIOMYOCYTES AND USES THEREOF

(71) Applicant: UNIVERSITY OF WASHINGTON THROUGH ITS CENTER FOR COMMERCIALIZATION, Seattle, WA (US)

(72) Inventors: Hannele Ruohola-Baker, Seattle, WA (US); Kavitha Kuppusamy, Seattle, WA (US); Henrik Sperber, Seattle, WA (US)

(73) Assignee: UNIVERSITY OF WASHINGTON THROUGH ITS CENTER FOR COMMERCIALIZATION, Seattle, WA (US)

(*) Notice: Subject to any disclaimer, the term of this patent is extended or adjusted under 35 U.S.C. 154(b) by 0 days.

(21) Appl. No.: 14/897,403

(22) PCT Filed: Jun. 12, 2014

(86) PCT No.: PCT/US2014/042132
§ 371 (c)(1),
(2) Date: Dec. 10, 2015

(87) PCT Pub. No.: WO2014/201254
PCT Pub. Date: Dec. 18, 2014

(65) Prior Publication Data
US 2016/0130555 A1    May 12, 2016

Related U.S. Application Data

(60) Provisional application No. 61/834,349, filed on Jun. 12, 2013, provisional application No. 62/010,807, filed on Jun. 11, 2014.

(51) Int. Cl.
| | | |
|---|---|---|
| *C12N 5/16* | (2006.01) | |
| *C12N 5/22* | (2006.01) | |
| *C12N 15/06* | (2006.01) | |
| *C12N 15/07* | (2006.01) | |
| *C12N 15/113* | (2010.01) | |
| *A61K 35/44* | (2015.01) | |
| *A61K 48/00* | (2006.01) | |
| *C12N 5/077* | (2010.01) | |
| *C12N 15/11* | (2006.01) | |
| *A61K 35/34* | (2015.01) | |

(52) U.S. Cl.
CPC ............ *C12N 5/0657* (2013.01); *A61K 35/34* (2013.01); *C12N 15/111* (2013.01); *C12N 15/113* (2013.01); *C12N 2310/141* (2013.01); *C12N 2320/30* (2013.01)

(58) Field of Classification Search
None
See application file for complete search history.

(56) References Cited

U.S. PATENT DOCUMENTS

| | | | |
|---|---|---|---|
| 1,995,970 | A | 3/1935 | Lowrance |
| 2,676,945 | A | 4/1954 | Higgins |
| 2,683,136 | A | 7/1954 | Higgins |
| 2,703,316 | A | 3/1955 | Schneider |
| 2,758,987 | A | 8/1956 | Salzberg |
| 2,951,828 | A | 9/1960 | Karl et al. |
| 3,531,561 | A | 9/1970 | Trehu |
| 5,843,780 | A | 12/1998 | Thomson |
| 5,945,577 | A | 8/1999 | Stice et al. |
| 5,994,619 | A | 11/1999 | Stice et al. |
| 6,200,806 | B1 | 3/2001 | Thomson |
| 6,235,970 | B1 | 5/2001 | Stice et al. |
| 7,396,537 | B1 | 7/2008 | Krupnick et al. |
| 8,283,331 | B2 | 10/2012 | Gregory et al. |
| 9,220,721 | B2 * | 12/2015 | Aguirre .............. A61K 31/7088 |
| 2003/0022367 | A1 | 1/2003 | Xu |
| 2004/0017712 | A1 | 1/2004 | Hoffmann et al. |
| 2006/0153815 | A1 | 7/2006 | Seyda et al. |
| 2006/0246491 | A1 | 11/2006 | Srivastava |
| 2009/0317369 | A1 | 12/2009 | Hosoda et al. |
| 2010/0184051 | A1 | 7/2010 | Hochedlinger et al. |
| 2010/0292297 | A1 | 11/2010 | Wang et al. |

(Continued)

FOREIGN PATENT DOCUMENTS

| | | |
|---|---|---|
| WO | 2005/003300 A2 | 1/2005 |
| WO | 2010/120969 A1 | 10/2010 |

(Continued)

OTHER PUBLICATIONS

Newman et al (RNA (2008), 14:1539-1549).*
Cao et al (International Journal of Molecular Medicine 30: 1095-1104, 2012).*
Colas et al (Genes & Development 26:2567-2579, 2012).*
Posterino et al (J Appl Physiol 111: 236-243, 2011).*
Yang et al (Circ Res. 2011;108:305-313).*
Mdaki et al (PLoS One. 2016; 11(2): e0149002, 16 pages).*
Zhang et al (J Mol Cell Cardiol 33, 907-921 (2001)).*

(Continued)

*Primary Examiner* — Richard Schnizer
(74) *Attorney, Agent, or Firm* — Nixon Peabody LLP; Mark J. FitzGerald; Teresa A. Ptashka

(57) ABSTRACT

Described herein are methods and compositions useful for inducing maturation of a cardiomyocyte to a mature (e.g., adult) phenotype, such that the function and morphology of the mature cardiomyocyte matches or more closely mimics that of the adult heart. The methods and compositions use Let-7 miRNAs and modified forms thereof. Such methods and compositions permit the study and treatment of adult-onset cardiac diseases, disorders or injuries with mature cardiomyocytes that mimic the heart function of an adult. Methods of using cardiomyocytes matured in this manner for drug identification and drug cardiotoxicity testing are also provided.

9 Claims, 43 Drawing Sheets

(56) References Cited

U.S. PATENT DOCUMENTS

| | | |
|---|---|---|
| 2010/0298407 A1 | 11/2010 | Mendell et al. |
| 2011/0172295 A1 | 7/2011 | Hammond et al. |
| 2012/0134966 A1 | 5/2012 | Blelloch et al. |
| 2013/0029866 A1 | 1/2013 | Sun et al. |
| 2015/0148405 A1* | 5/2015 | Meffert ............... C12N 15/113 514/44 R |

FOREIGN PATENT DOCUMENTS

| | | |
|---|---|---|
| WO | 2013/057527 A2 | 4/2013 |
| WO | 2013/071079 A1 | 5/2013 |
| WO | 2013/126605 A1 | 8/2013 |
| WO | 2013/163296 A1 | 10/2013 |
| WO | 2014/100252 A1 | 6/2014 |

OTHER PUBLICATIONS

Mayr et al (Nucleic Acids Research, 2012, 40(15): 7492-7506).*
Gan et al., "MicroRNA Profiling during Cardiomyocyte-Specific Differentiation of Murine Embryonic Stem Cells Based on Two Different miRNA Array Platforms", PLoS ONE 6(10):e25809 (2011).
Kim et al., "Studying arrhythmogenic right ventricular dysplasia with patient-specific iPSCs", Nature 494(7435):105-110 (2013).
Laflamme et al., "Cardiomyocytes derived from human embryonic stem cells in pro-survival factors enhance function of infarcted rat hearts", Nature Biotechnology 25(9):1015-1024 (2007).
Laflamme et al., "Heart Regeneration", Nature 473(7347):326-335 (2011).
Lian et al., "Robust cardiomyocyte differentiation from human pluripotent stem cells via temporal modulation of canonical Wnt signaling", PNAS 109(27):E1848-E1857 (2012).
Liang et al., "Drug Screening Using a Library of Human Induced Pluripotent Stem Cell-Derived Cardiomyocytes Reveals Disease-Specific Patterns of Cardiotoxicity", Circulation 127(16):1677-1691 (2013).
Lundy et al., "Structural and Functional Maturation of Cardiomyocytes Derived from Human Pluripotent Stem Cells", Stem Cells and Development 22(14):1991-2002 (2013).
Paige et al., "A Temporal Chromatin Signature in Human Embryonic Stem Cells Identifies Regulators of Cardiac Development", Cell 151(1):221-232(2012).
Paige et al., "Endogenous Wnt/beta-Catenin Signaling is Required for Cardiac Differentiation in Human Embryonic Stem Cells", PLoS ONE 5(6):e11134 (2010).
Palpant et al., "Inhibition of β-catenin signaling respecifies anterior-like endothelium into beating human cardiomyocytes", Development 142(18):3198-3209 (2015).
Robertson et al., "Concise Review: Maturation Phases of Human Pluripotent Stem Cell-Derived Cardiomyocytes" Stem Cells 31(5):829-837 (2013).
Tulloch et al., "Growth of Engineered Human Myocardium with Mechanical Loading and Vascular Coculture", Circ Res. 109(1):47-59 (2011).
Wilson et al., "Dynamic MicroRNA Expression Programs During Cardiac Differentiation of Human Embryonic Stem Cells: Role for miR-499", Circ Cardiovasc Genet. 3(5):426-435 (2010).
Yang et al., "Engineering Adolescence: Maturation of Human Pluripotent Stem Cell-Derived Cardiomyocytes" Circ Res. 114(3):511-523 (2014).
Zhu et al., "The Lin28/let-7 axis regulates glucose metabolism", Cell 147(1):81-94 (2011).
Ahuja et al., "Cardiac Myocyte Cell Cycle Control in Development, Disease and Regeneration", Physiol Rev. 87 (2):521-544 (2007).
Anders et al., "Differential expression analysis for sequence count data", Genome Biology 11:R106 (2010).
Beqqali et al., "Genome-Wide Transcriptional Profiling of Human Embryonic Stem Cells Differentiating to Cardiomyocytes", Stem Cells 24:1956-1967 (2006).

Brodsky et al., "Variability of the cardiomyocyte ploidy in normal human hearts", Virchows Archiv B Cell Pathol 61:289-294 (1991).
Bullard et al., "Evaluation of statistical methods for normalization and differential expression in mRNA-Seq experiments", BMC Bioinformatics 11:94 (2010).
Burridge et al., "Production of De Novo Cardiomyocytes: Human Pluripotent Stem Cell Differentiation and Direct Reprogramming", Cell Stem Cell 10(1):16-28 (2012).
Cao et al., "Transcriptional and Functional Profiling of Human Embryonic Stem Cell-Derived Cardiomyocytes", PLoS One 3(10):e3474 (2008).
Carley et al., "Fatty Acid (FFA) Transport in Cardiomyocytes Revealed by Imaging Unbound FFA Is Mediated by an FFA Pump Modulated by the CD36 Protein", The Journal of Biological Chemistry 286(6):4589-4597 (2011).
Chang et al., "Trim71 cooperates with microRNAs to repress Cdkn1a expression and promote embryonic stem cell proliferation", Nat Commun. 3:923 (2012).
Chong et al., "Progenitor Cells Identified by PDGFR-Alpha Expression in the Developing and Diseased Human Heart", Stem Cells and Development 22(13):1932-1943 (2013).
Davis et al., "Pluripotent stem cell models of cardiac disease and their implication for drug discovery and development", Trends in Molecular Medicine 17(9):475-484 (2011).
Debosch et al., "Insulin Signaling Pathways and Cardiac Growth", J Mol Cell Cardiol. 44(5):855-864 (2008).
Denzel et al., "T-cadherin is critical for adiponectin-mediated cardioprotection in mice", The Journal of Clinical Investigation 120(12):4342-4352 (2010).
Dobin et al., "STAR: ultrafast universal RNA-seq aligner", Bioinformatics 29(1):15-21 (2013).
Espinoza-Lewis et al., "MicroRNAs in Heart Development", Current Topics in Developmental Biology 100:279-317 (2012).
Fearnley et al., "Calcium Signaling in Cardiac Myocytes", Cold Spring Harb Perspect Biol 3:a004242 (2011).
Flicek et al., "Ensembl 2014", Nucleic Acids Research 42:D749-D755 (2014).
Foldes et al., "Modulation of human embryonic stem cell-derived cardiomyocyte growth: A testbed for studying human cardiac hypertrophy?", Journal of Molecular and Cellular Cardiology 50:367-376 (2011).
Gomes et al., "Cardiac Troponin T Isoforms Affect the Ca2 Sensitivity of Force Development in the Presence of Slow Skeletal Troponin I", The Journal of Biological Chemistry 279(48):49579-49587 (2004).
Huangfu et al., "Induction of pluripotent stem cells by defined factors is greatly improved by small-molecule compounds", Nature Biotechnology 26(7):795-797 (2008).
Jaenisch et al., "Stem cells, the molecular circuitry of pluripotency and nuclear reprogramming", Cell 132(4):567-582 (2008).
Kellogg, "Wee1-dependent mechanisms required for coordination of cell growth and cell division", Journal of Cell Science 116:4883-4890 (2003).
Kim et al., "Re-Expression of Fetal Troponin Isoforms in the Postinfarction Failing Heart of the Rat", Circ J. 66:959-964 (2002).
Kuppusamy et al., "MicroRNA Regulation and Role in Stem Cell Maintenance, Cardiac Differentiation and Hypertrophy", Curr Mol Med. 13(5):757-764 (2013).
La Torre et al., "Conserved microRNA pathway regulates developmental timing of retinal neurogenesis", PNAS 110(36):E2362-E2370 (2013).
Lopaschuk et al., "Energy Metabolic Phenotype of the Cardiomyocyte During Development, Differentiation, and Postnatal Maturation", J Cardiovasc Pharmacol 56(2):130-140 (2010).
Lopaschuk et al., "Myocardial Fatty Acid Metabolism in Health and Disease", Physiol Rev. 90:207-258 (2010).
Lowry et al., "The strength and genetic basis of reproductive isolating barriers in flowering plants", Phil. Trans. R. Soc. B 363:3009-3021 (2008).
Mackowiak, "Identification of Novel and Known miRNAs in Deep-Sequencing Data with miRDeep2", Current Protocols in Bioinformatics Chapter 12:Unit 12.10.2 (2011).

(56) References Cited

OTHER PUBLICATIONS

Maherali et al., "Guidelines and Techniques for the Generation of Induced Pluripotent Stem Cells", Cell Stem Cell 3(6):595-605 (2008).
Marson et al., "Wnt signaling promotes reprogramming of somatic cells to pluripotency", Cell Stem Cell 3(2):132-135 (2008).
McCall et al., "MicroRNA profiling of diverse endothelial cell types", BMC Medical Genomics 4:78 (2011).
McMahon et al., "Developmental expression of the putative transcription factor Egr-1 suggests that Egr-1 and c-fos are coregulated in some tissues", Development 108:281-287 (1990).
Mihic et al., "The effect of cyclic stretch on maturation and 3D tissue formation of human embryonic stem cell-derived cardiomyocytes", Biomaterials 35:2798-2808 (2014).
Nam et al., "Thr-1989 Phosphorylation Is a Marker of Active Ataxia Telangiectasia-mutated and Rad3-related (ATR) Kinase", The Journal of Biological Chemistry 286(33):28707-28714 (2011).
Nielsen et al., "Peptide Nucleic Acid (PNA). A DNA Mimic with a Peptide Backbone", Bioconjugate Chem. 5:3-7 (1994).
Olivetti et al., "Aging Cardiac Hypertrophy and Ischemic Cardiomyopathy Do Not Affect the Proportion of Mononucleated and Multinucleated Myocytes in the Human Heart", J Mol Cell Cardiol 28(7):1463-1477 (1996).
Opie, "Metabolism of the heart in health and disease: Part III", American Heart Journal 77(3):383-410 (1969).
Park et al., "Reprogramming of human somatic cells to pluripotency with defined factors", Nature 451(7175):141-146 (2008).
Roach et al., "Methods for the Isolation and Maintenance of Murine Embryonic Stem Cells", Methods in Molecular Biology 185:1-16 (2002).
Roberts et al., "Identification of novel transcripts in annotated genomes using RNA-seq", Bioinformatics 27(17):2325-2329 (2011).
Robinson et al., "edgeR: a Bioconductor package for differential expression analysis of digital gene expression data", BioInformatics 26(1):139-140 (2010).
Rodriguez et al., "Measuring the Contractile Forces of Human Induced Pluripotent Stem Cell-Derived Cardiomyocytes With Arrays of Microposts", Journal of Biomechanical Engineering 136:051005(1-10) (2014).
Saeed et al., "TM4: A Free, Open-Source System for Microarray Data Management and Analysis", BioTechniques 34:374-378 (2003).
Shi et al., "A Combined Chemical and Genetic Approach for the Generation of Induced Pluripotent Stem Cells", Cell Stem Cell 2(6):525-528 (2008).
Shi et al., "Induction of Pluripotent Stem Cells from Mouse Embryonic Fibroblasts by Oct4 and Klf4 with Small-Molecule Compounds", Cell Stem Cell 3:568-574 (2008).
Smith, "Embryo-Derived Stem Cells: Of Mice and Men", Annu. Rev. Cell. Dev. Biol. 17:435-462 (2001).
Sniadecki et al., "Microfabricated Silicone Elastomeric Post Arrays for Measuring Traction Forces of Adherent Cells", Methods in Cell Biology 83:313-328 (2007).
Snir et al., "Assessment of the ultrastructural and proliferative properties of human embryonic stem cell-derived cardiomyocytes", Am J Physiol Heart Circ Physiol 285:H2355-H2363 (2003).
Stirchak et al., "Uncharged stereoregular nucleic acid analogs: 2. Morpholino nucleoside oligomers with carbamate internucleoside linkages", Nucleic Acids Research 17(15):6129-6141 (1989).
Takahashi et al., "Induction of Pluripotent Stem Cells from Mouse Embryonic and Adult Fibroblast Cultures by Defined Factors", Cell 126:663-676 (2006).
Tan et al., "Cells lying on a bed of microneedles: An approach to isolate mechanical force", PNAS 100(4):1484-1489 (2003).
Thierry-Mieg et al., "AceView: a comprehensive cDNA-supported gene and transcripts annotation", Genome Biology 7(Suppl I):S12 (2006).
Trounson, "The derivation and potential use of human embryonic stem cells", Reprod. Fertil. Dev. 13:523-532 (2001).
Uhlmann et al., "Oligonucleotide Analogs Containing Dephospho-Internucleoside Linkages", Methods in Molecular Biology 20:355-389 (1993).
Van Der Vusse et al., "Cardiac fatty acid uptake and transport in health and disease", Cardiovascular Research 45:279-293 (2000).
Van Rooij et al., "A signature pattern of stress-responsive microRNAs that can evoke cardiac hypertrophy and heart failure", PNAS 103(48):18255-18260 (2006).
Wang et al., "Egr-1 negatively regulates expression of the sodium-calcium exchanger-1 in cardiomyocytes in vitro and in vivo", Cadiovascular Research 65:187-194 (2005).
Warren et al., "Highly Efficient Reprogramming to Pluripotency and Directed Differentiation of Human Cells with Synthetic Modified mRNA", Cell Stem Cell 7:618-630 (2010).
Woltjen et al., "piggyBac transposition reprograms fibroblasts to induced pluripotent stem cells", Nature 458(7239):766-770 (2009).
Worringer et al., "The let-7/LIN-41 Pathway Regulates Reprogramming to Human Induced Pluripotent Stem Cells by Controlling Expression of Prodifferentiation Genes", Cell Stem Cell 14:40-52 (2014).
Xu et al., "Global Expression Profile of Highly Enriched Cardiomyocytes Derived from Human Embryonic Stem Cells", Stem Cells 27:2163-2174 (2009).
Yu et al., "Induced Pluripotent Stem Cell Lines Derived from Human Somatic Cells", Science 318:1917 (2007).
Chung et al., "Mitochondrial oxidative metabolism is required for the cardiac differentiation of stem cells", Nat Clin Pract Cardiovasc Med., 4(Suppl 1):S60-S67 (2007).
Feng et al., "Drosha processing controls the specificity and efficiency of global microRNA expression", Biochemica et Biophysica Acta., 1809(11-12):700-707 (2011).
Nam et al., "Molecular Basis for Interaction of let-7 MicroRNAs with Lin28", Cell, 147(5):1080-1091 (2011).

\* cited by examiner

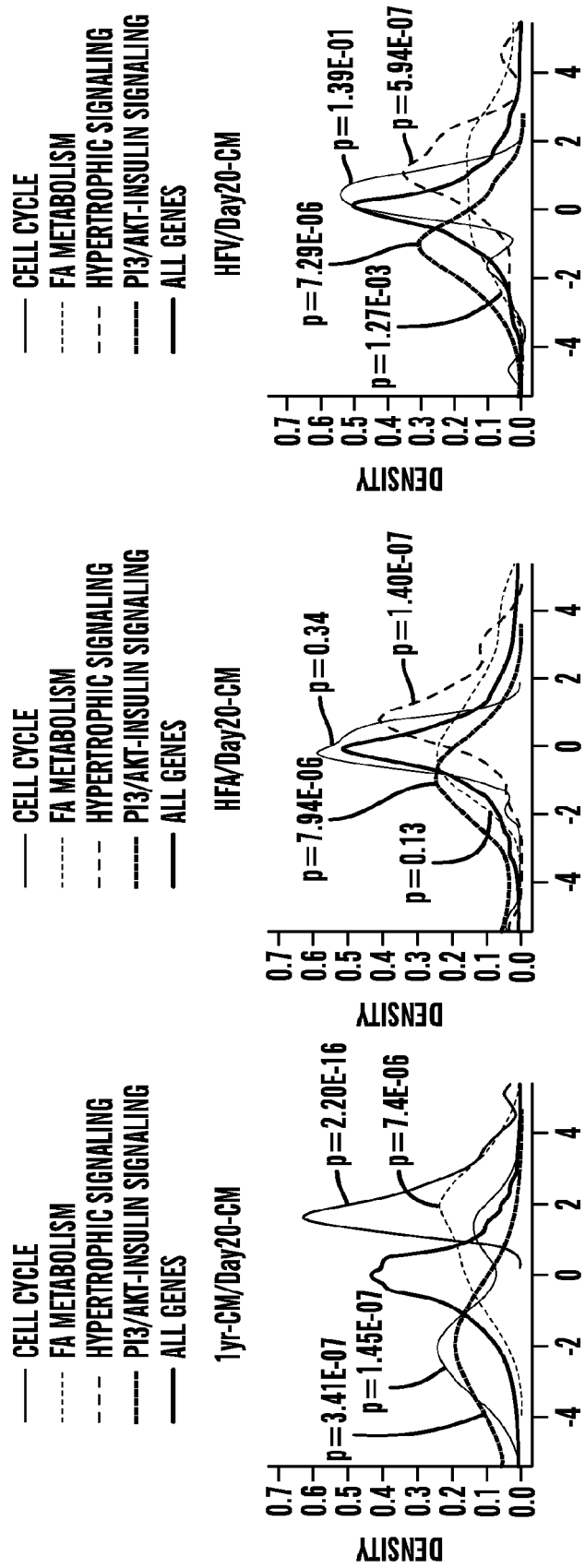

| miRNAs | NUMBER OF miRNA TARGETS IN 1yr-CM SEQ DATA SET |
|---|---|
| let-7 ↑ | 98 ↓ |
| mir-30b ↑ | 60 ↓ |
| mir-378 ↑ | 80 ↓ |
| mir-502 ↓ | 47 ↑ |
| mir-129 ↓ | 74 ↑ |

*FIG. 2C*

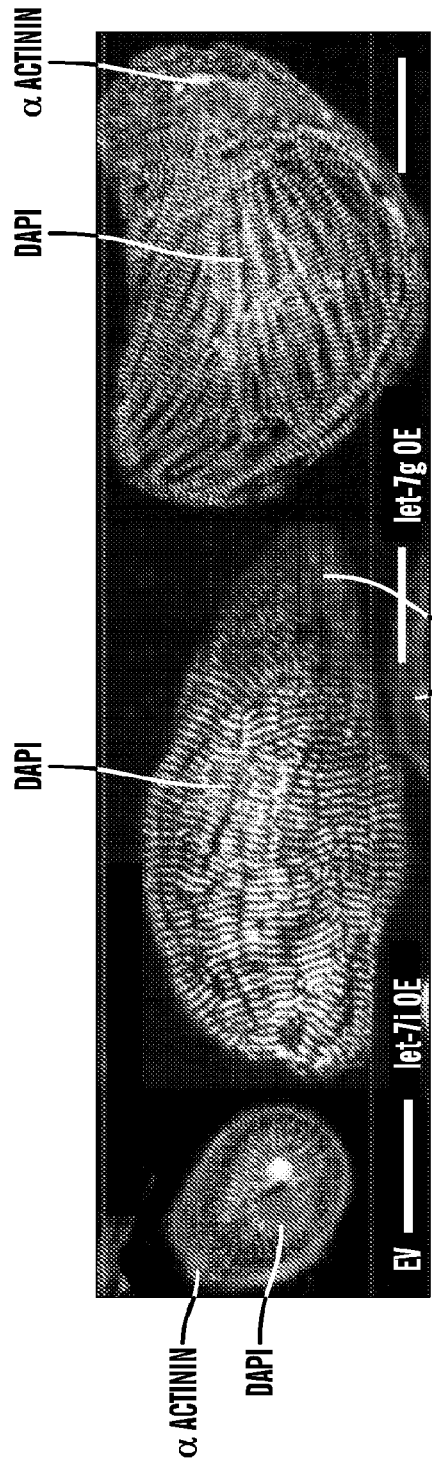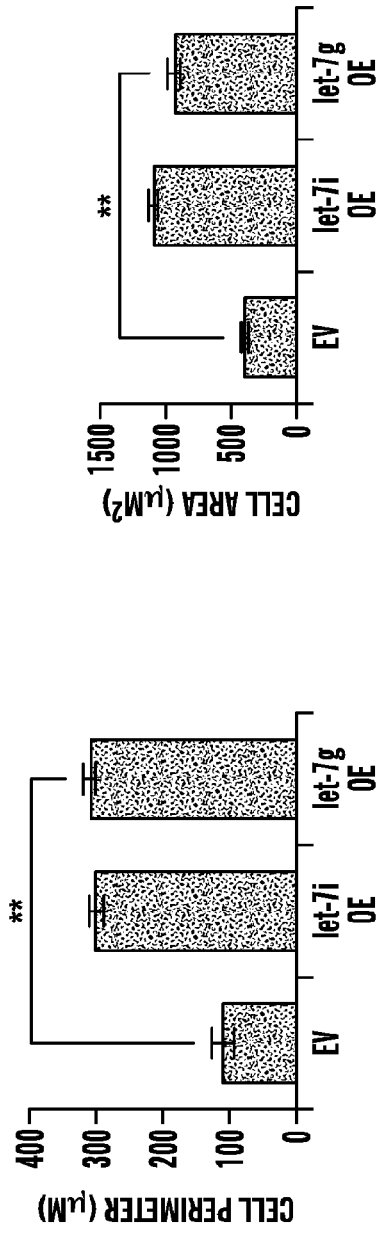
FIG. 3D
FIG. 3E
FIG. 3F

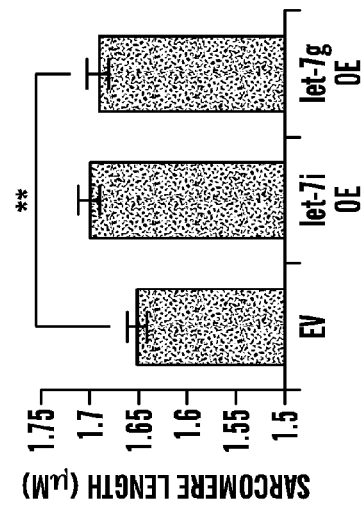
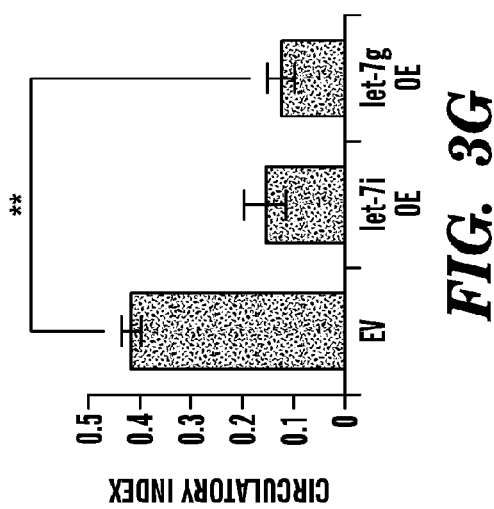
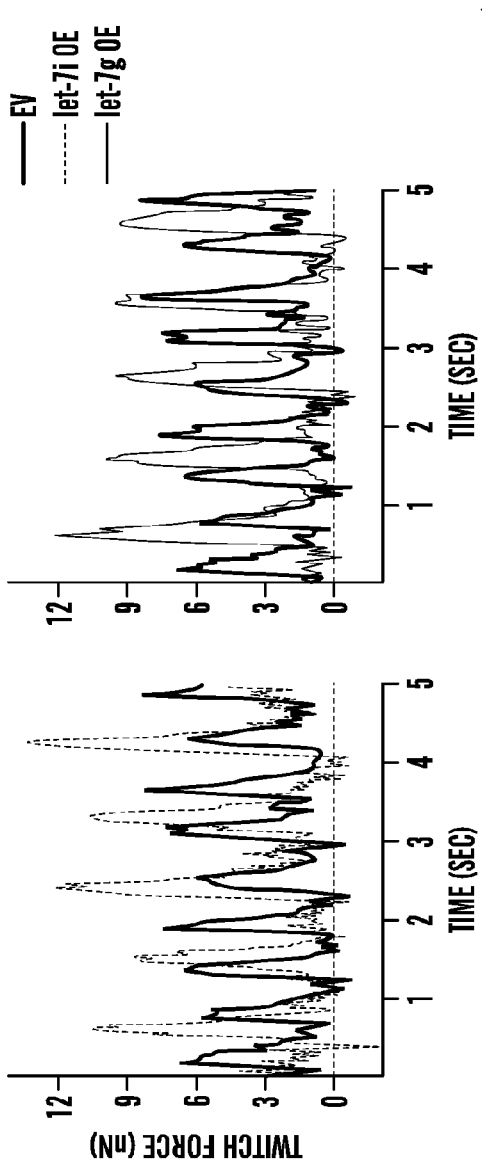

*p=2.76e-57

SEQUENCE LISTING

<160> NUMBER OF SEQ ID NOS: 23

<210> SEQ ID NO 1
<211> LENGTH: 80
<212> TYPE: RNA
<213> ORGANISM: Homo sapiens

<400> SEQUENCE: 1
ugggaugagg uaguagguug uauaguuuua ggucacacc caccacuggg agauaacuau        60
acaaucuacu gucuuuccua                                                  80

<210> SEQ ID NO 2
<211> LENGTH: 72
<212> TYPE: RNA
<213> ORGANISM: Homo sapiens

<400> SEQUENCE: 2
agguugaggu aguagguugu auaguuuaga auuacaucaa gggagauaac uguacagccu       60
ccuagcuuuc cu                                                          72

<210> SEQ ID NO 3
<211> LENGTH: 83
<212> TYPE: RNA
<213> ORGANISM: Homo sapiens

<400> SEQUENCE: 3
cggggugagg uaguagguug uguggquuuca gggcagugau guugcccuc ggaagauaac       60 uauacaaccu acugccuucc cug                                              83

<210> SEQ ID NO 4
<211> LENGTH: 84
<212> TYPE: RNA
<213> ORGANISM: Homo sapiens

<400> SEQUENCE: 4
gcauccgggu ugagguagua gguuguaugg uuuagaguua cacccuggga guuaacugua       60
caaccuucua gcuuuccuug gagc                                             84

<210> SEQ ID NO 5
<211> LENGTH: 87
<212> TYPE: RNA
<213> ORGANISM: Homo sapiens

<400> SEQUENCE: 5
ccuaggaaga gguaguaggu ugcauaguuu uagggcaggg auuuugccca caaggaggua       60
acuauacgac cugcugccuu ucuuagg                                          87

<210> SEQ ID NO 6
<211> LENGTH: 79
<212> TYPE: RNA
<213> ORGANISM: Homo sapiens

<400> SEQUENCE: 6
cccgggcuga gguaggaggu uguauaguug aggaggacac ccaaggagau cacuauacgg       60
ccuccuagcu uucccagg                                                    79

<210> SEQ ID NO 7
<211> LENGTH: 87
<212> TYPE: RNA
<213> ORGANISM: Homo sapiens

<400> SEQUENCE: 7
ucagagugag guaguagauu guauaguugu gggguaguga uuuuacccug uucaggagau    60
aacuauacaa ucuauugccu uccuga    87

<210> SEQ ID NO 8
<211> LENGTH: 83
<212> TYPE: RNA
<213> ORGANISM: Homo sapiens

<400> SEQUENCE: 8
ugugggauga gguaguagau uguauaguuu uagggucaua ccccaucuug gagauaacua    60
uacagucuac ugucuuuccc acg    83

<210> SEQ ID NO 9
<211> LENGTH: 84
<212> TYPE: RNA
<213> ORGANISM: Homo sapiens

<400> SEQUENCE: 9
aggcugaggu aguaguuugu acaguuugag ggucuaugau accacccggu acaggagaua    60
acuguacagg ccacugccuu gcca    84

<210> SEQ ID NO 10
<211> LENGTH: 84
<212> TYPE: RNA
<213> ORGANISM: Homo sapiens

<400> SEQUENCE: 10
cuggcugagg uaguaguuug ugcuguuggu cggguuguga cauugcccgc uguggagaua    60
acugcgcaag cuacugccuu gcua    84

<210> SEQ ID NO 11
<211> LENGTH: 22
<212> TYPE: DNA
<213> ORGANISM: Homo sapiens

<400> SEQUENCE: 11
aactatacaa cctactacct ca    22

<210> SEQ ID NO 12
<211> LENGTH: 84
<212> TYPE: RNA
<213> ORGANISM: Homo sapiens

<400> SEQUENCE: 12
aggcugaggu aguaguuugu acaguuugag ggucuaugau accacccggu acaucagaua    60
acuguacagg ccacugccuu gcca    84

<210> SEQ ID NO 13
<211> LENGTH: 84
<212> TYPE: RNA
<213> ORGANISM: Homo sapiens

<400> SEQUENCE: 13
aggcugaggu aguaguuugu acaguuugag ggcguaugau accacccggu acaggaugca    60
acuguacagg ccacugccuu gcca    84

<210> SEQ ID NO 14

```
<211> LENGTH: 84
<212> TYPE: RNA
<213> ORGANISM: Homo sapiens

<400> SEQUENCE: 14
aggcugaggu aguaguuugu acaguuugag ggucuaugau accacccggu acaugagaua      60
acuguacagg ccacugccuu gcca                                            84

<210> SEQ ID NO 15
<211> LENGTH: 84
<212> TYPE: RNA
<213> ORGANISM: Homo sapiens

<400> SEQUENCE: 15
aggcugaggu aguaguuugu acaguuugag ggucuaugau accacccggu acaggauaua      60
acuguacagg ccacugccuu gcca                                            84

<210> SEQ ID NO 16
<211> LENGTH: 84
<212> TYPE: RNA
<213> ORGANISM: Homo sapiens

<400> SEQUENCE: 16
aggcugaggu aguaguuugu acaguuugag ggucuaugau accacccggu acaucagaua      60
acuguacagg ccacugccuu gcca                                            84

<210> SEQ ID NO 17
<211> LENGTH: 84
<212> TYPE: RNA
<213> ORGANISM: Homo sapiens

<400> SEQUENCE: 17
aggcugaggu aguaguuugu acaguuugag ggcggaugau accacccggu acauggcgca      60
acuguacagg ccacugccuu gcca                                            84

<210> SEQ ID NO 18
<211> LENGTH: 84
<212> TYPE: RNA
<213> ORGANISM: Homo sapiens

<400> SEQUENCE: 18
aggcugaggu aguaguuugu acaguuugag ggcguaugau accacccggu acaggaugca      60
acuguacagg ccacugccuu gcca                                            84

<210> SEQ ID NO 19
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tccgcgtggt cccgt                                                      15

<210> SEQ ID NO 20
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 20
attgtcctcc gcggcgc                                                17

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
agagttcctc cagcgctcc                                              19

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ccccacttgg cagctggc                                               18

<210> SEQ ID NO 23
<211> LENGTH: 88
<212> TYPE: RNA
<213> ORGANISM: Homo sapiens

<400> SEQUENCE: 23
ccaggcugag guaguaguuu guacaguuug agggucuaug auaccacccg guacaggaga    60
uaacuguaca ggccacugcc uugccagg                                      88
```

US 9,624,471 B2

METHODS FOR MATURING CARDIOMYOCYTES AND USES THEREOF

CROSS-REFERENCE TO RELATED APPLICATION

This application is a 35 U.S.C. §371 National Phase Entry Application of International Application PCT/US2014/042132 filed on Jun. 12, 2014, which designates the US, and which claims benefit under 35 U.S.C. §119(e) of U.S. Provisional Application No. 61/834,349 filed Jun. 12, 2013 and U.S. Provisional Application No. 62/010,807 filed on Jun. 11, 2014, the contents of each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Mar. 24, 2015, is named 002806-068592_US_SL and is 15,118 bytes in size.

GOVERNMENT SUPPORT

This invention was made with government support under Grant Nos. 3R01GM083867-03S1 and R01GM097372, awarded by the National Institutes of Health. The government has certain rights in the invention.

FIELD OF THE INVENTION

The field of the invention relates to the maturation of cardiac myocytes and uses thereof.

BACKGROUND

Micro RNAs (miRNAs) are conserved among diverse organisms, and are involved in essential biological processes throughout the life span of an organism (Esquela-Kerscher and Slack, 2006). In particular, miRNAs have been implicated in regulating cell growth, and cell and tissue differentiation, cellular processes that are associated with development.

Let-7 miRNAs function as gene silencing molecules that regulate the expression of protein-coding genes that comprise a let-7 target sequence. Let-7 miRNAs function to repress the expression of genes at the posttranscriptional level.

Let-7 is itself regulated by post-transcriptional modifications, for example, by the pluripotency factor LIN28 or by c-MYC. For example, LIN28 expression is reciprocal to that of mature let-7 and LIN28 selectively binds the primary and precursor forms of let-7, thereby inhibiting the processing of pri-let-7 to form the hairpin precursor. The binding of LIN28 to let-7 is thought to be facilitated by an interaction between the conserved loop sequence of a primary let-7 family member and an RNA-binding domain of a LIN28 protein. In addition, let-7 miRNAs in mammals have also been shown to regulate LIN28, indicating that let-7 may reciprocally enhance its own level by repressing LIN28, its negative regulator.

Distinctive expression patterns of miRNA have been shown in the hearts of normal mice and mice that suffered from heart disease (van Rooij et al. (2006) Proc. Natl. Acad. ScL, Vol. 103(48):18255-18260). For example, specific miRNAs were differentially regulated in mice induced to have pathological hypertrophy, or in response to constitutive activation of calcineurin, a stress-inducible mediator of the hypertrophic response. Importantly, several of these microRNAs were also dysregulated in failing human hearts, suggesting they established a diagnostic molecular signature for cardiac pathogenesis.

SUMMARY

Described herein are methods and compositions useful for inducing maturation of a cardiomyocyte to a mature (e.g., adult) phenotype, such that the function and morphology of the mature cardiomyocyte matches or more closely mimics that of the adult heart. Such methods and compositions permit the study and treatment of adult-onset cardiac diseases, disorders or injuries with mature cardiomyocytes that mimic the heart function of an adult.

Provided herein, in one aspect, is a method for inducing maturation of a cardiomyocyte, the method comprising: contacting a cardiomyocyte with a microRNA (miRNA) from the let-7 family, thereby inducing maturation of the cardiomyocyte.

In one embodiment of this aspect and all other aspects described herein, the miRNA from the let-7 family is selected from the group consisting of: let-7a-1, let-7a-2, let-7b, let-7c, let-7d, let-7e, let-7f-1, let-7f-2, let-7g, and let-7i.

In another embodiment of this aspect and all other aspects described herein, the miRNA is let-7g, or let-7i.

In another embodiment of this aspect and all other aspects described herein, the miRNA from the let-7 family is resistant to inhibition by Lin28.

In another embodiment of this aspect and all other aspects described herein, the miRNA comprises a mutation that prevents interaction of the miRNA with Lin28.

In another embodiment of this aspect and all other aspects described herein, the cardiomyocyte comprises a fetal-like phenotype prior to contacting with the miRNA.

In another embodiment of this aspect and all other aspects described herein, the fetal-like phenotype comprises a reliance on glycolysis for energy production.

In another embodiment of this aspect and all other aspects described herein, the maturation of the cardiomyocyte comprises a shift to an adult-like phenotype.

In another embodiment of this aspect and all other aspects described herein, the adult-like phenotype comprises an increase in mitochondrial respiration for energy.

In another embodiment of this aspect and all other aspects described herein, the increase in mitochondrial respiration comprises an increase in fatty acid oxidation.

In another embodiment of this aspect and all other aspects described herein, the adult-like phenotype comprises an increase in sarcomere length, an increase in contractile force, an increase in gene expression patterns indicative of an adult-like phenotype, a reduction in beat frequency, or an increase in cell size relative to the cells prior to contacting with the miRNA.

In another embodiment of this aspect and all other aspects described herein, the gene expression patterns indicative of an adult-like phenotype comprise expression of at least one of: cardiac troponin (cTnT), myosin heavy chain-7 (MYH7), sacrcoendoplasmic reticulum ATPAse (SERCA2a), gap junction protein alpha 1/connexin 43 (GJA1), or ryanodine receptor 2 (RYR2).

In another embodiment of this aspect and all other aspects described herein, the cardiomyocyte is derived from an embryonic stem cell, a pluripotent stem cell, or an induced pluripotent stem cell (iPS cell).

In another embodiment of this aspect and all other aspects described herein, the method further comprises a step of administering the resulting mature cardiomyocyte to a subject in need thereof.

In another embodiment of this aspect and all other aspects described herein, the subject has cardiac tissue damage.

In another embodiment of this aspect and all other aspects described herein, the cardiac tissue damage is a result of an acute myocardial infarction, ischemia/reperfusion injury, autophagy, cardiomyopathy, dilated cardiomyopathy, heart failure, restenosis, apoptosis, or necrosis.

In another embodiment of this aspect and all other aspects described herein, the mature cardiomyocyte is autologous to the subject.

In another embodiment of this aspect and all other aspects described herein, the mature cardiomyocyte is heterologous to the subject.

In another embodiment of this aspect and all other aspects described herein, the method is performed in vitro or ex vivo.

In another embodiment of this aspect and all other aspects described herein, the method is performed in vivo.

Another aspect provided herein relates to a Lin28 resistant let-7 miRNA composition comprising: a let-7 miRNA comprising (i) at least one modification to render the miRNA resistant to Lin28 binding, and (ii) at least one modification to retain proper miRNA processing in a cell.

In one embodiment, a single modification renders the miRNA resistant to Lin28 binding and further retains proper miRNA processing in the cell.

Another aspect provided herein relates to a Lin28 resistant let-7 miRNA composition comprising: a let-7 miRNA comprising (i) a first modification to render the miRNA resistant to Lin28 binding, and (ii) a second modification to retain proper miRNA processing in a cell.

In one embodiment of this aspect and all other aspects described herein, the proper miRNA processing comprises cleavage by Drosha.

It is contemplated herein that such Lin28-resistant let-7 miRNA compositions can be used for additional applications beyond their use in maturing a cardiomyocyte as described herein. That is, the compositions described herein are not limited to their use in the preparation of cardiomyocytes comprising an adult-like phenotype but rather can be used in any situation where a Lin28-resistant let-7 miRNA would be useful or therapeutic as determined by one of ordinary skill in the art.

In another embodiment of this aspect and all other aspects described herein, the miRNA precursor undergoes enhanced miRNA processing in a cell.

In another embodiment of this aspect and all other aspects described herein, the modified miRNA comprises five or fewer mismatches in positions 5 and 9-12 from the Drosha cutting site of the miRNA. As a reference point, position 1 is assigned to the first nucleotide pair after the Drosha cutting site. The nucleotides that form the single-stranded overhang after Drosha processing are assigned negative positions (e.g., −1, −2, etc.). Positions are then assigned for each nucleotide pair in ascending order moving towards the Dicer cleavage site. The average hairpin can contain several mismatches, which occasionally contain more nucleotides in one strand than the other. In such cases, the shorter strand is used to assign the mismatch position, using the later position whenever an asymmetric mismatch is located between two positions. Each position where the nucleotides are bound to each other is assigned the score 0, while positions with at least one nucleotide mismatch are given the score 1.

In another embodiment of this aspect and all other aspects described herein, the modified miRNA comprises four or fewer mismatches in positions 5 and 9-12 from the Drosha cutting site of the miRNA.

In another embodiment of this aspect and all other aspects described herein, the modified miRNA comprises three or fewer mismatches in positions 5 and 9-12 from the Drosha cutting site of the miRNA.

In another embodiment of this aspect and all other aspects described herein, the modified miRNA comprises two or fewer mismatches in positions 5 and 9-12 from the Drosha cutting site of the miRNA.

In another embodiment of this aspect and all other aspects described herein, the modified miRNA comprises a single mismatch in positions 5 and 9-12 from the Drosha cutting site of the miRNA.

In another embodiment of this aspect and all other aspects described herein, the modified miRNA comprises no mismatches in positions 5 and 9-12 from the Drosha cutting site of the miRNA.

In some embodiments of this aspect and all other aspects described herein, the modified miRNA is modified to encode at least 1 mismatch (e.g., 2, 3, 4, or 5 mismatches) at nucleotide positions 5, 9, 10, 11 or 12 from the miRNA's Drosha cutting site.

In other embodiments of this aspect and all other aspects described herein, the modified miRNA is modified to remove at least 1 naturally-encoded mismatch (e.g., 2, 3, 4, or 5 naturally-encoded mismatches) at nucleotide positions 5, 9, 10, 11 or 12 from the miRNA's Drosha cutting site.

In another embodiment of this aspect and all other aspects described herein, the let-7 miRNA is selected from the group consisting of: let-7a-1, let-7a-2, let-7b, let-7c, let-7d, let-7e, let-7f-1, let-7f-2, let-7g, and let-7i.

In another embodiment of this aspect and all other aspects described herein, the modification to render the miRNA resistant to Lin28 binding comprises a modification of the miRNA sequence at a Lin28 binding site comprising the sequence GGAG.

In another embodiment of this aspect and all other aspects described herein, the modification comprises a mutation, an insertion or a deletion.

In another embodiment of this aspect and all other aspects described, herein, the miRNA sequence is a human sequence or a modified human sequence. Note that a modified human sequence does not encompass a human sequence modified such that it has the same sequence as a non-human mammalian miRNA sequence.

In another embodiment of this aspect and all other aspects described herein, the composition comprises a human sequence selected from the group consisting of:

>hsa-let-7a-1

(SEQ ID NO: 1)
UGGGAUGAGGUAGUAGGUUGUAUAGUUUUAGGGUCACACCCACCACUGGGAGAUAACUAUACAAUCUACUGUCUUUCCUA

>hsa-let-7a-2

(SEQ ID NO: 2)
AGGUUGAGGUAGUAGGUUGUAUAGUUUAGAAUUACAUCAAGGGAGAUAACUGUACAGCCUCCUAGCUUUCCU

-continued

>hsa-let-7b
(SEQ ID NO: 3)
CGGGGUGAGGUAGUAGGUUGUGUGGUUUCAGGGCAGUGAUGUUGCCCC
UCGGAAGAUAACUAUACAACCUACUGCCUUCCCUG >hsa-let-7c
(SEQ ID NO: 4)
GCAUCCGGGUUGAGGUAGUAGGUUGUAUGGUUUAGAGUUACACCCUGG
GAGUUAACUGUACAACCUUCUAGCUUUCCUUGGAGC >hsa-let-7d
(SEQ ID NO: 5)
CCUAGGAAGAGGUAGUAGGUUGCAUAGUUUUAGGGCAGGAUUUUGCC
CACAAGGAGGUAACUAUACGACCUGCUGCCUUUCUUAGG >hsa-let-7e
(SEQ ID NO: 6)
CCCGGGCUGAGGUAGGAGGUUGUAUAGUUGAGGAGGACACCCAAGGAGA
UCACUAUACGGCCUCCUAGCUUUCCCAGG >hsa-let-7f-1
(SEQ ID NO: 7)
UCAGAGUGAGGUAGUAGAUUGUAUAGUUGUGGGGUAGGUGAUUUUACCCU
GUUCAGGAGAUAACUAUACAAUCUAUUGCCUUCCCUGA >hsa-let-7f-2
(SEQ ID NO: 8)
UGUGGGAUGAGGUAGUAGAUUGUAUAGUUUUAGGGUCAUACCCCAUCUU
GGAGAUAACUAUACAGUCUACUGUCUUUCCCACG >hsa-let-7g
(SEQ ID NO: 9)
AGGCUGAGGUAGUAGUUUGUACAGUUUGAGGGUCUAUGAUACCACCCGG
UACAGGAGAUAACUGUACAGGCCACUGCCUUGCCA >hsa-let-7i
(SEQ ID NO: 10)
CUGGCUGAGGUAGUAGUUUGUGCUGUUGGUCGGGUUGUGACAUUGCCCG
CUGUGGAGAUAACUGCGCAAGCUACUGCCUUGCUA, wherein the sequence comprises a modification at one or more nucleotides in the regions marked by bold, underlined text.

In one embodiment, the modified miRNA comprises one or more of the following human sequences:

Let-7g (version E):
(SEQ ID NO: 12)
AGGCUGAGGUAGUAGUUUGUACAGUUUGAGGGUCUAUGAUACCACCCGG
UACAUCAGAUAACUGUACAGGCCACUGCCUUGCCA Let-7g (version I):
(SEQ ID NO: 13)
AGGCUGAGGUAGUAGUUUGUACAGUUUGAGGGCGUAUGAUACCACCCGG
UACAGGAUGCAACUGUACAGGCCACUGCCUUGCCA.

Also provided herein in another aspect, is a method for screening a candidate agent that modulates the function of a mature cardiomyocyte, the method comprising: (a) contacting a mature cardiomyocyte, or population thereof, with a candidate agent, wherein the mature cardiomyocyte is made by contacting a cardiomyocyte with a microRNA (miRNA) from the let-7 family; and (b) measuring a cardiac functional parameter in the cardiomyocyte or population thereof, wherein an increase or decrease in the level of the functional parameter in the cardiomyocyte or population thereof indicates that the candidate agent modulates heart function.

In one embodiment of this aspect and all other aspects described herein, the candidate agent increases the functional parameter of the mature cardiomyocyte.

In another embodiment of this aspect and all other aspects described herein, the candidate agent reduces the functional parameter of the mature cardiomyocyte.

In another embodiment of this aspect and all other aspects described herein, the cardiac functional parameter comprises contractile force, sarcomere length, gene expression, beat frequency, cell size, cell perimeter, or cell area.

In another embodiment of this aspect and all other aspects described herein, the cardiac functional parameter comprises fatty acid oxidation rates, glycolytic rates, glucose oxidation rates, oxygen consumption rate (OCR), or the extracellular acidification rate (ECAR).

In another aspect, described herein is a method of screening for cardiotoxicity of a drug or candidate agent. Where a number of drugs for various indications have turned out to have cardiotoxic effects, it can be of great benefit for drug development to be able to tell early on if a drug candidate has cardiotoxic effects. In this aspect, then, matured cardiomyocytes prepared according to the methods described herein are contacted with a candidate drug or agent and examined or monitored for toxic effects. This approach can detect those drugs, whether for non-cardiac or cardiac indications, that have cardiotoxic effects. In other aspects noted below, the matured cardiomyocyte can be derived from an individual or subject who has or is to be treated for a specific cardiac condition.

Another aspect provided herein relates to a method or toxicity assay comprising: (a) contacting a mature cardiomyocyte derived from a subject, or population thereof, with a candidate agent, wherein the mature cardiomyocyte is made by a process comprising contacting a cardiomyocyte with a microRNA (miRNA) from the let-7 family; and (b) measuring action potential duration and/or drug-induced arrhythmia in the cardiomyocyte or population thereof, wherein an increase in action potential duration and/or drug-induced arrhythmia in the cardiomyocyte or population thereof indicates that the subject is susceptible to cardiotoxicity by the candidate agent.

In one embodiment of this aspect and all other aspects described herein, the subject has a cardiac disease or disorder selected from the group consisting of: hereditary long QT syndrome, familial hypertrophic cardiomyopathy, and familial dilated cardiomyopathy.

In another embodiment of this aspect and all other aspects described herein, the action potential duration and/or drug-induced arrhythmia is determined by single cell patch clamp, immunostaining, and/or single-cell PCR.

In another embodiment of this aspect and all other aspects described herein, the immunostaining and/or single-cell PCR determines or measures expression of at least one cardiac ion channel.

BRIEF DESCRIPTION OF THE FIGURES

FIGS. 1A-1H The molecular signatures of in vitro cardiac maturation reflect in vivo cardiac maturation. (FIG. 1A) Schematic representation of large scale mRNA and miRNA sequencing using ILLUMINA™ platform from day 20 cardiomyocytes (CMs) and in vitro matured cardiomyocytes (CMs) derived from human embryonic stem cells (hESC) (H7). (FIGS. 1B, 1C) qPCR analysis of maturation markers in day 20-CMs and in vitro matured CMs. (FIG. 1D) Two dimensional principal component analysis using genome wide expression data for day 20-CMs, 1 yr old CMs (1yr-CM), human fetal atrium (HFA) and ventricular (HFV) samples attained using R. (FIG. 1E) Heat map depicting changes in gene expression of 12 different pathways between day 20-CM, 1yr-CMs HFA and HFV samples attained using the R™ statistical analysis software package. The rows reflect read counts and are standardized individually and shaded according to the Z score. (FIGS. 1F-H) Density plots using the R™ statistical analysis software package generated with fold change expression of genes from 4 representative categories for 1yr-CM (FIG. 1F), HFA (FIG. 1G) and HFV (FIG. 1H) relative to gene expression of day 20 CMs. x-axis indicates log 2 fold change in gene expression.

FIGS. 2A-2C Genome wide sequencing of in vitro matured cardiomyocytes reveals regulation of diverse miRNAs. (FIG. 2A) Scatter plot depicting expression of all miRNAs with deducible read counts. The x-axis indicates numbers of miRNAs and the y-axis indicates relative fold change expression. Shaded points highlight members of various miRNA families including let-7d,g,f,b,i; mir-378 f,g,e,b,a,i,c; mir-30b; mir-129-5p; mir-502-5p (FIG. 2B) Heat map generated using multi expression viewer includes fold changes of all significantly regulated miRNAs (FC≥2 and p≤0.001) that are in common between 1 yr and cEHTs relative to day 20 CMs. Shading indicates up and down-regulation. Numbers 1 and 2 indicate significantly up or down regulated miRNAs, respectively. (FIG. 2C) miRNA-mRNA target analysis using IPA with 1yr-CM expression data sets revealed 5 miRNAs with the highest number of targets in 1yr-CMs.

FIGS. 3A-3K Let-7 over expression (OE) accelerates hESC-CM maturation "in-the-dish". (FIGS. 3A-3C) qPCR analysis to (FIG. 3A) validate let-7i and 7g expression derived from miRNA sequencing analysis from day 20-CM and in vitro matured CMs (FIG. 3B) demonstrate that let-7i and let-7g OE in RUES2-CMs results in increased expression of the two members. EV indicates empty vector control in RUES2-CM (three biological replicates were analyzed for let-7 OE and EV samples) (FIG. 3C) examine the expression of maturation markers in H7 day 20 CMs, EV and RUES2-CMs. Gene expression is shown normalized first to GAPDH and then normalized to EV control. (FIG. 3D) α-actinin, β-actin, and DAPI staining of representative EV control, let-7i OE and let-7g OE CMs. Scale bar=50 µm. Compared to EV control, let-7 OE CMs showed significant changes in (FIG. 3E) cell perimeter (FIG. 3F) cell area (FIG. 3G) circularity index (FIG. 3H) sarcomere length. n=50 cells per condition, 3 biological replicates. (FIG. 3I) indicates representative force traces in EV control and let-7 OE CMs (FIG. 3J) significant increase in twitch force in let-7 OE CMs. n=25 for EV control, n=32 for let-7i OE and n=29 for let-7g OE from a total of 3 biological replicates (FIG. 3K). frequency of beating CMs. EV, let-7i OE and let-7g OE CMs are collected at day 30 and hence are 10 days older than day 20 samples.

(FIG. 4A) Scatter plot of let-7g OE (y-axis) vs. EV control (x-axis) from the mRNA sequencing data set. Red dots indicate maturation marker genes in the data set. (FIG. 4B) 2D-PCA using genes from 12 pathways (indicated in FIG. 1E) across the analyzed samples as indicated in the figure. (FIG. 4C) Venn diagram showing the intersection of 34 genes differentially spliced in fetal, 1 yr and let-7 OE CMs. (FIG. 4D) Heat map showing the proportion of the most changed isoform of 34 genes detected as differentially spliced in each condition. Each value is the estimated proportion of that isoform among all expressed isoforms of the same gene in that condition. Row labels are the AceView gene/Identifiers. (FIG. 4E) 2D-PCA based on all 337 transcripts of genes listed in panel d applied to all replicates from these 6 conditions. (FIG. 4F) Heat map demonstrating changes in gene expression of 12 different pathways between EV control and let-7g OE CMs. Left to right columns 1-2 and 3-5 represent biological replicates of EV and let-7g OE CMs, respectively. The rows reflect read counts of various genes in the different categories. Rows are standardized individually and shaded according to the Z score. (FIG. 4G) Density plots using R generated with fold change expression (X-axis indicates log 2 fold change) of genes from four categories, indicative of cardiac function for let-7 OE/EV CMs.

(FIG. 5B) qPCR analysis of candidate let-7 targets of the insulin pathway and genes from the FA metabolism. (FIG. 5C) Representative OCR profile in response to ATP synthase inhibitor oligomycin, uncoupler of electron transport and oxidative phosphorylation, FCCP and electron transport chain blockers rotenone and antimycin during mito-stress assay. (FIG. 5D) Quantification of maximal respiration capacity, i.e., changes in response to FCCP treatment after inhibition of ATP synthase by oligomycin. n=24 from 3 biological replicates. (FIG. 5E) mitochondrial DNA copy number was determined by measuring the ratio of MtDNA to genomic DNA using primers specific for mitochondrial DNA gene, Col (mtCol) and normalizing to chromosomal gene GAPDH. (FIG. 5F) Representative OCR trace of let-7g OE cardiomyocytes for fatty acid stress measuring Etomixir (ETO) responsive OCR changes after palmitate addition. (FIG. 5G) Quantification of changes in OCR in response to ETO. n=32 from 3 biological replicates.

(FIG. 11C) Percentage of cells that has been successfully transduced.

(FIG. 12A) Density plots generated using fold change expression of maturation marker genes in let-7g OE CMs relative to EV control. (FIG. 12B) An unbiased clustering analysis using expression data for genes from the 12 categories (see FIG. 1) demonstrates that let-7 OE CMs cluster with H7 1yr-CMs and IMR90iPSCs 1yr-CMs.

(FIG. 16B) glucose addition in glucose stress assay. In both the assays the values were normalized to the number of cells present in each well quantified by Hoechst staining.

FIG. 19A demonstrates that let-7i and let-7g were over expressed up to 8 fold and 10 fold relative to empty vector (EV) control. Experiments were validated with 3 biological and 3 technical replicates. FIG. 19B qPCR validated the down-regulation of let-7 targets (lin28 and HMGA2) and upregulation of cardiomyocyte maturation markers in let-7i OE and let-7g OE CMs.

FIG. 20A demonstrates that the modified version of let-7g-E shows a much higher expression compared to EV as well as the native form of let-7g. (FIG. 20B) Targets of let-7 are repressed when we overexpress let-7g-E similar to that seen during over-expression of let-7g.

(FIGS. 21A-21C) qPCR analysis to (FIG. 21A) examine Lin28a expression in Lin28a OE RUES2-CMs vs. EV control. FIG. 21B demonstrates that let-7i and let-7g are down-regulated in Lin28a OE hESC-CMs. FIG. 21C evaluates the expression of maturation markers in Lin28a OE RUES2-CMs vs. EV control. EV indicates empty vector control in RUES2-CMs (three biological replicates were analyzed for Lin28a and EV samples). (FIG. 21D) α actinin and DAPI staining of representative EV control and Lin28a OE CMs. Scale bar=25 µm. Compared to EV control, Lin28a OE CMs showed (FIGS. 21E-21G) significant decrease in (FIG. 21E) cell perimeter (FIG. 21F) cell area (FIG. 21G) sarcomere length and (FIG. 21H) an increase in circularity index. N=50 cells per condition, 3 biological replicates.

(FIG. 22A) Depicts representative zebrafish embryos 72 hour post fertilization (hpf) receiving negative control MO (CMO)(left) and lin28 MOs (right). The arrows indicate the pericardial region. A scaled outline of the atrium and ventricle for control vs. lin28 morphants are shown as cartoons on the left bottom corner. Scale=100 µm. (FIGS. 22B-22C) qPCR analysis in MO treated zebrafish 24 and 72 hpf to determine the expression of (FIG. 22B) let-7i and (FIG. 22C) maturation markers. MO injection was done at single cell stage. Values represent mean of 3 independently pooled samples. n=60±10 for each treatment. For (FIG. 22C) p-values were calculated 24 hpf and 72 hpf in comparison to negative control MO. (FIG. 22D) Without wishing to be bound by theory, FIG. 22 shows a proposed model for let-7 action in CM maturation. Let-7 inhibits its targets from the PI3/AKT/Insulin pathway and TRIM-71/LIN-41. Inhibition of TRIM-71/LIN41 further results in the up regulation of EGR1. Down regulation of the insulin pathway and up regulation EGR1 likely regulate multitude of genes that could culminate to an increased FA metabolism, growth and force of contraction resulting in cardiac maturation. The arrows on the side of the each of the regulators indicate the direction of change when let-7 is induced.

DETAILED DESCRIPTION

Figure 1A:
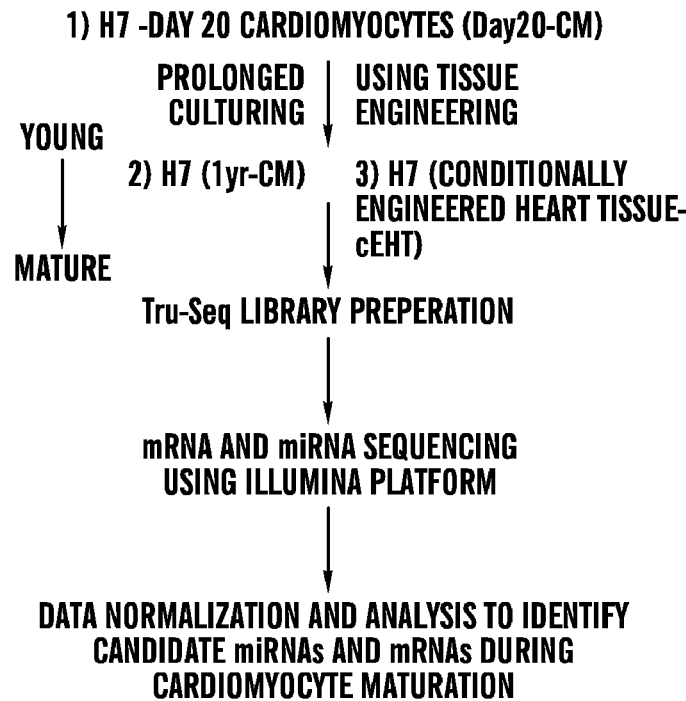

Generation of cardiomyocytes from stem cells, including human embryonic stem cells (hESCs), has many therapeutic implications, as well as usefulness in, e.g., drug screening and disease modeling. While cardiomyocytes derived from hESCs have been shown to exhibit cardiac properties such as e.g., spontaneous beating, cardiac-related action potentials, calcium transients and even engraftment to form new myocardium that is electromechanically integrated with the host myocardium, such cardiomyocytes exhibit functional and physiological similarity to cardiomyocytes with a fetal phenotype. This can diminish the usefulness of in vitro derived cardiomyocytes, e.g., for use in modeling and/or treatment of adult-related heart disease.

Provided herein are methods for inducing maturation of a cardiomyocyte in vitro, ex vivo, or in vivo to an adult-like or mature phenotype by contacting the cardiomyocyte with and/or administering to a subject a let-7 miRNA.

DEFINITIONS

As used herein the term "stem cell" refers to a cell (e.g., a human cell) that can self-renew and differentiate to at least one cell type. The term "human stem cell" encompasses human stem cell lines, human-derived iPS cells, human embryonic stem cells, human pluripotent cells, human multipotent cells or human adult stem cells.

As used herein, the term "induced to differentiate" refers to a chemical/biological treatment, a physical environment or a genetic modification that is conducive to the formation of more differentiated cells (e.g., cardiac-lineage cells or cardiomyocytes) from pluripotent or multipotent stem cells. Differentiation can be assessed by the appearance of distinct cell-type specific markers or by the loss of stem cell specific markers, or both.

As used herein, the term "fetal-like phenotype" or "fetal-like cardiomyocyte" refers to a cardiomyocyte that comprises a phenotype similar to the cardiomyocytes in the developing fetal heart. At a minimum, a fetal-like phenotype refers to a reliance on glycolysis for energy. Expression of fetal isoforms of e.g., myosin heavy chain (MHC-P), troponin T, and carnitine palmitoyl transferase I are also indicative of a fetal-like phenotype.

Similarly, the terms "adult-like phenotype," or "mature cardiomyocyte" refers to a cardiomyocyte that comprises a phenotype similar to cardiomyocytes present in a non-diseased adult heart. At a minimum, a mature cardiomyocyte relies on β-oxidation of fatty acids as the primary source of energy, with glucose oxidation and lactate oxidation also contributing to energy production. A mature cardiomyocyte also expresses one or more, and preferably a plurality of cardiac protein isoforms indicative of an adult heart, for example, MHC-α, and troponin I.

As used herein, the term "maturation of the cardiomyocyte" refers to a process that induces a cardiomyocyte having a fetal-like phenotype to switch, at least partially, to an adult-like phenotype. Maturation of the cardiomyocyte is predominantly determined by assessing a switch in energy substrate preference from glycolysis to fatty acid oxidation; however changes in isoform expression of myosin heavy chain, troponin, or carnitine palmitoyl transferase I can also be used to determine the timing and/or degree of maturation. While change in either energy substrate use or cardiac protein isoform expression are necessarily indicative of maturation, the maturation of a cardiomyocyte is also evident by determining an increase in sarcomere length, an increase in cell size, an increase in cell perimeter, an increase in contractile force, or a reduction in beat frequency of the mature cardiomyocyte as compared to a fetal-like cardiomyocyte.

As used herein, the phrase "resistant to inhibition by LIN28" or "insensitive to inhibition by LIN28" refers to a modified let-7 pre-miRNA comprising at least one mutation in the L1N28 binding site, such that L1N28 does not recognize or substantially bind to the let-7 pre-miRNA, thereby permitting the let-7 pre-miRNA to be processed to a mature let-7 miRNA.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g., the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, at least about a 20-fold increase, at least about a 50-fold increase, at least about a 100-fold increase, at least about a 1000-fold increase or more as compared to a reference level.

As used herein, the phrase "cardiovascular condition, disease or disorder" is intended to include all disorders characterized by insufficient, undesired or abnormal cardiac function, e.g., ischemic heart disease, hypertensive heart disease and pulmonary hypertensive heart disease, valvular disease, congenital heart disease and any condition which leads to congestive heart failure in a subject, particularly a human subject. The methods and compositions described herein are particularly useful for repairing damaged myocardium, characterized by loss of myocytes, loss of function, formation of scar tissue etc. Insufficient or abnormal cardiac function can be the result of disease, injury and/or aging. By way of background, a response to myocardial injury follows a well-defined path in which some cells die while others enter a state of hibernation where they are not yet dead but are dysfunctional. This is followed by infiltration of inflammatory cells, deposition of collagen as part of scarring, all of which happen in parallel with in-growth of new blood vessels and a degree of continued cell death. As used herein, the term "ischemia" refers to any localized tissue ischemia due to reduction of the inflow of blood. The term "myocardial ischemia" refers to circulatory disturbances caused by coronary atherosclerosis and/or inadequate oxygen supply to the myocardium. For example, an acute myocardial infarction represents an irreversible ischemic insult to myocardial tissue. This insult results from an occlusive (e.g., thrombotic or embolic) event in the coronary circulation and produces an environment in which the myocardial metabolic demands exceed the supply of oxygen to the myocardial tissue.

As used herein, the phrase "cardiac tissue damage" refers to damage to the heart as a result of cardiomyocyte loss/death and/or a partial or complete loss of contractile function in a region of the heart (e.g., an infarct area; cardiomyopathy; heart failure; cardiac remodeling etc.). Cardiac tissue damage can be a result of an acute myocardial infarction (i.e., AMI or a "heart attack"), ischemia/reperfusion injury, autophagy, cardiomyopathy, dilated cardiomyopathy, heart failure, restenosis, apoptosis, or necrosis.

As used herein, the term "cardiac functional parameter" refers to a morphological, phenotypic and/or functional parameter that can be measured in cultured cardiomyoctes. Such parameters include, but are not limited to, contractile force, sarcomere length, gene expression, beat frequency, cell size, cell perimeter, or cell area. In one embodiment, the cardiac functional parameter refers to the energy substrate preference of the cardiomyocte(s) in culture, for example, a preference for glycolytic metabolism of glucose vs. beta-oxidation of fatty acids (e.g., palmitate).

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment of the invention.

Stem Cells and/or Pluripotent Stem Cells

Essentially any stem cell with the ability to differentiate along the mesodermal lineage ((e.g., an embryonic stem cell) and/or pluripotent stem cell (e.g., an induced pluripotent stem cell)) can be used to derive cardiomyocytes in vitro. In one embodiment, the stem cells and/or pluripotent stem cells are human stem cells and/or human pluripotent stem cells.

Embryonic Stem Cells:

Embryonic stem cells and methods of their retrieval are well known in the art and are described, for example, in Trounson A O (Reprod Fertil Dev (2001) 13: 523), Roach M L (Methods Mol Biol (2002) 185: 1), and Smith A G (Annu Rev Cell Dev Biol (2001) 17:435). The term "embryonic stem cell" is used to refer to the pluripotent stem cells of the inner cell mass of the embryonic blastocyst (see e.g., U.S. Pat. Nos. 5,843,780, 6,200,806). Such cells can similarly be obtained from the inner cell mass of blastocysts derived from somatic cell nuclear transfer (see, for example, U.S. Pat. Nos. 5,945,577, 5,994,619, 6,235,970).

Cells derived from embryonic sources can include embryonic stem cells or stem cell lines obtained from a stem cell bank or other recognized depository institution. Other means of producing stem cell lines include methods comprising the use of a blastomere cell from an early stage embryo prior to formation of the blastocyst (at around the 8-cell stage). Such techniques correspond to the pre-implantation genetic diagnosis technique routinely practiced in assisted reproduction clinics. The single blastomere cell is co-cultured with established ES-cell lines and then separated from them to form fully competent ES cell lines.

Embryonic stem cells are considered to be undifferentiated when they have not committed to a specific differentiation lineage. Such cells display morphological characteristics that distinguish them from differentiated cells of embryo or adult origin. Undifferentiated embryonic stem (ES) cells are easily recognized by those skilled in the art, and typically appear in the two dimensions of a microscopic view in colonies of cells with high nuclear/cytoplasmic ratios and prominent nucleoli. In some embodiments, the cardiomyocytes described herein are not derived from embryonic stem cells or any other cells of embryonic origin.

Adult Stem Cells:

Adult stem cells are stem cells derived from tissues of a post-natal or post-neonatal organism or from an adult organism. An adult stem cell is structurally distinct from an embryonic stem cell not only in markers it does or does not express relative to an embryonic stem cell, but also by the presence of epigenetic differences, e.g., differences in DNA methylation patterns.

Induced Pluripotent Stem Cells (iPSCs):

In some embodiments, the cardiomyocytes described herein are derived from induced pluripotent stem cells (iPSCs). An advantage of using induced pluripotent stem cells is that the cells can be derived from the same subject to which the cardiomyocytes are to be administered. That is, a somatic cell can be obtained from a subject, reprogrammed to an induced pluripotent stem cell, and then re-differentiated into a cardiomyocyte to be administered to the subject (e.g., autologous cells). Since the cardiac progenitors are essentially derived from an autologous source, the risk of engraftment rejection or allergic responses is reduced compared to the use of cells from another subject or group of subjects. In some embodiments, the cardiac progenitors are derived from non-autologous sources. In addition, the use of iPSCs negates the need for cells obtained from an embryonic source. Thus, in one embodiment, the stem cells used in the disclosed methods are not embryonic stem cells.

Although differentiation is generally irreversible under physiological contexts, several methods have been recently developed to reprogram somatic cells to induced pluripotent stem cells. Exemplary methods are known to those of skill in the art and are described briefly herein below. iPSCs resemble ES cells as they restore the pluripotency-associated transcriptional circuitry and much of the epigenetic landscape. In addition, iPSCs satisfy all the standard assays for pluripotency: specifically, in vitro differentiation into cell types of the three germ layers, teratoma formation, contribution to chimeras, germline transmission (Maherali and Hochedlinger, 2008), and tetraploid complementation (Woltjen et al., 2009).

As used herein, the term "reprogramming" refers to a process that alters or reverses the differentiation state of a differentiated cell (e.g., a somatic cell). Stated another way, reprogramming refers to a process of driving the differentiation of a cell backwards to a more undifferentiated or more primitive type of cell. It should be noted that placing many primary cells in culture can lead to some loss of fully differentiated characteristics. Thus, simply culturing such cells included in the term differentiated cells does not render these cells non-differentiated cells (e.g., undifferentiated cells) or pluripotent cells. The transition of a differentiated cell to pluripotency requires a reprogramming stimulus beyond the stimuli that lead to partial loss of differentiated character in culture. Reprogrammed cells also have the characteristic of the capacity of extended passaging without loss of growth potential, relative to primary cell parents, which generally have capacity for only a limited number of divisions in culture.

The cell to be reprogrammed can be either partially or terminally differentiated prior to reprogramming. In some embodiments, reprogramming encompasses reversion of the differentiation state of a differentiated cell (e.g., a somatic cell) to a pluripotent state or a multipotent state. In some embodiments, reprogramming encompasses complete or partial reversion of the differentiation state of a differentiated cell (e.g., a somatic cell) to an undifferentiated cell (e.g., an embryonic-like cell). The resulting cells are referred to as "reprogrammed cells;" when the reprogrammed cells are pluripotent, they are referred to as "induced pluripotent stem cells (iPSCs or iPS cells)."

Reprogramming can involve alteration, e.g., reversal, of at least some of the heritable patterns of nucleic acid modification (e.g., methylation), chromatin condensation, epigenetic changes, genomic imprinting, etc., that occur during cellular differentiation. Reprogramming is distinct from simply maintaining the existing undifferentiated state of a cell that is already pluripotent or maintaining the existing less than fully differentiated state of a cell that is already a multipotent cell (e.g., a hematopoietic stem cell). Reprogramming is also distinct from promoting the self-renewal or proliferation of cells that are already pluripotent or multipotent. The specific reprogramming approach or method used to generate pluripotent stem cells from somatic cells is not critical to the claimed invention. Thus, any method that re-programs a somatic cell to the pluripotent phenotype would be appropriate for use in the methods described herein.

Reprogramming methodologies using defined combinations of transcription factors have been described for generating induced pluripotent stem cells. Yamanaka and Takahashi converted mouse somatic cells to ES cell-like cells with expanded developmental potential by the direct transduction of genes encoding Oct4, Sox2, Klf4, and c-Myc (Takahashi and Yamanaka, 2006).

Subsequent studies have shown that human iPS cells can be obtained using similar transduction methods (Lowry et al., 2008; Park et al., 2008; Takahashi et al., 2007; Yu et al., 2007b), and the transcription factor trio, OCT4, SOX2, and NANOG, has been established as the core set of transcription factors that govern pluripotency (Jaenisch and Young, 2008). The production of iPS cells can be achieved by the introduction of nucleic acid sequences encoding stem cell-associated genes into an adult, somatic cell, historically using viral vectors.

iPS cells can be generated or derived from terminally differentiated somatic cells, as well as from adult stem cells, or somatic stem cells. That is, a non-pluripotent progenitor cell can be rendered pluripotent or multipotent by reprogramming. In such instances, it may not be necessary to include as many reprogramming factors as required to reprogram a terminally differentiated cell. Further, reprogramming can be induced by the non-viral introduction of reprogramming factors, e.g., by introducing the proteins themselves, or by introducing nucleic acids that encode the reprogramming factors, or by introducing messenger RNAs that upon translation produce the reprogramming factors (see e.g., Warren et al., Cell Stem Cell, 2010 Nov. 5; 7(5):618-30). Reprogramming can be achieved by introducing a combination of nucleic acids encoding stem cell-associated genes including, for example Oct-4 (also known as Oct-3/4 or Pouf51), Sox1, Sox2, Sox3, Sox 15, Sox 18, NANOG, Klf1, Klf2, Klf4, Klf5, NR5A2, c-Myc, 1-Myc, n-Myc, Rem2, Tert, and LIN28. In one embodiment, reprogramming using the methods and compositions described herein can further comprise introducing one or more of Oct-3/4, a member of the Sox family, a member of the Klf family, and a member of the Myc family to a somatic cell. In one embodiment, the methods and compositions described herein further comprise introducing one or more of each of Oct-4, Sox2, Nanog, c-MYC and Klf4 for reprogramming. As noted above, the exact method used for reprogramming is not necessarily critical to the methods and compositions described herein. However, where cells differentiated from the reprogrammed cells are to be used in, e.g., human therapy, in one embodiment the reprogramming is not effected by a method that alters the genome. Thus, in such embodiments, reprogramming is achieved, e.g., without the use of viral or plasmid vectors. In addition to the protein-based and the RNA-based methods (see e.g., Warren et al., supra), recent evidence indicates somatic cells can be re-programmed by e.g., exposure of the cells to unphysiological stress, e.g., in culture (see e.g., WO2013/163296, which is incorporated herein by reference in its entirety). These methods of re-programming may be preferred for cells to be used for therapeutic purposes, as they are less likely to provoke genomic damage likely to promote, e.g., cancer.

The efficiency of reprogramming (i.e., the number of reprogrammed cells) derived from a population of starting cells can be enhanced by the addition of various small molecules as shown by Shi, Y., et al (2008) Cell-Stem Cell 2:525-528, Huangfu, D., et al (2008) Nature Biotechnology 26(7):795-797, and Marson, A., et al (2008) Cell-Stem Cell 3:132-135. Thus, an agent or combination of agents that enhance the efficiency or rate of induced pluripotent stem cell production can be used in the production of patient-specific or disease-specific iPSCs. Some non-limiting examples of agents that enhance reprogramming efficiency include soluble Wnt, Wnt conditioned media, BIX-01294 (a G9a histone methyltransferase), PD0325901 (a MEK inhibitor), DNA methyltransferase inhibitors, histone deacetylase (HDAC) inhibitors, valproic acid, 5'-azacytidine, dexamethasone, suberoylanilide, hydroxamic acid (SAHA), vitamin C, and trichostatin (TSA), among others.

Other non-limiting examples of reprogramming enhancing agents include: Suberoylanilide Hydroxamic Acid (SAHA (e.g., MK0683, vorinostat) and other hydroxamic acids), BML-210, Depudecin (e.g., (−)-Depudecin), HC Toxin, Nullscript (4-(1,3-Dioxo-1H,3H-benzo[de]isoquinolin-2-yl)-N-hydroxybutanamide), Phenylbutyrate (e.g., sodium phenylbutyrate) and Valproic Acid ((VPA) and other short chain fatty acids), Scriptaid, Suramin Sodium, Trichostatin A (TSA), APHA Compound 8, Apicidin, Sodium Butyrate, pivaloyloxymethyl butyrate (Pivanex, AN-9), Trapoxin B, Chlamydocin, Depsipeptide (also known as FR901228 or FK228), benzamides (e.g., CI-994 (e.g., N-acetyl dinaline) and MS-27-275), MGCD0103, NVP-LAQ-824, CBHA (m-carboxycinnaminic acid bishydroxamic acid), JNJ16241199, Tubacin, A-161906, proxamide, oxamflatin, 3-Cl-UCHA (e.g., 6-(3-chlorophenylureido) caproic hydroxamic acid), AOE (2-amino-8-oxo-9,10-epoxydecanoic acid), CHAP31 and CHAP 50. Other reprogramming enhancing agents include, for example, dominant negative forms of the HDACs (e.g., catalytically inactive forms), siRNA inhibitors of the HDACs, and antibodies that specifically bind to the HDACs. Such inhibitors are available, e.g., from BIOMOL International, Fukasawa, Merck Biosciences, Novartis, Gloucester Pharmaceuticals, Aton Pharma, Titan Pharmaceuticals, Schering AG, Pharmion, MethylGene, and Sigma Aldrich.

To confirm the induction of pluripotent stem cells for use with the methods described herein, isolated clones can be tested for the expression of a stem cell marker. Such expression in a cell derived from a somatic cell identifies the cells as induced pluripotent stem cells. Stem cell markers can be selected from the non-limiting group including SSEA3, SSEA4, CD9, Nanog, Fbx15, Ecat1, Esg1, Eras, Gdf3, Fgf4, Cripto, Dax1, Zpf296, Slc2a3, Rex1, Utf1, and Nat1. In one embodiment, a cell that expresses Oct4 or Nanog is identified as pluripotent. Methods for detecting the expression of such markers can include, for example, RT-PCR and immunological methods that detect the presence of the encoded polypeptides, such as Western blots or flow cytometric analyses. In some embodiments, detection does not involve only RT-PCR, but also includes detection of protein markers. Intracellular markers may be best identified via RT-PCR, while cell surface markers are readily identified, e.g., by immunocytochemistry.

The pluripotent stem cell character of isolated cells can be confirmed by tests evaluating the ability of the iPSCs to differentiate to cells of each of the three germ layers. As one example, teratoma formation in nude mice can be used to evaluate the pluripotent character of the isolated clones. The cells are introduced to nude mice and histology and/or immunohistochemistry is performed on a tumor arising from the cells. The growth of a tumor comprising cells from all three germ layers, for example, further indicates that the cells are pluripotent stem cells.

Somatic Cells for Reprogramming to iPSCs:

Somatic cells, as that term is used herein, refer to any cells forming the body of an organism, excluding germline cells. Every cell type in the mammalian body—apart from the sperm and ova, the cells from which they are made (gametocytes) and undifferentiated stem cells—is a differentiated somatic cell. For example, internal organs, skin, bones, blood, and connective tissue are all made up of differentiated somatic cells.

Additional somatic cell types for use with the compositions and methods described herein include: a fibroblast (e.g., a primary fibroblast), a muscle cell (e.g., a myocyte), a cumulus cell, a neural cell, a mammary cell, a hepatocyte, a cardiomyocyte and a pancreatic islet cell. In some embodiments, the somatic cell is a primary cell line or is the progeny of a primary or secondary cell line. In some embodiments, the somatic cell is obtained from a human sample, e.g., a hair follicle, a blood sample, a biopsy (e.g., a skin biopsy or an adipose biopsy), a swab sample (e.g., an oral swab sample), and is thus a human somatic cell.

Some non-limiting examples of differentiated somatic cells include, but are not limited to, epithelial, endothelial, neuronal, adipose, cardiac, skeletal muscle, immune cells, hepatic, splenic, lung, circulating blood cells, gastrointestinal, renal, bone marrow, and pancreatic cells. In some embodiments, a somatic cell can be a primary cell isolated from any somatic tissue including, but not limited to brain, liver, lung, gut, stomach, intestine, fat, muscle, uterus, skin, spleen, endocrine organ, bone, etc. Further, the somatic cell can be from any mammalian species, with non-limiting examples including a murine, bovine, simian, porcine, equine, ovine, or human cell. In some embodiments, the somatic cell is a human somatic cell.

When reprogrammed cells are used for generation of cardiomyocytes to be used in the therapeutic treatment of disease, it is desirable, but not required, to use somatic cells isolated from the patient being treated. In some embodiments, a method for selecting the reprogrammed cells from a heterogeneous population comprising reprogrammed cells and somatic cells they were derived or generated from can be performed by any known means. For example, a drug resistance gene or the like, such as a selectable marker gene can be used to isolate the reprogrammed cells using the selectable marker as an index. It is emphasized that such a selectable marker is not required—that is, in some embodiments reprogrammed pluripotent stem cells can be identified on the basis of morphology. See, e.g., US 2010/0184051. It is noted herein that reprogramming can be performed using any means known in the art. That is, the specific reprogramming approach is not critical for the methods or processes of maturing cardiomyocytes as described herein.

Reprogrammed somatic cells as disclosed herein can express any number of pluripotent cell markers, including: alkaline phosphatase (AP); ABCG2; stage specific embryonic antigen-1 (SSEA-1); SSEA-3; SSEA-4; TRA-1-60; TRA-1-81; Tra-2-49/6E; ERas/ECAT5, E-cadherin; b-III-tubulin; a-smooth muscle actin (a-SMA); fibroblast growth factor 4 (Fgf4), Cripto, Dax1; zinc finger protein 296 (Zfp296); N-acetyltransferase-1 (Nat1); (ES cell associated transcript 1 (ECAT1); ESG1/DPPA5/ECAT2; ECAT3; ECAT6; ECAT7; ECAT8; ECAT9; ECAT10; ECAT15-1; ECAT15-2; Fthl17; Sal14; undifferentiated embryonic cell transcription factor (Utf1); Rex1; p53; G3PDH; telomerase, including TERT; silent X chromosome genes; Dnmt3a; Dnmt3b; TRIM28; F-box containing protein 15 (Fbx15); Nanog/ECAT4; Oct3/4; Sox2; Klf4; c-Myc; Esrrb; TDGF1; GABRB3; Zfp42, FoxD3; GDF3; CYP25A1; developmental pluripotency-associated 2 (DPPA2); T-cell lymphoma breakpoint 1 (Tell); DPPA3/Stella; DPPA4; other general markers for pluripotency, etc. Other markers can include Dnmt3L; Sox15; Stat3; Grb2; b-catenin, and Bmi1. Such cells can also be characterized by the down-regulation of markers characteristic of the somatic cell from which the induced pluripotent stem cell is derived.

It is understood that the cardiomyocytes produced from e.g., human embryonic stem cells, cardiac-lineage specific progenitors, or induced pluripotent stem cells (iPSCs) will typically yield cardiomyocytes with a fetal phenotype, as that term is used herein.

Cardiomyocyte Differentiation

Essentially any method of differentiation can be used to produce a cardiomyocyte having a fetal-like phenotype to be used with the methods and compositions provided herein to induce cardiomyocyte maturation. Methods of direct differentiation from embryonic stem cells and/or induced pluripotent stem cells are contemplated herein. In addition, step-wise differentiation through a cardiomyocyte progenitor is also contemplated herein.

A "cardiomyocyte progenitor" is defined as a cell (e.g., a human cell) that is capable (without dedifferentiation or reprogramming) of giving rise to progeny that include cardiomyocytes. Such precursors may express markers typical of the lineage, including, without limitation, cardiac troponin I (cTnI), cardiac troponin T (cTnT), sarcomeric myosin heavy chain (MHC), GATA4, Nkx2.5, N-cadherin, beta1-adrenoreceptor (beta1-AR), the MEF-2 family of transcription factors, creatine kinase MB (CK-MB), myoglobin, or atrial natriuretic factor (ANF). Throughout this disclosure, techniques and compositions that refer to a "cardiomyocyte progenitor" can be taken to apply equally to cells at any stage of cardiomyocyte ontogeny without restriction, as defined above, unless otherwise specified. The cells may or may not have the ability to proliferate or exhibit contractile activity. The culture conditions may optionally comprise agents that enhance differentiation to a specific lineage. For example, myocardial lineage differentiation can be promoted by including cardiotrophic agents in the culture, e.g., agents capable of forming high energy phosphate bonds (such as creatine) and acyl group carrier molecules (such as carnitine); and a cardiomyocyte calcium channel modulator (such as taurine). Optionally, cardiotropic factors, including, but not limited to those described in U.S. 2003/0022367 (which is incorporated herein in its entirety by reference), may be added to the culture. Such factors can include, but are not limited to nucleotide analogs that affect DNA methylation and alter expression of cardiomyocyte-related genes; TGF-beta ligands, such as activin A, activin B, insulin-like growth factors, bone morphogenic proteins, fibroblast growth factors, platelet-derived growth factor natriuretic factors, insulin, leukemia inhibitory factor (LIF), epidermal growth factor (EGF), TGFalpha, and products of the cripto gene; antibodies, peptidomimetics with agonist activity for the same receptors, pseudo ligands, for example peptides and antibodies, cells secreting such factors, and other methods for directed differentiation of stem cells along specific cell lineages in particular cardiomyocyte lineages.

In one embodiment, cardiomyocytes are derived using a cardiac progenitor cell differentiation protocol derived from previously reported monolayer directed differentiation methods (Laflamme and Murry, 2011; Lian et al., 2012; Paige et al., 2010). In brief, this involves the induction of a monolayer of hESCs with activin A and bone morphogenetic protein-4 (BMP4) under serum- and insulin-free conditions. In this embodiment, cells are also exposed to the Wnt agonist CHIR 99021 followed by the Wnt antagonist Xav939 during the early stages of differentiation. From 7 days of in vitro differentiation, the cells are fed every alternate day with serum-free RPMI-B27 plus insulin media. After 20 days of in vitro differentiation, the cells are trypsinized and replated. Only those cell preparations that had at least 70% cardiac troponin T-positive CMs (as observed by flow cytometry) are used for further experiments.

Fetal Vs. Adult Phenotypes of Cardiomyocytes

The methods and compositions described herein permit the maturation of cardiomyocytes comprising a fetal phenotype to cardiomyocytes exhibiting a mature cardiac phenotype. Mature cardiomyocytes will permit better treatment of adult-onset cardiac diseases, disorders, or injury as their phenotype corresponds to that of the adult heart. Mature cardiomyocytes are also advantageous for drug screening and disease modeling applications aimed at developing therapies that will benefit patients with adult or mature cardiac tissues.

Fetal cardiomyocytes rely on glucose as an energy substrate for metabolism through the glycolytic pathway. Since the fetus is not exposed to air or oxygen, the heart relies on anaerobic metabolism through glycolysis. Glycolysis comprises the breakdown of glucose to two molecules of pyruvate and yields a small amount of energy in the form of ATP. This is in contrast to the profile of energy metabolism that is observed in adult or mature cardiomyocytes, which rely mainly on fatty acids as a source of energy. The metabolism of both fatty acids and the complete oxidation of glucose (i.e., from glucose to $CO_2$, $H_2O$ and energy equivalents) requires oxygen and participation of the electron transport chain. Adult cardiomyocytes generate a majority of the energy they need to sustain basal contractile function from the oxidation of fatty acids, such as palmitate.

During development there is a profound shift in the metabolic profile of cardiomyocytes from the use of glycolysis to the use of fatty acids as the preferred source of energy. Thus the mature cardiomyocyte and the fetal cardiomyocyte differ in terms of respiratory capacity. This shift in the profile of the heart is also evident in a shift in gene expression profiles as well as cell morphology or functional changes.

For example, mature cardiomyocytes are larger in size, have longer sarcomere length, have increased contractile force, and a reduced frequency of beating compared to fetal cardiomyocytes. In addition, mature cardiomyocytes show a significant upregulation in gene expression of e.g., cardiac troponin T, myosin heavy chain 7, sarcoendoplasmic reticulum ATPase, gap junction protein alpha 1/connexin 43, and ryanodine receptor 2 (see e.g., the working examples). In some cases, these gene expression changes are accompanied by an isoform switch of certain proteins. As an example, cardiac Troponin T is expressed in both the fetal and adult heart, but cardiac Troponin I is expressed only in the adult cardiomyocyte (Kim, S H et al., (2002) Circ J 66(10):959-64). In addition, myosin heavy chain-β is predominantly expressed in the fetal heart, while the adult heart expresses myosin heavy chain-α.

Let-7 miRNAs

Let-7 is an endogenous miRNA which functions as a gene silencing molecule to regulate, at the posttranscriptional level, the expression of some known protein-coding genes that comprise a let-7 target sequence. Let-7 miRNA and homologues and variants thereof include conservative substitutions, additions, and deletions therein not adversely affecting the structure or gene silencing function. Also included are let-7 miRNAs that lack sensitivity to LIN28 inhibition. The term "let-7' can refer to any of the nucleic acids encoding a let-7 family member from humans, including but not limited to NCBI Accession Nos. AJ421724, AJ421725, AJ421726, AJ421727, AJ421728, AJ421729, AJ421730, AJ421731, AJ421732, and biologically active sequence variants of let-7, including alleles, and in vitro generated derivatives of let-7 that demonstrate let-7 activity in that it is capable of binding to and inhibiting the expression of a gene comprising the let-7 target sequence, where the target sequence is 5'-AACTATACAACCTACTAC-CTCA-3' (SEQ ID NO: 11). Let-7 also encompasses all isoforms of let-7, for example but not limited to let-7 family members including let-7a-1 (SEQ ID NO:1); let-7a-2 (SEQ ID NO:2); let-7b (SEQ ID NO:3); hsa-let-7c (SEQ ID NO:4); hsa-let-7d (SEQ ID NO:5); hsa-let-7e (SEQ ID NO:6); hsa-let-7f-1 (SEQ ID NO:7); let-7f-2 (SEQ ID NO: 8); let-7g (SEQ ID NO. 9), and let-7i (SEQ ID NO: 10). In some embodiments, the let-7 miRNA sequence is a human sequence or a modified human sequence. In some embodiments, the let-7 miRNA used in the methods described herein comprises at least one of the following human sequences:

```
>hsa-let-7a-1 (miRBase Ref. No.: MI0000060)
                                        (SEQ ID NO: 1)
UGGGAUGAGGUAGUAGGUUGUAUAGUUUUAGGGUCACACCCACCACU
GGGAGAUAACUAUACAAUCUACUGUCUUUCCUA >hsa-let-7a-2 (miRBase Ref. No.: MI0000061)
                                        (SEQ ID NO: 2)
AGGUUGAGGUAGUAGGUUGUAUAGUUUAGAAUUACAUCAAGGGAGAU
AACUGUACAGCCUCCUAGCUUUCCU >hsa-let-7b (miRBase Ref. No.: MI0000063)
                                        (SEQ ID NO: 3)
CGGGGUGAGGUAGUAGGUUGUGUGGUUUCAGGGCAGUGAUGUUGCCC
CUCGGAAGAUAACUAUACAACCUACUGCCUUCCCUG
```

-continued

```
>hsa-let-7c (miRBase Ref. No.: MI0000064)
                                        (SEQ ID NO: 4)
GCAUCCGGGUUGAGGUAGUAGGUUGUAUGGUUUAGAGUUACACCCUG
GGAGUUAACUGUACAACCUUCUAGCUUUCCUUGGAGC >hsa-let-7d (miRBase Ref. No.: MI0000065)
                                        (SEQ ID NO: 5)
CCUAGGAAGAGGUAGUAGGUUGCAUAGUUUUAGGGCAGGGAUUUUGC
CCACAAGGAGGUAACUAUACGACCUGCUGCCUUUCUUAGG >hsa-let-7e (miRBase Ref. No.: MI0000066)
                                        (SEQ ID NO: 6)
CCCGGGCUGAGGUAGGAGGUUGUAUAGUUGAGGAGGACACCCAAGGA
GAUCACUAUACGGCCUCCUAGCUUUCCCCAGG >hsa-let-7f-1 (miRBase Ref. No.: MI0000067)
                                        (SEQ ID NO: 7)
UCAGAGUGAGGUAGUAGAUUGUAUAGUUGUGGGGUAGUGAUUUUACC
CUGUUCAGGAGAUAACUAUACAAUCUAUUGCCUUCCCUGA >hsa-let-7f-2 (miRBase Ref. No.: MI0000068)
                                        (SEQ ID NO: 8)
UGUGGGAUGAGGUAGUAGAUUGUAUAGUUUUAGGGUCAUACCCCAUC
UUGGAGAUAACUAUACAGUCUACUGUCUUUCCCACG >hsa-let-7g (miRBase Ref. No.: MI0000433)
                                        (SEQ ID NO: 9)
AGGCUGAGGUAGUAGUUUGUACAGUUUGAGGGUCUAUGAUACCACCC
GGUACAGGAGAUAACUGUACAGGCCACUGCCUUGCCA >hsa-let-7i (miRBase Ref. No.: MI0000434)
                                        (SEQ ID NO: 10)
CUGGCUGAGGUAGUAGUUUGUGCUGUUGGUCGGGUUGUGACAUUGCC
CGCUGUGGAGAUAACUGCGCAAGCUACUGCCUUGCUA.
```

In one embodiment, the modified miRNA comprises one or more of the following modified human sequences:

```
Let-7g (version E):
                                        (SEQ ID NO: 12)
AGGCUGAGGUAGUAGUUUGUACAGUUUGAGGGUCUAUGAUACCACCCGGU
ACAUCAGAUAACUGUACAGGCCACUGCCUUGCCA Let-7g (version I):
                                        (SEQ ID NO: 13)
AGGCUGAGGUAGUAGUUUGUACAGUUUGAGGGCGUAUGAUACCACCCGGU
ACAGGAUGCAACUGUACAGGCCACUGCCUUGCCA.
```

In other embodiments, the modified miRNA comprises one or more of the following modified human sequences:

```
Let-7g (version B)
                                        (SEQ ID NO: 14)
AGGCUGAGGUAGUAGUUUGUACAGUUUGAGGGUCUAUGAUACCACCCGGU
ACAUGAGAUAACUGUACAGGCCACUGCCUUGCCA Let-7g (version C)
                                        (SEQ ID NO: 15)
AGGCUGAGGUAGUAGUUUGUACAGUUUGAGGGUCUAUGAUACCACCCGGU
ACAGGAUAUAACUGUACAGGCCACUGCCUUGCCA Let-7g (version E)
                                        (SEQ ID NO: 16)
AGGCUGAGGUAGUAGUUUGUACAGUUUGAGGGUCUAUGAUACCACCCGGU
ACAUCAGAUAACUGUACAGGCCACUGCCUUGCCA Let-7g (version H)
                                        (SEQ ID NO: 17)
AGGCUGAGGUAGUAGUUUGUACAGUUUGAGGGCGGAUGAUACCACCCGGU
ACAUGGCGCAACUGUACAGGCCACUGCCUUGCCA Let-7g (version I)
                                        (SEQ ID NO: 18)
AGGCUGAGGUAGUAGUUUGUACAGUUUGAGGGCGUAUGAUACCACCCGGU
ACAGGAUGCAACUGUACAGGCCACUGCCUUGCCA.
```

In some embodiments, at least two of the let-7 miRNAs are used with the methods described herein. In other embodiments, at least three let-7 miRNAs are used in combination, at least 4, at least 5, at least 6, at least 7, at least 8, at least 9 or more of the let-7miRNAs recited herein are used in combination for the maturation of a cardiomyocyte.

In another embodiment, one or more modifications to a let-7 miRNA can include mutations to one or more nucleotides in the underlined, bolded regions of SEQ ID NOs: 1-10. In addition to nucleotide transposition or transversion changes, modifications and/or mutations can include insertions or deletions in the underlined, bolded regions of SEQ ID NOs: 1-10. In one embodiment, the insertion or deletion comprises a sequence less than 7 nucleotides; in other embodiments, the insertion or deletion comprises a sequence less than 6 nucleotides (nt), less than 5 nt, less than 4 nt, less than 3 nt, less than 2 nt, or comprises a single nucleotide insertion or deletion.

In one embodiment, the let-7 isoform used with the methods described herein is let-7g, and/or let-7i.

In some embodiments, the let-7 miRNA or let-7 miRNA is a pre-miRNA.

Let-7 useful in the present invention includes sequence variants of let-7 that retain at least 50% of the target gene-inhibitory function of wild type mature let-7 miRNA (SEQ ID NO: 1). Let-7 variants generally fall into one or more of three classes: substitution, insertional or deletional variants. Insertions include 5' and/or 3' terminal fusions as well as intrasequence insertions of single or multiple residues. Insertions can also be introduced within the mature sequence of let-7. Intrasequence insertions ordinarily will be smaller insertions than those at the 5' or 3' terminus, on the order of 1 to 4 or 1-10 residues. It is understood that the variants, substitutions, insertions or deletions of residues will not result in a deleterious effect on the function of the variant in its ability to bind to, and inhibit the expression of genes comprising let-7 target sequence 5'-AACTATA-CAACCTACTACCTCA-3' (SEQ ID NO: 11), and preferably the substitution, insertional or deletional variants will have increased binding affinity for the let-7 target sequence 5'-AACTATACAACCTACTACCTCA-3' (SEQ ID NO: 11), and thus increased gene silencing efficacy of the target gene as compared to wild type let-7 corresponding to SEQ ID NO:1. Alternatively, as discussed below, variants can have improved properties such as avoiding endogenous mechanisms that would otherwise inhibit or limit miRNA function, or be processed more efficiently to active form.

Substitutional variants are those in which at least one residue has been removed and a different residue inserted in its place. Insertional sequence variants of let-7 are those in which one or more residues are introduced into a predetermined site in the target let-7 miRNA. Most commonly, insertional variants are fusions of nucleic acids at the 5' or 3' terminus of let-7. Deletion variants are characterized by the removal of one or more residues from the let-7 RNA sequence. These variants ordinarily are prepared by site specific mutagenesis of nucleotides in the DNA encoding let-7, thereby producing DNA encoding the variant, and thereafter expressing the DNA in recombinant cell culture. However, variant let-7 fragments can be conveniently prepared by in vitro synthesis. The variants typically exhibit the same qualitative biological activity as the naturally-occurring analogue, although variants also are selected in order to modify the characteristics of let-7.

While the site for introducing a sequence variation is selected, the mutation per se need not be predetermined. Thus, if the nucleotide at a site to be mutated is a G, mutation to any of A, T, or C can be made with the expectation that the change will modify function of the products; while, in this example, one of A, T, or C may be optimal, it is to be expected that any of them will be beneficial. Of course, in order to optimize the performance of a mutation at a given site, random mutagenesis can be conducted at the target region and the expressed let-7 variants screened for the optimal combination of desired activity. Techniques for making substitution mutations at predetermined sites in DNA having a known sequence are well known. Nucleotide substitutions are typically of single residues; insertions can be on the order of about 1 to 10 residues; and deletions can range from about 1 to 30 residues. Deletions or insertions preferably are made in adjacent pairs; i.e., a deletion of 2 residues or insertion of 2 residues.

Substitutions, deletion, insertions or any combination thereof can be combined to arrive at a final construct. Changes can be made to increase the activity of the miRNA, to increase its biological stability or half-life, and the like. All such modifications to the nucleotide sequences encoding such miRNA are encompassed.

In some embodiments, the size range of the mature let-7 miRNA can be from 20-21 nucleotides, while the size of the let-7 pri-miRNA or let-7 pre-miRNA can be larger.

Suitable nucleic acids for use in the methods described herein include, but are not limited to, let-7 pri-miRNA, let-7 pre-miRNA, mature let-7 miRNA or fragments of variants thereof that retain the biological activity of let-7 miRNA and DNA encoding let-7 pri-miRNA, let-7 pre-miRNA, mature let-7 miRNA, fragments or variants thereof, or DNA encoding regulatory elements of let-7 miRNA.

In one embodiment, the let-7 miRNA comprises one or more mutations, insertions, or deletions that render the let-7 miRNA insensitive to inhibition by LIN28. In another embodiment, the modification to render the miRNA resistant to LIN28 binding comprises a modification of the miRNA sequence at a LIN28 binding site comprising the sequence GGAG. In one embodiment, modified versions of the hsa-let-7g sequence are designed by making mutations in the terminal loop region of the hsa-let-7g sequence in order to disrupt the GGAG motif, which has been identified as a LIN28 binding site (Nam et al. 2011). Additional mutations can be designed to make the hairpin structurally and thermodynamically as similar to the wild type hsa-let-7g as possible, making them different from previously published modified versions of let-7g, which were not thermodynamically optimized.

Modifications to miRNA to Enhance Processing

MicroRNAs (miRNA which also include isomiRs) are a group of short, non-coding RNAs that bind target mRNAs to either inhibit their translation or reduce their stability. miRNAs are transcribed in the nucleus as part of a primary microRNA (pri-miRNA). The length of pri-miRNAs is highly variable, ranging from approximately 200 nucleotides up to several thousand nucleotides (nt). pri-miRNAs are cleaved by the cellular Microprocessor complex, which consists of several components, principally Drosha and DGCR8. Drosha and DGCR8 cooperatively bind pri-miRNA, and Drosha cleaves the primary pri-miRNA transcript at approximately 11 base pairs from the base of the stem-loop, liberating a structure known as the precursor microRNA (pre-miRNA).

pre-miRNA is typically about 60-70 nt in length and forms a frequently mismatched hairpin structure with a 2 nucleotide 3' overhang. The pre-miRNA is transported from the nucleus to the cytoplasm and is subsequently cleaved by the enzyme Dicer with its cofactor trans-activator RNA (tar)-binding protein (TRBP). Dicer binds the 3'-overhang and cleaves the pre-miRNA approximately 22 nt from the Drosha-cutting site to remove the terminal loop resulting in an imperfect ~22 nt miRNA/miRNA* duplex. The miRNA enters the RNA-induced silencing complex (RISC), whereas the miRNA* strand is degraded. While the Drosha and Dicer processing mechanisms are described in relation to miRNA, the same mechanisms can process various other RNA types as well including mRNA.

RNAs, including miRNAs, are involved with the onset of various diseases, immunoregulation, neural growth and stem cell renewal and maintenance. RNA levels can be regulated in several ways. For example, pri-miRNA transcription is regulated by common DNA transcription factors, e.g., c-Myc. The Microprocessor complex contains several components besides Drosha and DGCR8, such as the DEAD-box helicases p68 and p72, which have been proposed to stabilize the Microprocessor complex. Other components of the Microprocessor include SMAD proteins which have been found to selectively upregulate certain RNAs, e.g., mir-21. The DGCR8 mRNA has stem loop structures that can be cleaved by the Microprocessor, accordingly giving DGCR8 a self-regulating mechanism.

RNA levels can be regulated in several ways. For example, pri-miRNA transcription is regulated by common transcription factors such as c-Myc. The Microprocessor complex contains several components besides Drosha and DGCR8, such as the DEAD-box helicases p68 and p72, which have been proposed to stabilize the Microprocessor complex. Other components of the Microprocessor include SMAD proteins which have been found to selectively upregulate certain RNAs such as mir-21. The DGCR8 mRNA has stem loop structures that can be cleaved by the Microprocessor, accordingly giving DGCR8 a self-regulating mechanism.

Decreasing Drosha expression leads to heterogeneous changes in the expression of RNA. The global but non-uniform impact of Drosha knockdown on RNA expression shows that RNAs are not processed by Drosha at equal rates. Non-uniform processing effects indicate that there is a structural relationship between the Microprocessor and the RNAs it cleaves, and any other associated proteins, which could explain the effects of Drosha-knockdown on expression of specific RNAs.

Particular proteins interact with the Microprocessor and/or RNAs to promote or inhibit processing of RNAs. Without being bound by a particular theory, it is possible that protein-based effects explain much of the variation seen in the Drosha knockdown datasets. However, such specific interactions are considered as part of a complex feed-back mechanism triggered by Drosha-knockdown. In an effort to quantify broad, global mechanisms, which control RNA biogenesis, the genomic origin of 220 miRNAs was first investigated (some miRNAs skip Drosha-processing). Intronic miRNAs were not expressed differently from intergenic miRNAs.

Thus, miRNAs can be designed to enhance or repress processing of the endogenous form of the RNA by removing or introducing mis-matches into nucleotide (nt) positions 5 and/or 9-12 from the Drosha cutting site. Mis-matches are removed to enhance processing, and mis-matches are introduced to repress processing. Mis-matches are removed by modifying the nucleotide opposite the mis-match in the stem structure to be complementary; removal of mismatches also includes removal of extra, non-complementary nucleotides, e.g., those nucleotides that form a non-hybridized bulge in the stem at the sites noted. Conversely, mis-matches are introduced by placing a non-complementary nucleotide opposite a given nucleotide in the stem structure, and introduction of a mismatch can also include the insertion of one or more (e.g., 2, 3) extra non-complementary nucleotides, so as to form a non-hybridized bulge in the stem relative to the wild-type molecule.

Within the context of the designed artificial miRNAs, the term "miRNA" refers to any non-endogenous microRNA molecule that can be involved in RNA-based gene regulation. Accordingly, "miRNA" refers to an RNA capable of modulating the productive utilization of mRNA. The term "mRNA" refers to a nucleic acid transcribed from a gene from which a polypeptide is translated, and can include non-translated regions such as a 5'UTR and/or a 3'UTR. An miRNA can include a nucleotide sequence that is completely or partially complementary to any sequence of an mRNA molecule, including translated regions, the 5'UTR, the 3'UTR, and sequences that include both a translated region and a portion of either 5'UTR or 3'UTR. An miRNA can also comprise a nucleotide sequence that is complementary to a region of an mRNA molecule spanning the start codon or the stop codon.

The artificially-designed RNA disclosed herein can include RNA flanking sequences. "RNA flanking sequences" refer to nucleotide sequences including RNA processing elements that flank one or both sides of the Drosha cutting site.

"miRNA flanking sequence" refers to nucleotide sequences including miRNA processing elements. miRNA processing elements are the minimal nucleic acid sequences which contribute to the production of mature miRNA from precursor miRNA. Often these elements are located within a 40 nucleotide sequence that flanks a miRNA stem-loop structure. In some instances the miRNA processing elements are found within a stretch of nucleotide sequences of between 5 and 4,000 nucleotides in length that flank a miRNA stem-loop structure.

Thus, in some embodiments the flanking sequences are 5-4,000 nucleotides in length. As a result, the length of the precursor molecule may be, in some instances at least about 150 nucleotides or 270 nucleotides in length. The total length of the precursor molecule, however, may be greater or less than these values. In other embodiments the minimal length of the miRNA flanking sequence is 10, 20, 30, 40, 50, 60, 70, 80, 90, 100, 150, 200 and any integer there between. In other embodiments the maximal length of the miRNA flanking sequence is 2000, 2100, 2200, 2300, 2400, 2500, 2600, 2700, 2800, 2900, 3000, 3100, 3200, 3300, 3400, 3500, 3600, 3700, 3800, 3900 4000 and any integer there between. In other embodiments, the flanking sequence is between 25-500 nucleotides, between 25-400 nt, between 25-300 nt, between 25-200 nt, between 25-100 nt, between 25-50 nt, between 50-500 nt, between 75-500 nt, between 100-500 nt, between 200-500 nt, between 250-500 nt, between 300-500 nt, between 350-500 nt, between 400-500 nt, between 450-500 nt, between 75-300 nt, between 100-300 nt, between 100-200 nt, or any range in between.

The miRNA flanking sequences may be native/endogenous miRNA flanking sequences or artificial miRNA flanking sequences. A native/endogenous miRNA flanking sequence is a nucleotide sequence that is ordinarily associated in naturally existing systems with miRNA sequences, i.e., these sequences are found within the genomic sequences surrounding the minimal miRNA hairpin in vivo. Artificial miRNA flanking sequences are nucleotide sequences that are not found to be flanking to miRNA sequences in naturally existing systems. The artificial miRNA flanking sequences may be flanking sequences found naturally in the context of other miRNA sequences. Alternatively they may be composed of minimal miRNA processing elements which are found within naturally occurring flanking sequences and inserted into other random nucleic acid sequences that do not naturally occur as flanking sequences or only partially occur as natural flanking sequences.

The miRNA flanking sequences within the precursor miRNA molecule can flank one or both sides of the stem-loop structure encompassing the miRNA sequence. Thus, one end (i.e., 5') of the stem-loop structure can be adjacent to a single flanking sequence and the other end (i.e., 3') of the stem-loop structure cannot be adjacent to a flanking sequence. Particular structures have flanking sequences on both ends of the stem-loop structure. The flanking sequences may be directly adjacent to one or both ends of the stem-loop structure or may be connected to the stem-loop structure through a linker, additional nucleotides or other molecules.

In some instances the pri-miRNA molecule can include more than one stem-loop structure. The multiple stem-loop structures can be linked to one another through a linker, such as, for example, a nucleic acid linker or by a miRNA flanking sequence or other molecule or some combination thereof.

In particular embodiments, useful interfering RNAs can be designed with a number of software programs, e.g., the OligoEngine RNA design tool. RNAs within this context can be about, e.g., 19-33 base pairs in length for the double-stranded portion. In some embodiments, the RNAs are hairpin RNAs having an about 19-33 bp stem and an about 4-34 nucleotide loop. Particular RNAs are highly specific for a region of a target gene and may comprise 19-33 bp fragments of a target gene mRNA that has at least one, at least two, or at least three, bp mismatches with a nontargeted gene-related sequence. In some embodiments, the RNAs do not bind to RNAs having more than 3 mismatches with the target region.

The artificial RNAs disclosed herein can be formed from a polymer of nucleotides (i.e., molecules comprising a sugar (e.g., ribose) linked to a phosphate group and to an exchangeable organic base, which is either a substituted pyrimidine (e.g., cytosine (C), or uracil (U)) or a substituted purine (e.g., adenine (A) or guanine (G)). As used herein, the term nucleotides also can include polynucleosides (i.e., a polynucleotide minus the phosphate) and any other organic base containing polymer.

The artificial miRNAs can also encompass nucleotides with substitutions or modifications, such as in the bases and/or sugars. Modified bases include any base that is chemically distinct from the naturally occurring bases typically found in RNA (C, G, A, and U), but which share basic chemical structures with these naturally occurring bases. The modifications can improve, e.g., stability, target binding affinity, or target specificity, among other effects. The modified nucleotide base may be, for example, dihydrouracil, pseudouracil, 2-thiouracil, 4-thiouracil, 5-aminouracil, 5-(C1-C6)-alkyluracil, 5-(C2-C6)-alkenyluracil, 5-(C2-C6)-alkynyluracil, 5-(hydroxymethyl)uracil, 5-chlorouracil, 5-fluorouracil, 5-bromouracil, 5-hydroxycytosine, 5-(C1-C6)-alkylcytosine, 5-(C2-C6)-alkenylcytosine, 5-(C2-C6)-alkynylcytosine, 5-chlorocytosine, 5-fluorocytosine, 5-bromocytosine, N2-dimethylguanine, 2,4-diamino-purine, 8-azapurine, a substituted 7-deazapurine, 7-deaza-7-substituted and/or 7-deaza-8-substituted purine, 5-hydroxymethylcytosine, N4-alkylcytosine, N4-ethylcytosine, 5-hydroxydeoxycytidine, 5-hydroxymethyldeoxycytidine, N4-alkyldeoxycytidine, N4-ethyldeoxycytidine, 6-th iodeoxyguanosine, deoxyribonucleosides of nitropyrrole, C5-propynylpyrimidine, diaminopurine, 2,6-diaminopurine, inosine, 5-methylcytosine, 2-aminopurine, 2-amino-6-chloropurine, hypoxanthine or other modifications of a natural nucleoside bases.

The artificial RNAs can also encompass various chemical modifications and substitutions, in comparison to natural RNA involving phosphodiester internucleotide bridges and/or 3-D-ribose units. Replacing a phosphodiester bridge located at the 3' and/or the 5' end of a nucleotide can make artificial RNAs disclosed herein more resistant to degradation (i.e., are stabilized). Exemplary modified internucleotide bridges include phosphorothioate, phosphorodithioate, NR1R2-phosphoramidate, boranophosphate, a-hydroxybenzyl phosphonate, phosphate-(C1-021)-0-alkyl ester, phosphate-[(C6-C12)aryl-(C1-021)-0-alkyl]ester, (C1-C8)alkyl-phosphonate and/or (C6-12)arylphosphonate bridges, (C7-C12)-a-hydroxymethyl-aryl, wherein (C6-C12)aryl, (C6-C20)aryl and (C6-C14)aryl are optionally substituted by halogen, alkyl, alkoxy, nitro, cyano, and where R1 and R2 are, independently of each other, hydrogen, (C1-C18)-alkyl, (C6-C20)-aryl, (C6-C14)-aryl-(C1-C8)-alkyl, hydrogen, (C1-C8)-alkyl, (C1-C4)-alkyl and/or methoxyethyl, or R1 and R2 form, together with the nitrogen atom carrying them, a 5-6-membered heterocyclic ring which can additionally contain a further heteroatom from the group O, S and N. Dephospho bridges can also be used. Dephospho bridges are described, for example, in Uhlmann and Peyman in "Methods in Molecular Biology", Vol. 20, "Protocols for Oligonucleotides and Analogs", Agrawal, Ed., Humana Press, Totowa 1993, Chapter 16, pp. 355 if). Exemplary dephospho bridges include formacetal, 3'-thioformacetal, methylhydroxylamine, oxime, methylenedimethyl-hydrazo, dimethylenesulfone and/or silyl groups.

Beta-ribose units can be replaced by modified sugar units such as 3-D-ribose, 6-D-2'-deoxyribose, L-2'-deoxyribose, 2'-F-2'-deoxyribose, 2'-F-arabinose, 2'-0-(C1-C6)alkyl-ribose, 2'-0-(C1-C6)alkyl-ribose, 2'-0-methyl ribose, 2'-0-(C2-C6)alkenyl-ribose, 2'-[0-(C1-C6)alkyl-0-(C1-C6)alkyl]-ribose, 2'-NH2-2'-deoxyribose, 6-D-xylo-furanose, a-arabinofuranose, 2,4-dideoxy-6-D-erythro-hexo-pyranose or carbocyclic and/or open-chain sugar analogs and/or bicyclosugar analogs.

Sugar phosphate units from the sugar phosphate backbone can also be replaced by other units such as "morpholino-derivative" oligomers (see, for example, Stirchak et al. (1989) Nucleic Acids Res 17:6129-41); polyamide nucleic acids (PNA; see, for example, Nielsen et al. (1994) Bioconjug Chem 5:3-7) such as by 2-aminoethylglycine; peptide nucleic acids with phosphate groups (PHONA); locked nucleic acids (LNA); and/or nucleotides having backbone sections with alkyl linkers or amino linkers. Alkyl linkers can be branched or unbranched, substituted or unsubstituted, and chirally pure or a racemic mixture.

Artificial RNAs disclosed herein can also be conjugated to lipophilic or lipid moieties. Exemplary lipophilic or lipid moieties include cholesteryls, modified cholesteryls, cholesterol derivatives, reduced cholesterols, substituted cholesterols, cholestans, C1-6 alkyl chains, cholic acid, taurocholic acid, deoxycholate, oleyl litocholic acid, oleoyl cholenic acid, glycolipids, phospholipids, sphingolipids, isoprenoids, saturated fatty acids, unsaturated fatty acids or fatty acid esters. The lipophilic or lipid moieties can be attached via any suitable direct or indirect linkage such as, without limitation, by an ester or an amide. Linkages can include spacer moieties, for example one or more nucleotide residues, oligoethyleneglycol, triethyleneglycol, hexaethylenegylcol or an alkane-diol, such as butanediol.

Artificial RNAs disclosed herein can also be conjugated to Nuclear Localization Signals (NLS). "Nuclear localization signals" are sequences (in some embodiments amino acid sequences) that can direct artificial RNAs in the cytoplasm of a cell across the nuclear membrane and into the nucleus of the cell. A nuclear localization signal can also target the exterior surface of a cell. Thus, a single nuclear localization signal can direct the artificial RNA with which it is associated to the exterior of a cell and to the nucleus of a cell. Nuclear localization signals are generally basic, comprise a short sequence of 4-8 amino acids and are typically rich in lysine and arginine residues while also often comprising proline residues.

While particular RNA sequences are described, the current disclosure also encompasses RNA sequences that hybridize with the specifically disclosed RNA sequences. An RNA sequence "hybridizes" to another RNA sequence when a single stranded form of the RNA sequence anneals to the other RNA sequence under the appropriate conditions of temperature and solution ionic strength. Hybridization and washing conditions are well known and exemplified in Sambrook, J., Fritsch, E. F. and Maniatis, T. Molecular Cloning: A Laboratory Manual, Second Ed., Cold Spring Harbor Laboratory Press, Cold Spring Harbor (1989), particularly Chapter 11 and Table 11.1 therein (incorporated by reference herein for its teachings regarding the same). The conditions of temperature and ionic strength determine the "stringency" of the hybridization. Stringency conditions can be adjusted to screen for moderately similar RNA sequences to highly similar RNA sequences. Post-hybridization washes determine stringency conditions. One set of hybridization conditions to demonstrate that RNA sequences hybridize uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. Stringent conditions use higher temperatures in which the washes are identical to those above except for the temperature of the final two 30 min washes in 0.2×SSC, 0.5% SDS is increased to 60° C. Highly stringent conditions use two final washes in 0.1SSC, 0.1% SDS at 65° C. Those of ordinary skill in the art will recognize that these temperature and wash solution salt concentrations may be adjusted as necessary according to factors such as the length of the tested RNA sequences.

Additional methods contemplated for generating modified miRNAs for use in the methods and compositions described herein can be found in PCT/US13/76256, which is incorporated herein by reference in its entirety.

Cardiomyocyte Metabolism

The fetal heart derives nearly all of the energy needed for the maintenance of basal contractile function and ionic balance from anaerobic glycolysis of glucose to pyruvate. In contrast, the adult heart derives 60-70% of its energy from fatty acid oxidation, with glucose oxidation and lactate oxidation contributing a majority of the remainder of the energy requirements. There is a profound switch in cardiac substrate metabolism during the fetal transition period, when oxidative metabolic pathways take over from glycolysis as the main source of energy.

This phenomenon is also observed in cardiomyocytes in culture. Typically, cardiomyocytes derived from stem cells or cultured in vitro comprise a metabolic phenotype similar to the fetal heart, with a preference for glycolysis as the main source of energy. The methods and compositions provided herein permit the maturation of cultured cardiomyocytes to a mature phenotype in which the cells preferentially utilize fatty acids as their main source of energy. Since the metabolism of fatty acids through β-oxidation requires the presence of oxygen, one can easily determine the timing and/or degree of maturation of a cardiomyocyte culture by measuring the mitochondrial respiratory capacity, among other parameters. Many of these parameters can be assessed by providing one or more energy substrates and using a metabolic flux assay, such as a SEAHORSE™ metabolic flux assay.

In one embodiment, the oxygen consumption rate (OCR) can be determined for the cultured cells. The OCR is a metabolic parameter representing mitochondrial respiration levels. Typically, cells are contacted with oligomycin to uncouple the electron transport chain from ATP synthesis and then the culture is contacted with a proton gradient discharger (e.g., carbonyl cyanide 4-(trifluoromethoxy)phenylhydrazone (FCCP). The maximum respiratory capacity is then measured in cells. While increased mitochondrial respiration can be due, in part, to an increase in mitochondrial number, one of skill in the art can also normalize the respiratory capacity to the mitochondrial genome copy number.

Another parameter that can be assessed is the extracellular acidification rate (ECAR), which is a measure of glycolysis. Glycolysis converts glucose to two molecules of pyruvate and in the process generates two protons, which are extruded from the cell under anaerobic conditions. Thus, the extracellular acidification rate (i.e., extracellular proton accumulation rate) can be used to assess the degree of energy substrate metabolism through the glycolytic pathway.

Pharmaceutically Acceptable Carriers

The methods of administering cardiomyocytes having a mature phenotype to a subject as described herein involve the use of therapeutic compositions comprising such cardiomyocytes. Therapeutic compositions contain a physiologically tolerable carrier together with the cell composition and optionally at least one additional bioactive agent as described herein, dissolved or dispersed therein as an active ingredient. In a preferred embodiment, the therapeutic composition is not substantially immunogenic when administered to a mammal or human patient for therapeutic purposes, unless so desired. As used herein, the terms "pharmaceutically acceptable", "physiologically tolerable" and grammatical variations thereof, as they refer to compositions, carriers, diluents and reagents, are used interchangeably and represent that the materials are capable of administration to, into, or upon a mammal without the production of undesirable physiological effects such as nausea, dizziness, gastric upset, transplant rejection, allergic reaction, and the like. The preparation of a composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared.

In general, the cardiomyocytes described herein are administered as a suspension with a pharmaceutically acceptable carrier. One of skill in the art will recognize that a pharmaceutically acceptable carrier to be used in a cell composition will not include buffers, compounds, cryopreservation agents, preservatives, or other agents in amounts that substantially interfere with the viability of the cells to be delivered to the subject. A formulation comprising cells can include e.g., osmotic buffers that permit cell membrane integrity to be maintained, and optionally, nutrients to maintain cell viability or enhance engraftment upon administration. Such formulations and suspensions are known to those of skill in the art and/or can be adapted for use with the cardiomyocytes as described herein using routine experimentation.

A cell composition can also be emulsified or presented as a liposome composition, provided that the emulsification procedure does not adversely affect cell viability. The cells and any other active ingredient can be mixed with excipients which are pharmaceutically acceptable and compatible with the active ingredient and in amounts suitable for use in the therapeutic methods described herein.

Additional agents included in a cell composition as described herein can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active compound used in the cell compositions as described herein that is effective in the treatment of a particular disorder or condition will depend on the nature of the disorder or condition, and can be determined by standard clinical techniques.

When treating myocardial ischemia the desired response is the symptomatic treatment of the consequences of the disease. This can involve only the partial improvement of the symptomatic consequences of the disease, although more preferably, it involves improvement of the symptomatic consequences of the disease. Efficacy of treatment can be monitored by routine methods. More particularly improvements in myocardial ischemia can be monitored by any one of the following indicia: tolerance to exercise and physical stress; exercise stress ECG testing; heart function on echocardiography or ECG signs of ischemia and cardiac MRI to provide details of cardiac structure.

Treatment of Cardiovascular Disease

The heart comprises cardiac muscle which forms the walls of the heart and is an involuntary striated muscle which is adapted to be resistant to fatigue. Failure to supply sufficient oxygen to essential organs results in a condition called ischemia which usually is caused by a critical coronary artery obstruction, but can be irreversible. Myocardial ischemia is a condition that can be asymptomatic until such time as the supply of oxygen to cardiac muscle becomes restricted to the extent that the muscle fails and a heart attack occurs.

Ischemic heart diseases (IHD) are characterized by reduced blood supply to the heart muscle, causing infarction and cell death of the affected area. Following birth, cardiomyocytes lose their capacity to divide, thus prohibiting self-regeneration of the heart after injury. Upon myocardial infarction, scar tissue develops over the damaged regions reducing the contractile function of the heart, leading to ventricle wall thinning and ultimately heart failure.

Treatment of damaged myocardium requires replacement of the scar tissue with functioning cardiac muscle tissue. However, despite recent advancements in the area of cell tissue engineering, success rates are low and the requirements for developing functioning myocardial tissue are meticulous. Selection of the right cell population, the establishment of scaffold-like structures mimicking native tissue matrices, construction of tissue patches of desired size and enabling vascularizations are obstacles for engineering functional tissue grafts. This can be due, in part, to the use of cardiomyocyte populations comprising a fetal-like phenotype rather than using mature cardiomyocytes that have a phenotype that matches the existing contractile cells in the damaged heart.

Cell based therapy includes the administration of cells to the diseased heart in order to reestablish, at the desired location, a structurally and functionally intact unit. In some embodiments, cells can be transplanted by forming a cardiac-like tissue structure, which is promoted by seeding cells onto a porous, fibrous or hydrogel scaffold. U.S. Pat. No. 7,396,537 discloses a composition of a cardiac patch comprising different layers using collagen hydrogel supported by an intermediate scaffolding layer formed of biodegradable co-polymers of glycolic and/or lactic acid attached to a reinforcement layer of non-biodegradable support material. Others disclose devices made of support scaffolds and cell sheets; see US 2006/0153815. Mechanical stability and elasticity was addressed in US 2004/017712 by developing a tubular artificial tissue scaffold of high elasticity having aligned biofibrils seeded with cells. Besides using scaffolds, techniques have also been developed to engineer scaffold free tissues, composed only of cells and the matrix they secrete, circumventing common problems occurring when using scaffolds, as residual polymer fragments can interfere with the cell organization and an inherent weakness of tissue engineered vessel.

Essentially any cardiac disease, disorder or injury can be treated using the methods and compositions described herein. It is preferred that the cardiac disease, disorder or injury is associated with ischemia, loss of contractile function, loss of myocytes, or formation of scar tissue, such that administration of mature cardiomyocytes will replace lost cardiac tissue and/or function. Examples of cardiac diseases, disorders, or injuries include, but are not limited to, acute myocardial infarction, ischemia/reperfusion injury, autophagy, cardiomyopathy, dilated cardiomyopathy, heart failure, restenosis, cardiac apoptosis, or cardiac necrosis. In one embodiment, coronary heart diseases can be treated with mature cardiomyocytes, as described herein. In one embodiment, the coronary heart disease is Arrhythmogenic right ventricular dysplasia (ARVD) or Muscular dystrophy associated cardiomyopathy (MD-CM).

Administration and Efficacy

Provided herein are methods for treating a cardiac disease, a cardiac disorder, or a cardiac injury comprising administering mature cardiomyocytes to a subject in need thereof.

As used herein, the terms "administering," "introducing" and "transplanting" are used interchangeably in the context of the placement of cells, e.g., mature cardiomyocytes, as described herein into a subject, by a method or route which results in at least partial localization of the introduced cells at a desired site, such as a site of injury or repair, such that a desired effect(s) is produced. The cells e.g., mature cardiomyocytes can be implanted directly into damaged cardiac tissue, or alternatively be administered by any appropriate route which results in delivery to a desired location in the subject where at least a portion of the implanted cells or components of the cells remain viable. The period of viability of the cells after administration to a subject can be as short as a few hours, e.g., twenty-four hours, to a few days, to as long as several years or more, i.e., long-term engraftment.

In one embodiment, mature cardiomyocytes are administered to a subject having detectable cardiac disease. Measured or measurable parameters include clinically detectable markers of disease, for example, elevated or depressed levels of a clinical or biological marker, as well as parameters related to a clinically accepted scale of symptoms or markers for a disease or disorder. It will be understood, however, that the total usage of the compositions and formulations as disclosed herein will be decided by the attending physician within the scope of sound medical judgment. The exact amount required will vary depending on factors such as the type of disease being treated.

The term "effective amount" as used herein refers to the amount of a population of mature cardiomyocytes needed to alleviate at least one or more symptoms of the cardiac injury or the cardiac disease or disorder, and relates to a sufficient amount of a composition to provide the desired effect, e.g., treat a subject having damaged cardiac tissue. The term "therapeutically effective amount" therefore refers to an amount of mature cardiomyocytes or a composition comprising mature cardiomyocytes that is sufficient to promote a particular effect when administered to a typical subject, such as one who has or is at risk for a cardiac disease or disorder. An effective amount as used herein would also include an amount sufficient to prevent or delay the development of a symptom of the disease, alter the course of a symptom disease (for example but not limited to, slow the progression of a symptom of the disease), or reverse a symptom of the disease. It is understood that for any given case, an appropriate "effective amount" can be determined by one of ordinary skill in the art using routine experimentation.

In some embodiments, the subject is first diagnosed as having a disease or disorder affecting the cardiac tissue prior to administering the cells according to the methods described herein (e.g., as a result of an acute myocardial infarction). In some embodiments, the subject is first diagnosed as being at risk of developing cardiac disease or disorder prior to administering the cells (e.g., a subject having early symptoms of congestive heart failure).

For use in the various aspects described herein, an effective amount of mature cardiomyocytes, comprises at least $10^5$ mature cardiomyocytes, at least $5 \times 10^6$ mature cardiomyocytes, at least $10^6$ mature cardiomyocytes, at least $5 \times 10^6$ mature cardiomyocytes, at least $10^7$ mature cardiomyocytes, at least $2 \times 10^7$ mature cardiomyocytes, at least $3 \times 10^7$ mature cardiomyocytes, at least $4 \times 10^7$ mature cardiomyocytes, at least $5 \times 10^7$ mature cardiomyocytes, at least $6 \times 10^7$ mature cardiomyocytes, at least $7 \times 10^7$ mature cardiomyocytes, at least $8 \times 10^7$ mature cardiomyocytes, at least $9 \times 10^7$ mature cardiomyocytes, at least $1 \times 10^8$ mature cardiomyocytes, at least $2 \times 10^8$ mature cardiomyocytes, at least $3 \times 10^8$ mature cardiomyocytes, at least $4 \times 10^8$ mature cardiomyocytes, at least $5 \times 10^8$ mature cardiomyocytes, at least $6 \times 10^8$ mature cardiomyocytes, at least $7 \times 10^8$ mature cardiomyocytes, at least $8 \times 10^8$ mature cardiomyocytes, at least $9 \times 10^8$ mature cardiomyocytes, at least $1 \times 10^9$ mature cardiomyocytes, at least $2 \times 10^9$ mature cardiomyocytes, at least $3 \times 10^9$ mature cardiomyocytes, at least $4 \times 10^9$ mature cardiomyocytes, at least $5 \times 10^9$ mature cardiomyocytes, at least $6 \times 10^9$ mature cardiomyocytes, at least $7 \times 10^9$ mature cardiomyocytes, at least $8 \times 10^9$ mature cardiomyocytes, at least $9 \times 10^9$ mature cardiomyocytes, at least $1 \times 10^{10}$ mature cardiomyocytes, at least $2 \times 10^{10}$ mature cardiomyocytes, at least $3 \times 10^{10}$ mature cardiomyocytes, at least $4 \times 10^{10}$ mature cardiomyocytes, at least $5 \times 10^{10}$ mature cardiomyocytes, at least $6 \times 10^{10}$ mature cardiomyocytes, at least $7 \times 10^{10}$ mature cardiomyocytes, at least $8 \times 10^{10}$ mature cardiomyocytes, at least $9 \times 10^{10}$ mature cardiomyocytes, or multiples thereof. The mature cardiomyocytes can be derived from one or more donors, or can be obtained from an autologous source. In some embodiments of the aspects described herein, the cardiac progenitor cells are expanded in culture prior to differentiation to mature cardiomyocytes and administration to a subject in need thereof.

Exemplary modes of administration for use in the methods described herein include, but are not limited to, injection, intracardiac infusion, and implantation (with or without a scaffold material). "Injection" includes, without limitation, intravenous, intramuscular, and intraarterial. The phrases "parenteral administration" and "administered parenterally" as used herein, refer to modes of administration other than enteral and topical administration, usually by injection, and includes, without limitation, intravenous, intraperitoneal, intramuscular, intraarterial, intradermal, transtracheal, and subcutaneous administration.

In some embodiments, an effective amount of mature cardiomyocytes is administered to a subject by systemic administration, such as intravenous administration.

The phrases "systemic administration," "administered systemically", "peripheral administration" and "administered peripherally" as used herein refer to the administration of a population of mature cardiomyocytes other than directly into a target site, tissue, or organ, such as the heart, such that it enters, instead, the subject's circulatory system and, thus, is subject to metabolism and other like processes.

In some embodiments, additional agents to aid in treatment of the subject can be administered before or following treatment with the mature cardiomyocytes described herein. Such additional agents can be used to prepare the cardiac tissue for administration of the mature cardiomyocytes. Alternatively the additional agents can be administered after the mature cardiomyocytes to support the engraftment and growth of the administered cell in the damaged heart.

The efficacy of treatment can be determined by the skilled clinician. However, a treatment is considered "effective treatment," as the term is used herein, if any one or all of the symptoms, or other clinically accepted symptoms or markers of cardiac disease, cardiac injury and/or a cardiac disorder are reduced, e.g., by at least 10% following treatment with a composition comprising mature cardiomyocytes as described herein. Methods of measuring these indicators are known to those of skill in the art and/or described herein.

Indicators of cardiac disease or cardiac disorder, or cardiac injury include functional indicators, e.g., measurement of left ventricular end diastolic function (LVEDF), left ventricular end diastolic pressure (LVEDP), blood pressure, echocardiographic mapping etc.), as well as biochemical indicators.

Scaffold Compositions

Biocompatible synthetic, natural, as well as semi-synthetic polymers, can be used for synthesizing polymeric particles that can be used as a scaffold material. In general, for the practice of the methods described herein, it is preferable that a scaffold biodegrades such that the mature cardiomyocytes can be isolated from the polymer prior to implantation or such that the scaffold degrades over time in a subject and does not require removal. Thus, in one embodiment, the scaffold provides a temporary structure for growth and/or delivery of mature cardiomyocytes to a subject in need thereof. In some embodiments, the scaffold is contractile in nature, for example, can contract and lengthen with every heartbeat. In some embodiments, the scaffold permits mature cardiomyocytes to be grown in a shape suitable for transplantation or administration into a subject in need thereof, thereby permitting removal of the scaffold prior to implantation and reducing the risk of rejection or allergic response initiated by the scaffold itself.

Examples of polymers which can be used include natural and synthetic polymers, although synthetic polymers are preferred for reproducibility and controlled release kinetics. Synthetic polymers that can be used include biodegradable polymers such as poly(lactide) (PLA), poly(glycolic acid) (PGA), poly(lactide-co-glycolide) (PLGA), and other polyhydroxyacids, poly(caprolactone), polycarbonates, polyamides, polyanhydrides, polyphosphazene, polyamino acids, polyortho esters, polyacetals, polycyanoacrylates and biodegradable polyurethanes; non-biodegradable polymers such as polyacrylates, ethylene-vinyl acetate polymers and other acyl-substituted cellulose acetates and derivatives thereof; polyurethanes, polystyrenes, polyvinyl chloride, polyvinyl fluoride, poly(vinyl imidazole), chlorosulphonated polyolefins, and polyethylene oxide. Examples of biodegradable natural polymers include proteins such as albumin, collagen, fibrin, silk, synthetic polyamino acids and prolamines; polysaccharides such as alginate, heparin; and other naturally occurring biodegradable polymers of sugar units. Alternately, combinations of the aforementioned polymers can be used.

PLA, PGA and PLA/PGA copolymers are particularly useful for forming biodegradable scaffolds. PLA polymers are usually prepared from the cyclic esters of lactic acids. Both L(+) and D(−) forms of lactic acid can be used to prepare the PLA polymers, as well as the optically inactive DL-lactic acid mixture of D(−) and L(+) lactic acids. Methods of preparing polylactides are well documented in the patent literature. The following U.S. Patents, the teachings of which are hereby incorporated by reference, describe in detail suitable polylactides, their properties and their preparation: U.S. Pat. No. 1,995,970 to Dorough; U.S. Pat. No. 2,703,316 to Schneider; U.S. Pat. No. 2,758,987 to Salzberg; U.S. Pat. No. 2,951,828 to Zeile; U.S. Pat. No. 2,676,945 to Higgins; and U.S. Pat. Nos. 2,683,136 and 3,531,561 to Trehu. PGA is a homopolymer of glycolic acid (hydroxyacetic acid). In the conversion of glycolic acid to poly(glycolic acid), glycolic acid is initially reacted with itself to form the cyclic ester glycolide, which in the presence of heat and a catalyst is converted to a high molecular weight linear-chain polymer. PGA polymers and their properties are described in more detail in "Cyanamid Research Develops World's First Synthetic Absorbable Suture", Chemistry and Industry, 905 (1970).

Fibers can be formed by melt-spinning, extrusion, casting, or other techniques well known in the polymer processing area. Preferred solvents, if used to remove a scaffold prior to implantation, are those which are completely removed by the processing or which are biocompatible in the amounts remaining after processing.

Polymers for use in the matrix should meet the mechanical and biochemical parameters necessary to provide adequate support for the cells with subsequent growth and proliferation. The polymers can be characterized with respect to mechanical properties such as tensile strength using an Instron tester, for polymer molecular weight by gel permeation chromatography (GPC), glass transition temperature by differential scanning calorimetry (DSC) and bond structure by infrared (IR) spectroscopy.

Scaffolds can be of any desired shape and can comprise a wide range of geometries that are useful for the methods described herein. A non-limiting list of shapes includes, for example, hollow particles, tubes, sheets, cylinders, spheres, and fibers, among others. The shape or size of the scaffold should not substantially impede cell growth, cell differentiation, cell proliferation or any other cellular process, nor should the scaffold induce cell death via e.g., apoptosis or necrosis. In addition, care should be taken to ensure that the scaffold shape permits appropriate surface area for delivery of nutrients from the surrounding medium to cells in the population, such that cell viability is not impaired. The scaffold porosity can also be varied as desired by one of skill in the art.

In some embodiments, attachment of the cells to a polymer is enhanced by coating the polymers with compounds such as basement membrane components, agar, agarose, gelatin, gum arabic, collagens types I, II, III, IV, and V, fibronectin, laminin, glycosaminoglycans, polyvinyl alcohol, mixtures thereof, and other hydrophilic and peptide attachment materials known to those skilled in the art of cell culture or tissue engineering. Examples of a material for coating a polymeric scaffold include polyvinyl alcohol and collagen.

In some embodiments it can be desirable to add bioactive molecules to the scaffold. A variety of bioactive molecules can be delivered using the matrices described herein. These are referred to generically herein as "factors" or "bioactive factors".

In one embodiment, the bioactive factors include growth factors. Examples of growth factors include platelet derived growth factor (PDGF), transforming growth factor alpha or beta (TGFα or TGFβ), bone morphogenic protein 4 (BMP4), fibroblastic growth factor 7 (FGF7), fibroblast growth factor 10 (FGF10), epidermal growth factor (EGF), or vascular endothelium growth factor (VEGF), some of which are also angiogenic factors.

These factors are known to those skilled in the art and are available commercially or described in the literature. Bioactive molecules can be incorporated into the matrix and released over time by diffusion and/or degradation of the matrix, or they can be suspended with the cell suspension.

Screening Assays

The methods and compositions described herein are useful to screen for agents for inducing maturation of cardiac cells or for the treatment of a cardiac disease or disorder.

In some embodiments, the mature cardiomyocytes derived using the methods described herein can be used in methods, assays, systems and kits to develop specific in vitro assays. Such assays for drug screening and toxicology studies have an advantage over existing assays because they are of human origin, and do not require immortalization of cell lines, nor do they require tissue from cadavers, which poorly reflect the physiology of normal human cells. For example, the methods, assays, systems, and kits described herein can be used to identify and/or test agents that can promote cardiac function and/or cardiac metabolism. In addition to, or alternatively, the methods, assays, systems, and kits can be used to identify and/or test for agents useful in treating a cardiac disease or disorder, or for preventing/treating a cardiac injury.

Accordingly, provided herein are methods for screening a test compound for biological activity, the method comprising (a) contacting an isolated mature cardiomyocyte as described herein with a test compound and (b) determining any effect of the compound on the cell. In one embodiment, the screening method further comprises generating a mature cardiomyocyte as disclosed herein. The effect on the cell can be one that is observable directly or indirectly by use of reporter molecules.

As used herein, the term "biological activity" or "bioactivity" refers to the ability of a test compound to affect a biological sample. Biological activity can include, without limitation, elicitation of a stimulatory, inhibitory, regulatory, toxic or lethal response in a biological assay. For example, a biological activity can refer to the ability of a compound to modulate the effect of an enzyme, block a receptor, stimulate a receptor, modulate the expression level of one or more genes, modulate cell proliferation, modulate cell division, modulate cell metabolism, modulate differentiation, modulate cell morphology, modulate contractile function, or a combination thereof. In some instances, a biological activity can refer to the ability of a test compound to produce a toxic effect in a biological sample.

As used herein, the term "test compound" or "candidate agent" refers to an agent or collection of agents (e.g., compounds) that are to be screened for their ability to have an effect on the cell. Test compounds can include a wide variety of different compounds, including chemical compounds, mixtures of chemical compounds, e.g., polysaccharides, small organic or inorganic molecules (e.g., molecules having a molecular weight less than 2000 Daltons, less than 1000 Daltons, less than 1500 Dalton, less than 1000 Daltons, or less than 500 Daltons), biological macromolecules, e.g., peptides, proteins, peptide analogs, and analogs and derivatives thereof, peptidomimetics, nucleic acids, nucleic acid analogs and derivatives, an extract made from biological materials such as bacteria, plants, fungi, or animal cells or tissues, naturally occurring or synthetic compositions.

Depending upon the particular embodiment being practiced, the test compounds can be provided free in solution, or can be attached to a carrier, or a solid support, e.g., beads. A number of suitable solid supports can be employed for immobilization of the test compounds. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, polyaminemethylvinylether maleic acid copolymer, glass beads, amino acid copolymer, ethylene-maleic acid copolymer, nylon, silk, etc. Additionally, for the methods described herein, test compounds can be screened individually, or in groups. Group screening is particularly useful where hit rates for effective test compounds are expected to be low such that one would not expect more than one positive result for a given group.

A number of small molecule libraries are known in the art and commercially available. These small molecule libraries can be screened using the screening methods described herein. A chemical library or compound library is a collection of stored chemicals that can be used in conjunction with the methods described herein to screen candidate agents for a particular effect. A chemical library comprises information regarding the chemical structure, purity, quantity, and physiochemical characteristics of each compound. Compound libraries can be obtained commercially, for example, from Enzo Life Sciences™, Aurora Fine Chemicals™, Exclusive Chemistry Ltd.™, ChemDiv, ChemBridge™, TimTec Inc.™, AsisChem™, and Princeton Biomolecular Research™, among others.

Without limitation, the compounds can be tested at any concentration that can exert an effect on the cells relative to a control over an appropriate time period. In some embodiments, compounds are tested at concentrations in the range of about 0.01 nM to about 100 mM, about 0.1 nM to about 500 µM, about 0.1 µM to about 20 µM, about 0.1 µM to about 10 µM, or about 0.1 µM to about 5 µM.

The compound screening assay can be used in a high through-put screen. High through-put screening is a process in which libraries of compounds are tested for a given activity. High through-put screening seeks to screen large numbers of compounds rapidly and in parallel. For example, using microtiter plates and automated assay equipment, a laboratory can perform as many as 100,000 assays per day, or more, in parallel.

The compound screening assays described herein can involve more than one measurement of the cell or reporter function (e.g., measurement of more than one parameter and/or measurement of one or more parameters at multiple points over the course of the assay). Multiple measurements can allow for following the biological activity over incubation time with the test compound. In one embodiment, the reporter function is measured at a plurality of times to allow monitoring of the effects of the test compound at different incubation times.

The screening assay can be followed by a subsequent assay to further identify whether the identified test compound has properties desirable for the intended use. For example, the screening assay can be followed by a second assay selected from the group consisting of measurement of any of: bioavailability, toxicity, or pharmacokinetics, but is not limited to these methods.

In some embodiments, the screening assay comprises determining if a candidate agent alters action potential duration and/or induces a drug-induced arrhythmia. Such an assay can be performed by contacting a mature cardiomyocyte or population thereof, with a candidate agent and determining whether there is an alteration in action potential duration or if the agent produces a drug-induced arrhythmia. One of skill in the art can determine action potential duration and/or the presence of arrhythmia by using a single cell patch clamp, which permits detection of an early afterdepolarization or a delayed afterdepolarization in the cell. In addition, immunostaining and single-cell PCR can be performed to determine the presence of expressional changes in at least one cardiac ion channel. Methods for single-cell patch clamp, immunostaining and single-cell PCR are known to those of ordinary skill in the art.

Such a toxicity screening assay is particularly well-suited for determining a subject's susceptibility to cardiotoxicity from a particular drug. Thus in some embodiments, the assay and/or method comprises the steps of obtaining a biological sample from a subject (e.g., a somatic cell), reprogramming the cells in the biological sample to an iPSC (as necessary), inducing differentiation to a cardiomyocyte, and inducing the maturation of the cardiomyocyte as described herein. In such embodiments, a subject can be previously determined to have e.g., hereditary long QT syndrome, familial hypertrophic cardiomyopathy, familial dilated cardiomyopathy, dilated cardiomyopathy, hypertrophic cardiomyopathy, catecholaminergic polymorphic ventricular tachycardia, and/or LEOPARD syndrome.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 4$^{th}$ ed., J. Wiley & Sons (New York, N.Y. 2012); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 4th ed., Cold Spring Harbor Laboratory Press (Cold Spring Harbor, N.Y. 2012); provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

EXAMPLES

The adult human heart is incapable of significant regeneration after injury. Therefore, generating mature cardiomyocytes (CMs) from stem cells would be biomedically invaluable. Human embryonic stem cell derived cardiomyocytes (hESC-CMs) exhibit spontaneous beating, cardiac related action potential, calcium transients and have the ability to engraft to form new myocardium that is electromechanically integrated with the host myocardium[1-4]. In spite of their functional and physiological similarity to the CMs in the developing heart, several lines of evidence suggest that the hESC-CMs are at a fetal state with respect to their ion channel expression, electrophysiological activity and physical properties, thus diminishing their utility for modeling adult related heart disease and therapeutic screening[2, 5-8]. Although several promising strategies such as prolonged culturing[9] and 3-D tissue engineering are underway[10] to address this issue, scalability and time have been limiting parameters. Therefore it is critical to identify novel biological regulators that drive in vitro human cardiac maturation.

miRNAs are key factors in controlling a complex regulatory network in a developing heart[11]. Genetic studies that enrich or deplete miRNAs in specific cardiac tissue types and large scale gene expression studies have demonstrated that they achieve such complex control at the level of cardiac gene expression[12-14]. In this study, using large scale transcriptome analysis and splice variant analysis, the inventors first show that mRNA signatures of hESC-CMs taken through in vitro cardiac maturation reflect in vivo cardiac maturation. Furthermore, large scale miRNA sequencing of in vitro derived mature hESC-CMs reveals several key differentially regulated miRNAs and miRNA families. Target analysis using miRNA and mRNA datasets from mature CMs indicate that the let-7 family, which is one of the most highly up-regulated, targets key pathways including PI3/AKT/Insulin pathway during maturation. Interestingly, overexpression (OE) of selected members of the let-7 family in hESC-CMs significantly increases a number of "maturation" parameters such as cell size, sarcomere length, contractile force, and respiratory capacity. The let-7 OE CMs show significant down-regulation of a number of let-7 target genes in the PI3/AKT/Insulin pathway and a higher efficiency in the usage of fatty acid, palmitate as an energy source, thus indicating that the let-7 family is an important regulator of the metabolic switch during CM maturation.

Example 1

In Vitro Cardiac Maturation Physiologically Simulates In Vivo Cardiac Maturation The inventors adopted two different maturation protocols for H7-CMs (FIG. 1A): (i) 3D engineered heart tissue culture and (ii) prolonged 2D culture conditions. 3D engineered heart tissue was generated in gels of type I collagen and mechanically conditioned via static stress for two weeks by fixing the ends of the constructs between two posts (referred to herein as cEHT for conditioned Engineered Heart Tissue) as described by Tulloch et al.[15] In the second protocol, standard 2D cardiomyocytes (CMs) were subjected to prolonged culturing (13.5 months; referred to herein as "1yr-CM"). Cardiomyocyte populations with over 70% purity (assessed by flow cytometry for $cTnT^+$ cells) were used for all assays (FIG. 7) in this study. qPCR analysis of known cardiac markers validated the maturation process (FIGS. 1B, 1C). 1yr-CMs and cEHTs exhibited a significant up-regulation of cardiac troponin T (cTnT) (6- and 2-fold), Myosin heavy chain 7 (MYH7) (8- and 2.4-fold), sarcoendoplasmic reticulum ATPase (SERCA2a) (6- and 4-fold), gap junction protein alpha 1/connexin43 (GJA1) (7.5- and 5-fold) and increase in ryanodine receptor 2 (RYR2) expression (~4- and 1.8-fold) (FIGS. 1B, 1C). Interestingly, while the expression of fast $Na^+$ ion channel (SCN5A) and $K^+$ inward rectifier (KCNJ2) showed an up-regulation of ~3.5-fold and 26.2-fold, respectively, in the 1yr-CMs, these two genes showed no significant change in their expression pattern in the cEHTs, indicating that 1yr-CMs are more mature than the cEHTs.

Figure 1B:
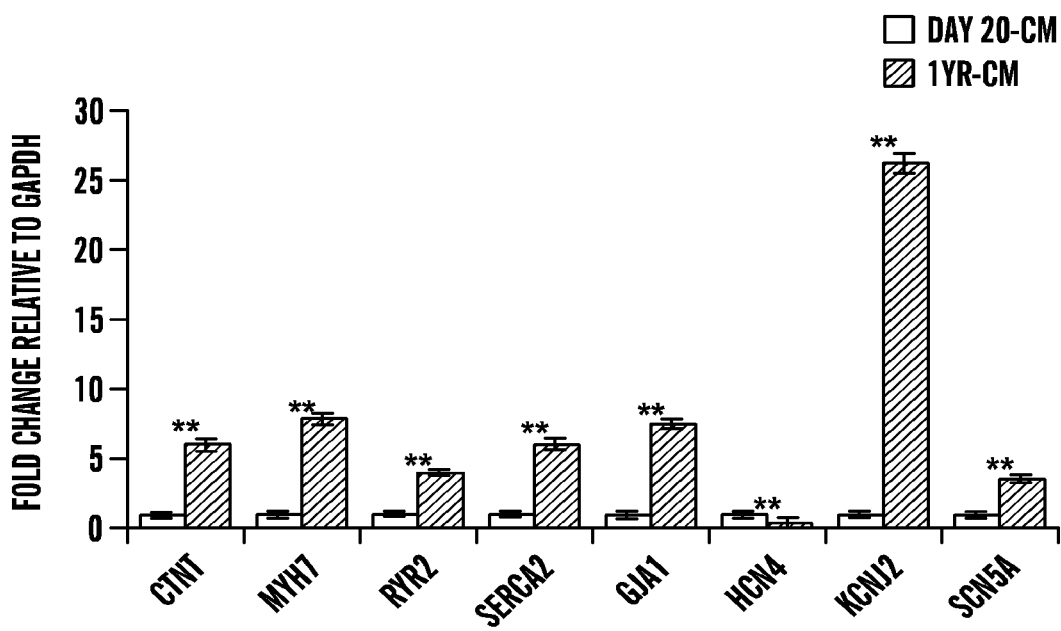
Figure 1C:
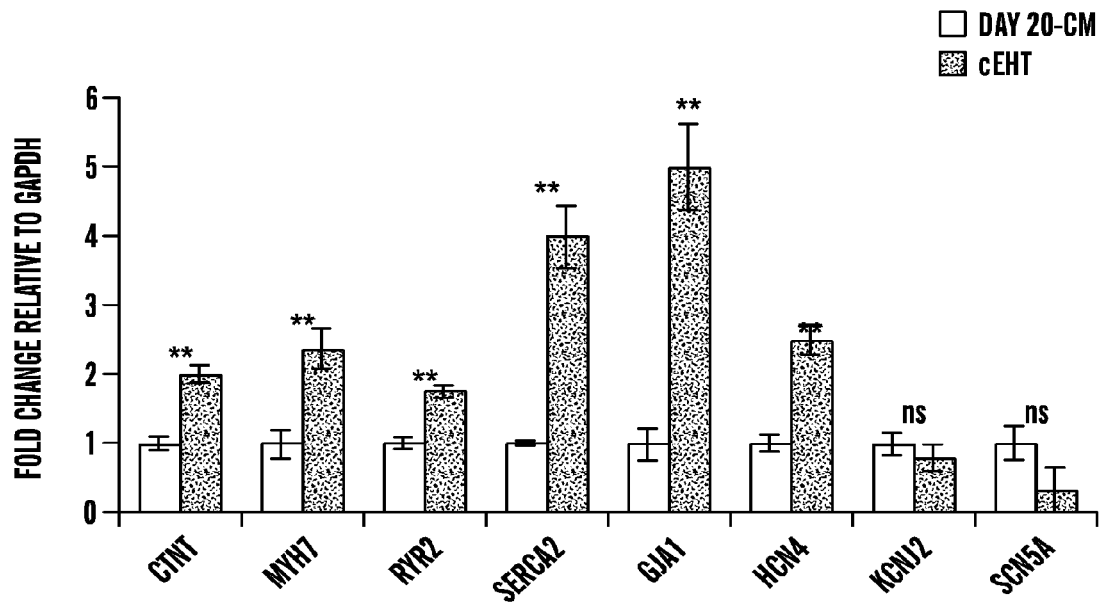

To further verify the extent of maturation of CMs generated by in vitro methods, the inventors used large scale sequencing using an ILLUMINA™ platform to compare the mRNA expression profiles between day 20-CMs and 1yr-CMs in relation to 3 month old human fetal ventricular (HFV) and atrial (HFA) samples[16] (FIG. 1A).

Figure 1D:
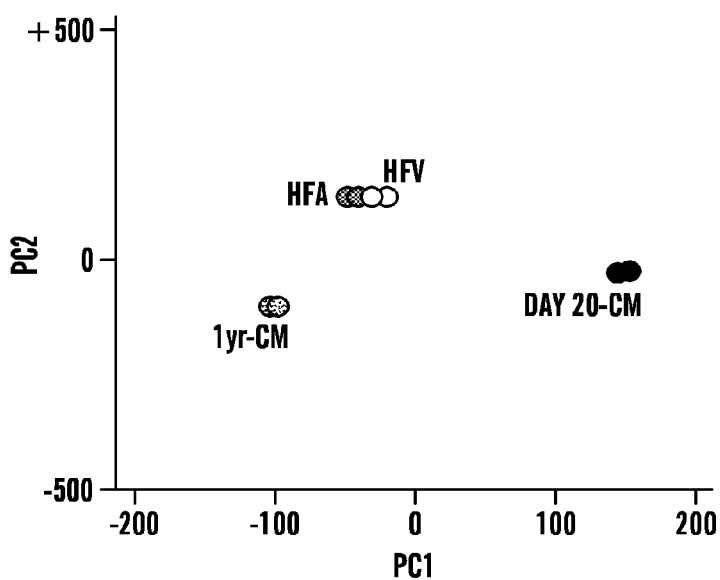
Figure 1E:
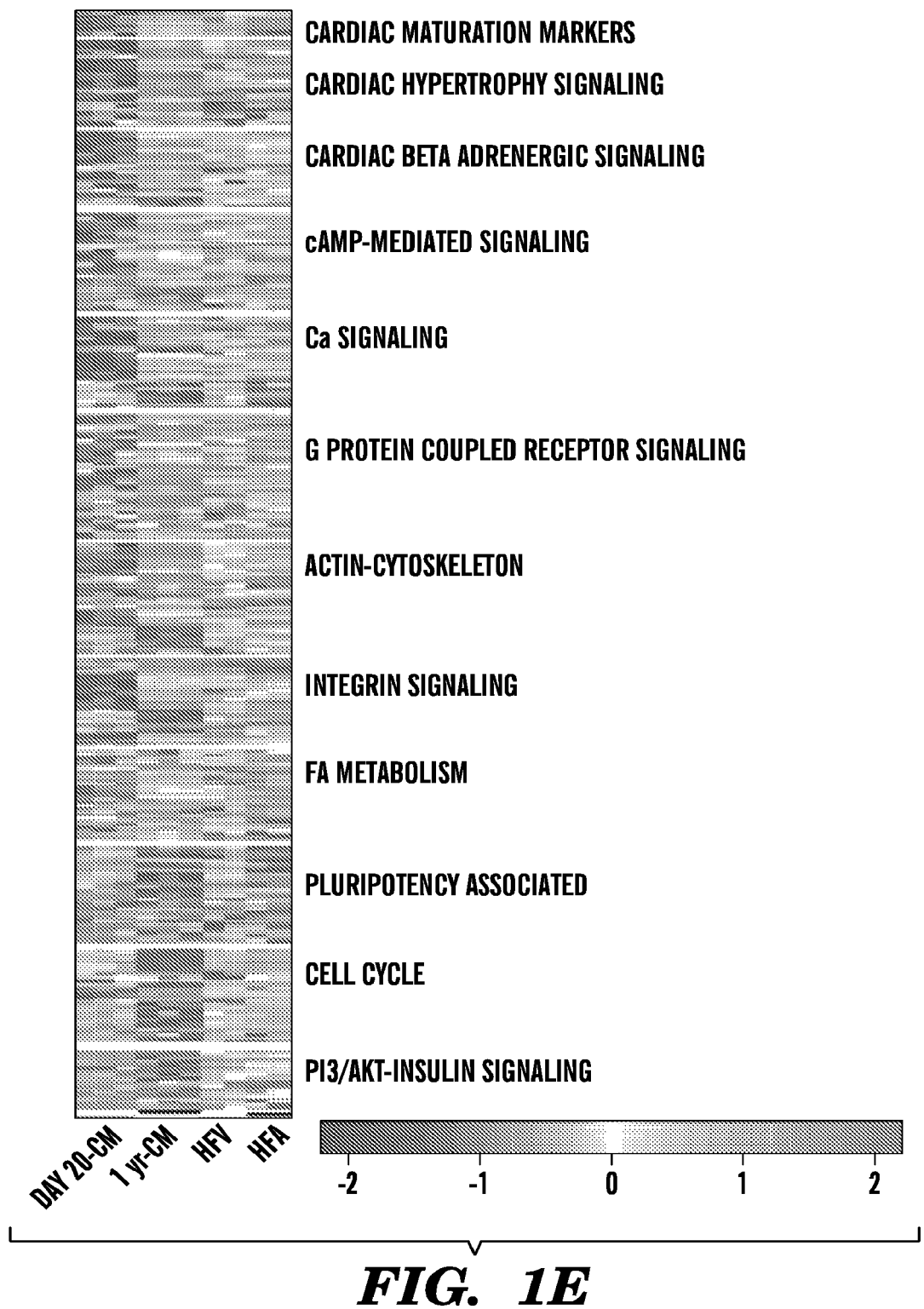

Two dimensional principal component analysis (2-D PCA) of all genes for all the samples clearly separates day 20-CMs from 1yr-CMs and HFA and HFV samples in dimension 1 with a variance of 25% in PC1 and 21% in PC2 (FIG. 1d). Examination of the transcript levels of all significantly regulated genes (P≤0.001 and FC≥2) in the above mentioned samples using INGENUITY PATHWAY ANALYSIS™ (IPA), revealed several interesting patterns and groups across the different samples. Cardiac maturation is known to improve Ca handling[17], FA metabolism[18, 19], sarcomere organization and results in the down-regulation of glucose metabolism/insulin signaling[20], cell proliferation[21] and pluripotency. Twelve categories reflecting these parameters are presented as a heat map (FIG. 1E). Most categories show the same trend of up or down regulation between 1yr-CMs, HFA and HFV samples indicating that several pathways known to be critical during in vivo heart development are also co-regulated during in vitro cardiac maturation (FIG. 1E). A more in-depth evaluation of the data using density plots revealed that pathways related to hypertrophic signaling, sarcomere organization (actin cytoskeleton), calcium and cAMP-mediated signaling[17] and integrin signaling were significantly up-regulated (p≤0.01) across 1 yr CMs, HFA and HFV samples, thereby indicating that in vitro maturation processes physiologically simulate the in vivo cardiac maturation (FIG. 1E-1H, FIGS. 8A-8F). For the first time this study has also revealed up-regulation of several genes in cardiac adrenergic receptor (AR) signaling pathway in fetal heart and in vitro matured hESC-CMs (FIGS. 8A-8C), indicating that this pathway can play a role in physiological maturation in contradiction to the traditional belief that AR signaling induces pathological hypertrophy[22].

Previous studies have shown that CMs rapidly proliferate during fetal life[21]. However, a vast majority of postnatal human CMs do not proliferate, although they are capable of DNA synthesis without nuclear division or nuclear division without cytokinesis, thereby increasing in ploidy (8N) and size (hypertrophy).[21, 23, 24] Consistent with these data, a number of cell cycle related genes were still up regulated in the 3 month old HFV and HFA samples (FIG. 1E) and did not show a significant down-regulation (FIG. 1*f-h*). In contrast, in the 1yr-CMs while the cell cycle genes, especially those related to G2 to M transition, were significantly down-regulated key negative regulators of cell cycle such as wee1[25] (Kellogg, 2003) are up-regulated, which is reflected as a biphasic curve in the density plots (FIG. 1F).

Figure 9:
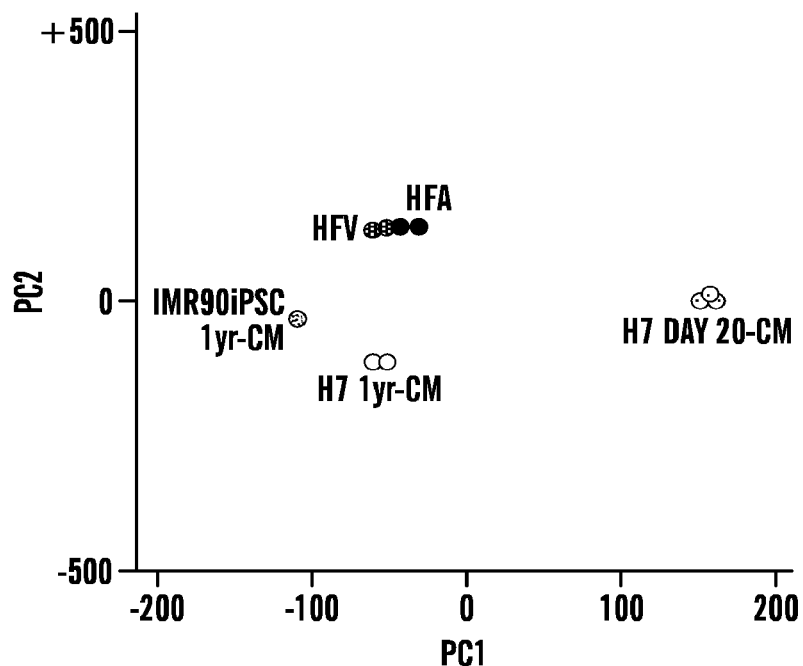
FIG. 9 IMR90iPSCs-CMs and H7-CMs show similar changes in gene expression after prolonged culturing. 2D-PCA using all genes demonstrating the position of IMR90iPSC 1yr-CMs relative to H7-1yr-CMs, HFA and HFV samples.

In animal models, CMs are known to shift their metabolism from glycolysis to fatty acid (FA) oxidation as they mature from fetal to adult state. This is well documented in in vivo and clinical studies using murine models and humans respectively.[18, 26] Consistent with this, the HFA and HFV samples do not show an increase in FA metabolism (FIGS. 1E, 1G, and 1H) while several genes in the FA metabolism pathway are up-regulated in 1yr-CMs (FIGS. 1E and 1F). Interestingly, in parallel to increased FA metabolism, a down-regulation of several genes in the PI3/AKT/Insulin pathway was observed in the 1yr-CMs (FIGS. 1C and 1G) indicating a reduced utilization of glucose for their metabolic needs. The effect of long term culturing on cardiac maturation was also analyzed in IMR90 induced pluripotent stem cell line and found that the overall gene expression of iMR90 iPSC line was very similar to that derived from H7 line (FIG. 9).

Example 2

Let-7 Family of miRNAs are Highly Expressed in hESC-CMs Matured in-the-Dish

Figure 2A:
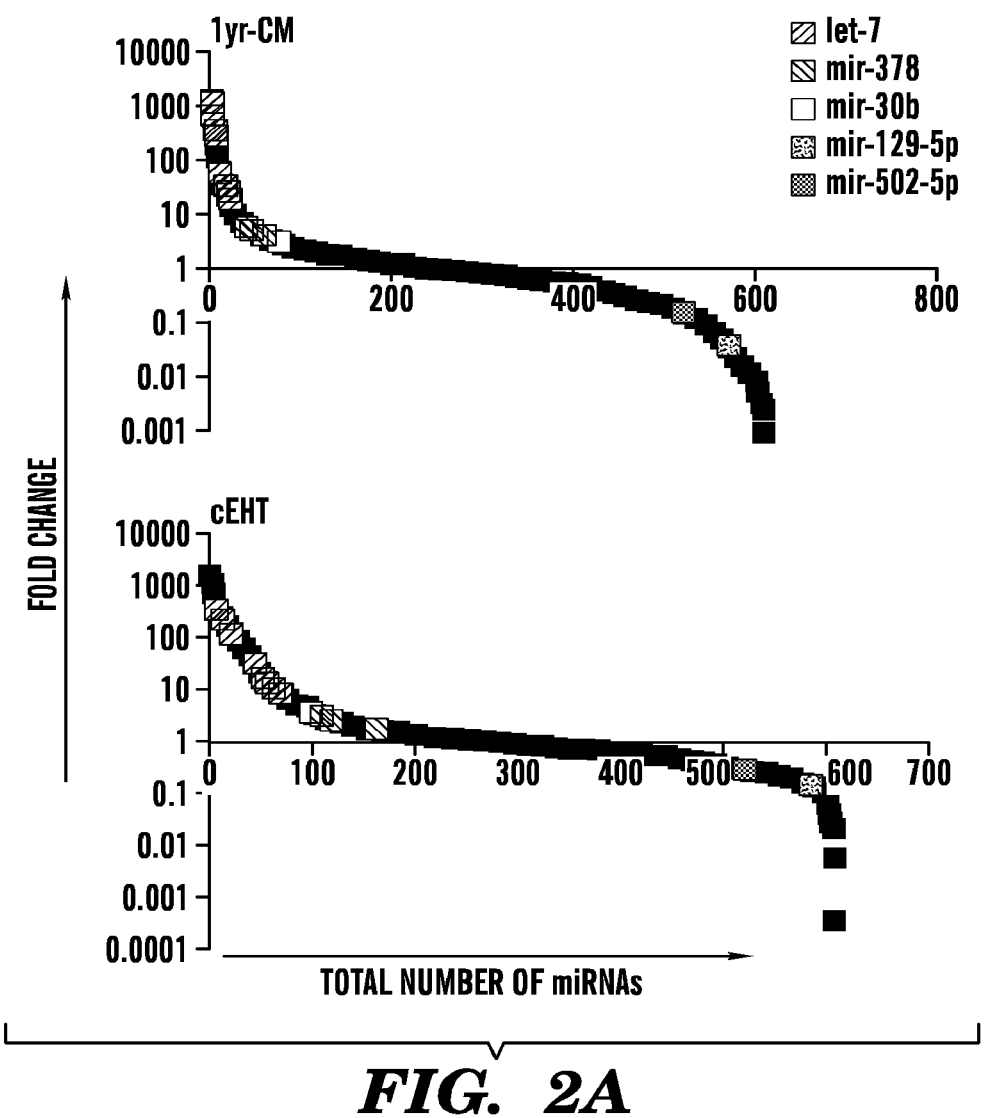

Since miRNA patterns in cEHTs and 1yr-CMs reflect the miRNA pattern changes observed during cardiac maturation, the inventors used an ILLUMINA™ high throughput miRNA sequencing platform to elucidate miRNAs that are highly enriched in these samples compared to Day 20-CMs (FIG. 2A). Approximately 600 miRNAs were identified with deducible read counts (FIG. 2A) from each of the two data sets. Of these, ~250 miRNAs were significantly regulated (FC≥2 and P≤0.001) in each data set. To derive a robust list of miRNA candidates that are regulated during maturation, the inventors selected miRNAs that were significantly regulated in both 1 yr old and cEHTs. This resulted in a list of 77 miRNAs (Table 1).

TABLE 1

List of 77 miRNAs significantly regulated in both 1 yr old and cEHTs.

| hsa-let-7b-5p | hsa-miR-664-3p | hsa-miR-200b-3p | hsa-miR-506-3p |
|---|---|---|---|
| hsa-let-7c | hsa-miR-98 | hsa-miR-218-5p | hsa-miR-509-3p |
| hsa-let-7d-5p | hsa-miR-301b | hsa-miR-222-5p | hsa-miR-514a-3p |
| hsa-let-7e-3p | hsa-miR-302a-3p | hsa-miR-205-5p | hsa-miR-122-5p |
| hsa-let-7e-5p | hsa-miR-302a-5p | hsa-miR-501-3p | hsa-miR-20b-5p |
| hsa-let-7f-5p | hsa-miR-302b-3p | hsa-miR-502-3p | hsa-miR-381 |
| hsa-let-7g-5p | hsa-miR-302c-3p | hsa-miR-502-5p | hsa-miR-409-3p |
| hsa-let-7i-5p | hsa-miR-302d-3p | hsa-miR-532-3p | hsa-miR-410 |
| hsa-miR-190a | hsa-miR-302e | hsa-miR-548a-5p | hsa-miR-411-5p |

TABLE 1-continued

List of 77 miRNAs significantly regulated in both 1 yr old and cEHTs.

| hsa-miR-193a-5p | hsa-miR-222-5p | hsa-miR-548c-5p | hsa-miR-654-3p |
|---|---|---|---|
| hsa-miR-30b-3p | hsa-miR-129-1-3p | hsa-miR-548g-3p | hsa-miR-766-3p |
| hsa-miR-3200-3p | hsa-miR-129-2-3p | hsa-miR-548i | hsa-miR-1179 |
| hsa-miR-361-3p | hsa-miR-129-5p | hsa-miR-548o-5p | hsa-miR-423-5p |
| hsa-miR-378a-5p | hsa-miR-141-3p | hsa-miR-5683 | hsa-miR-4485 |
| hsa-miR-378b | hsa-miR-142-5p | hsa-miR-592 | hsa-miR-488-3p |
| hsa-miR-378e | hsa-miR-182-5p | hsa-miR-708-5p | hsa-miR-490-5p |
| hsa-miR-378f | hsa-miR-183-5p | hsa-miR-935 | hsa-miR-204-5p |
| hsa-miR-378g | hsa-miR-188-3p | hsa-miR-96-5p | |
| hsa-miR-499a-5p | hsa-miR-18a-3p | hsa-miR-500a-3p | |
| hsa-miR-584-5p | hsa-miR-200a-3p | hsa-miR-1247-5p | |

Figure 2B:
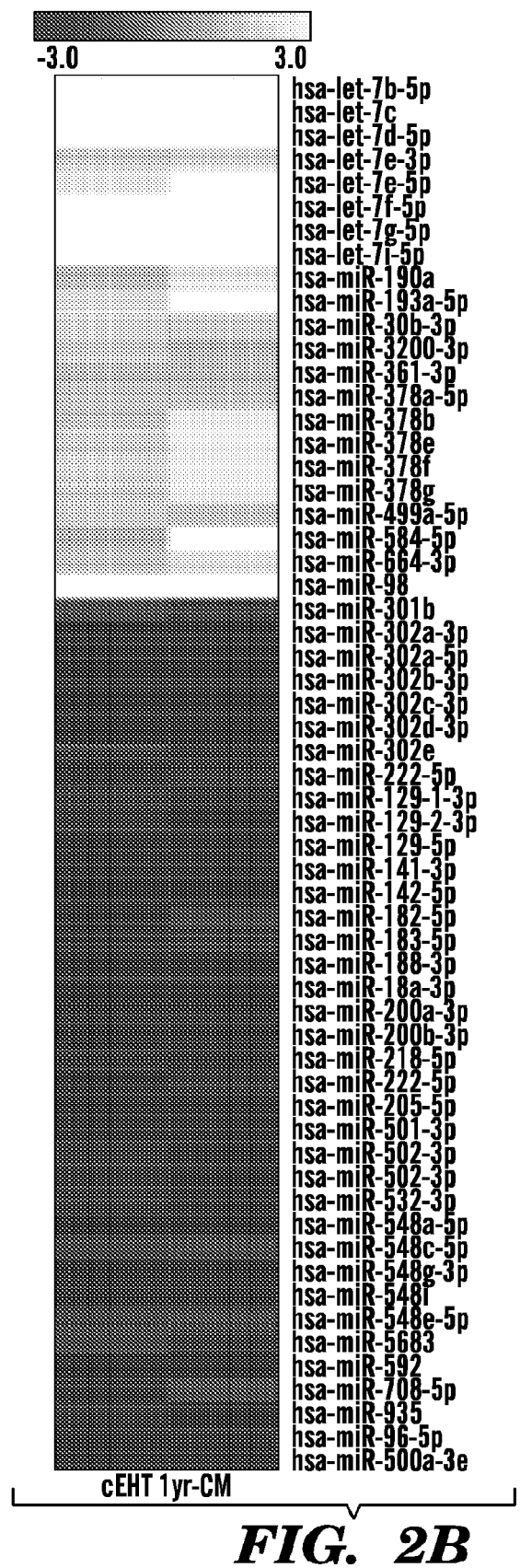
Figure 10:
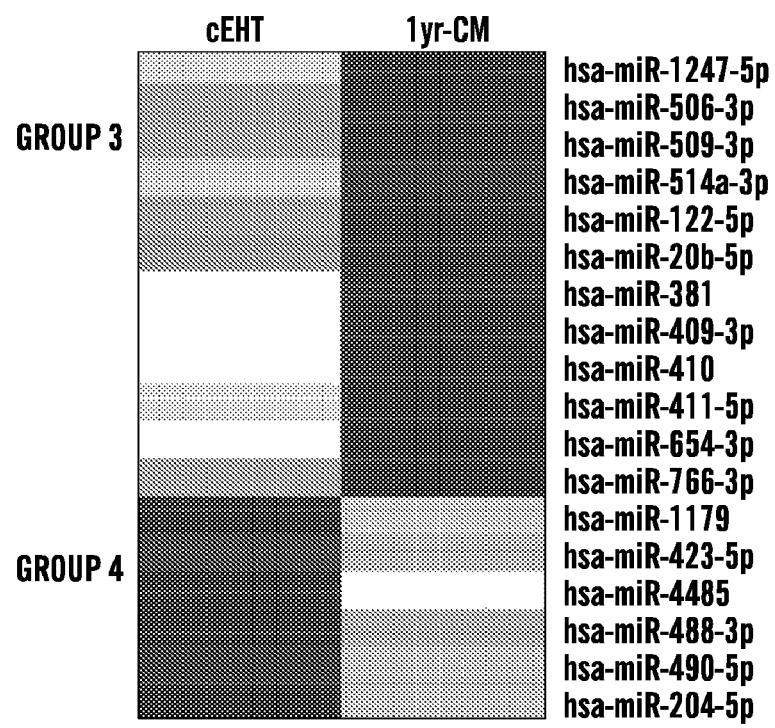
FIG. 10 Heat map generated using multi expression viewer includes fold changes of all significantly regulated miRNAs (FC≥2 and p≤0.001) that are common between 1yr-CMs and cEHTs relative to day 20 CMs. Groups 3 and 4 indicate miRNAs that are significantly up regulated in cEHT and down-regulated in 1yr-CM and vice versa respectively.

The rest of the miRNAs were significantly changed in only one of the two data sets and thus were not included for this analysis. A heat map analysis of the 77 miRNAs in the two data sets revealed 4 groups of miRNAs (FIG. 2B and FIG. 10): Some representative candidates of group 1 were members of the let-7 and mir-378 families and mir-30. Similarly, candidate members that were down regulated in both data sets were mir-502 and mir-129 (group 2). To delineate the pathways most significantly regulated by miRNAs during cardiomyocyte maturation, the inventors analyzed two groups of miRNA-mRNA interactions from 1 yr old CMs using IPA's (INGENUITY SYSTEMS™) miRNA-mRNA target filter algorithm: A) the overlap between the targets of down-regulated miRNAs and up-regulated mRNA in mature CMs; B) the overlap between the targets of up-regulated microRNAs and down-regulated mRNAs during maturation. The 3 miRNAs showing the highest number of targets in the mRNA dataset were let-7, mir-378, mir-129 (FIGS. 2A-3C) and thus chosen for further pathway analysis using GENEMANIA™ and/or previous literature. Interestingly, pathway analysis algorithm of GENEMANIA™ revealed that most of the let-7 targets that were down-regulated in cardiomyocyte maturation belonged to PI3/AKT/Insulin signaling.

Example 3

Induction of Let-7 Promotes Maturation of hESC-CM

Figure 3A:
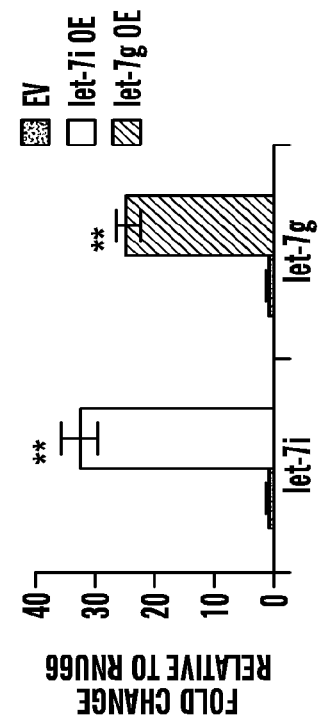
Figure 3B:
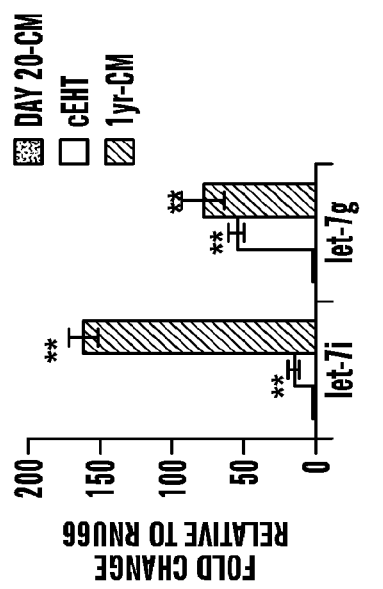
Figure 3C:
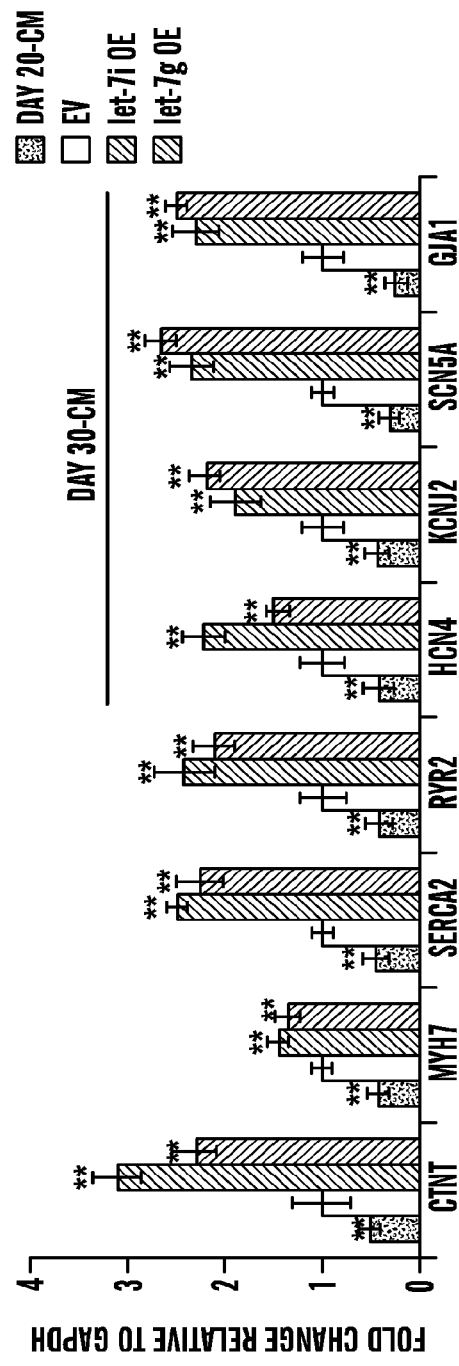
Figure 3K:
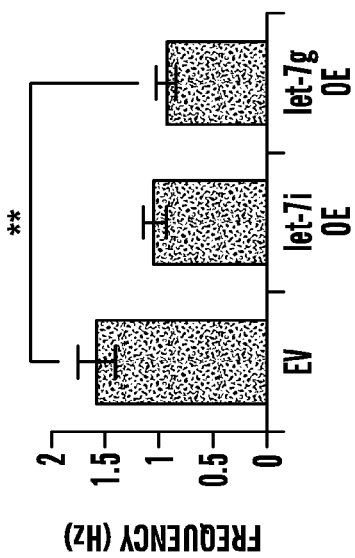
Figure 3J:
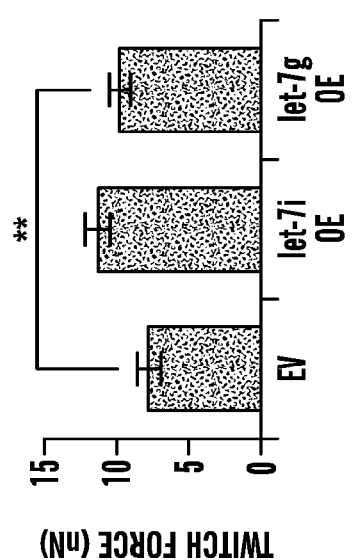
Figure 11B:
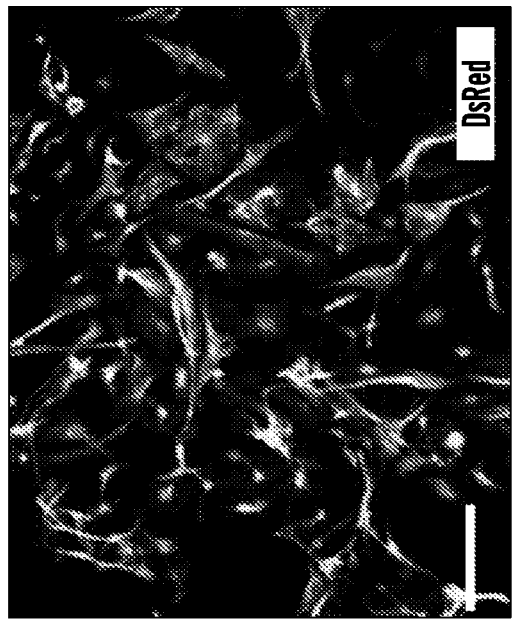
FIGS. 11A-11C Transduction efficiency of pLKOlentiviral vector using DsRed reporter expression. Lentiviral transduction of the pLKO-DsRed construct was carried out in cardiomyocytes at day 12 of differentiation run. DsRed reporter expression was analyzed at day 20. DAPI (FIG. 11A) and Ds red immuno fluorescence staining (FIG. 11B) of CMs that are at day 20 of directed differentiation run. Scale bar=50 µm.
Figure 11A:
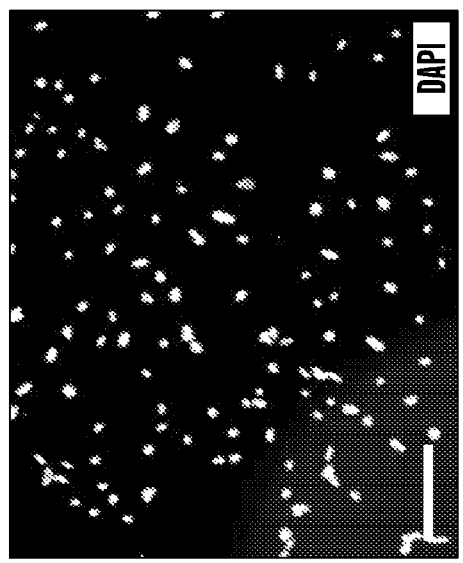
Figure 11C:
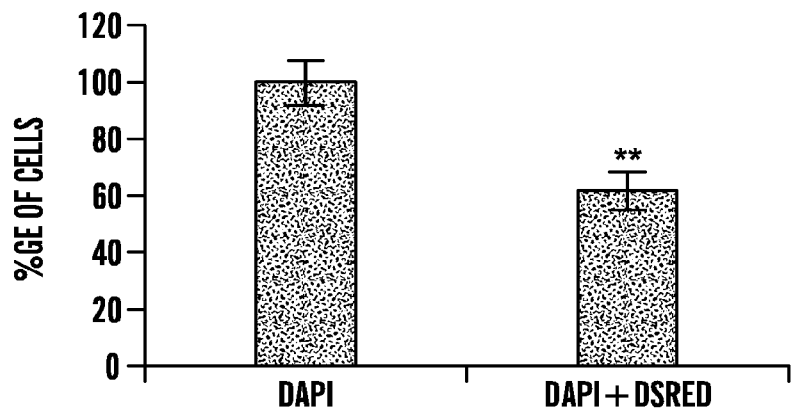

To further examine the let-7 family in relation to cardiomyocyte maturation, the inventors selected two members of the let-7 family, let-7g and let-7i, and validated their up regulation using qPCR (FIG. 3A). For further functional analyses the inventors used a pLKO-lentiviral based system to independently overexpress (OE) these candidates for up to two weeks in CMs. All analyses of let-7 OE were carried out when the CMs were roughly at day 30. To test whether the potential effects of let-7 are universal and not dependent on the hESC line used to derive the CMs, the inventors used another independent hESC line, RUES2, for this OE study. The overall transduction efficiency of the lentivirus in the RUES2-derived CMs was assessed to be ~60% using a Ds-Red-encoding virus (FIG. 11). qPCR analysis validated let-7i and let-7g over expression in CMs that were transduced with let-7 OE lentiviruses (FIG. 3*b*). In comparison to the empty vector (EV) control, let-7 OE CMs also exhibited a significant increase in all the cardiac maturation markers that were previously found to be up-regulated in the cEHTs and 1yr-CMs (FIGS. 1B and 3C). This provided the first indication that overexpression of let-7 accelerates the maturation process.

The inventors then characterized multiple parameters that have been shown to be modulated during cardiac developmental maturation[8]. For these studies α-actinin (Z-disk protein) staining was used to visualize the EV control and let-7 OE CMs (FIG. 3D). The inventors observed a significant increase in cell perimeter (let-7i OE, 300±7.4 µm; let-7g OE, 302±3 µm vs. 108±15 µm, P<0.001), cell area (let-7i OE, 1110±101 µm$^2$; let-7g OE, 980±95 µm$^2$ vs. 380±70 µm$^2$, P<0.001) (FIG. 3d-f). Circularity index (4πArea/(perimeter)$^2$) decreased in CMs that were overexpressing let-7i and let-7g vs. EV control (let-7i OE, 0.15±0.04; let-7g OE, 0.12±0.02 vs. 0.41±0.02) (FIGS. 3d and g). The inventors also found that the sarcomere length increased from 1.65±0.02 µm in EV control cells to 1.70±0.01 µm and 1.69±0.01 (P<0.001) in let-7i and let-7g OE samples respectively (FIGS. 3D and 3H). An increase in sarcomeric length generally corresponds to an increase in the force of contraction. To characterize force production on a per-cell basis, the inventors used arrays of microposts to measure their contractile forces (FIG. 3I)[27]. EV control CMs exhibited a twitch force of 7.77±0.7 nN/cell. Let-7i and let-7g OE CMs exhibited a significantly higher average twitch force of 11.32±0.86 and 9.28±0.7 (nN/cell; P<0.001), respectively (FIGS. 3i and j). In addition, let-7 OE CMs (let-7i OE: 1.05±0.1 hz; let-7g OE: 0.92±0.094 hz) exhibited lower beat frequency compared to EV control (1.57±0.1 hz). This decrease in frequency corresponds well with what is seen in in vivo human heart development i.e., as cardiomyocytes mature, they begin to exhibit reduced beating frequency[28]. These data demonstrate that let-7OE not only results in morphological and molecular changes indicative of maturation, but that functionally relevant parameters, such as contraction and beat frequency are also appropriately regulated.

Figure 4A:
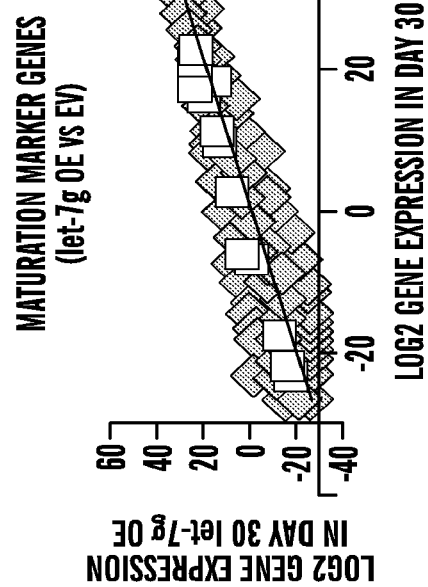
FIGS. 4A-4G Let-7 is critical for in vitro cardiac maturation.
Figure 4B:
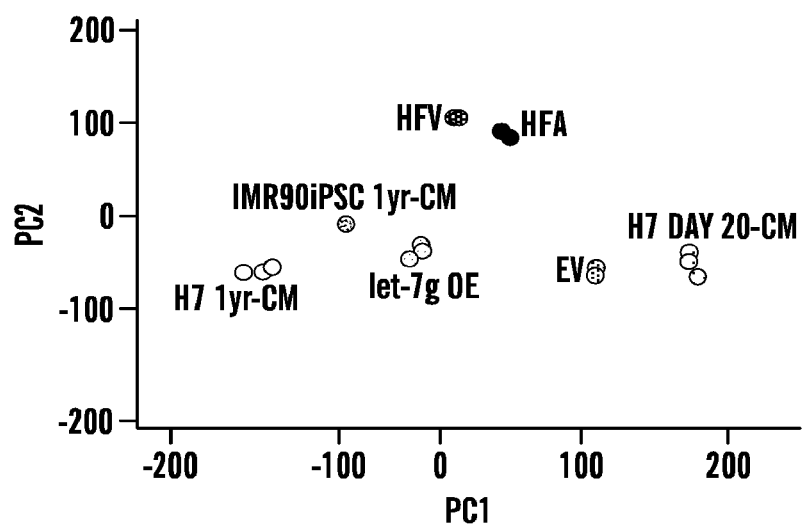
Figure 4C:
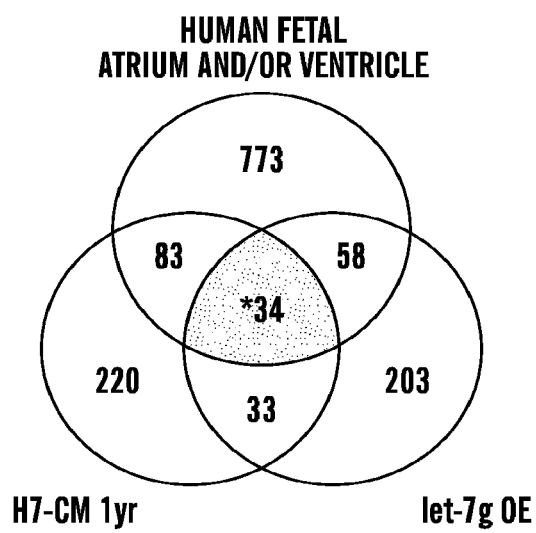
Figure 4D:
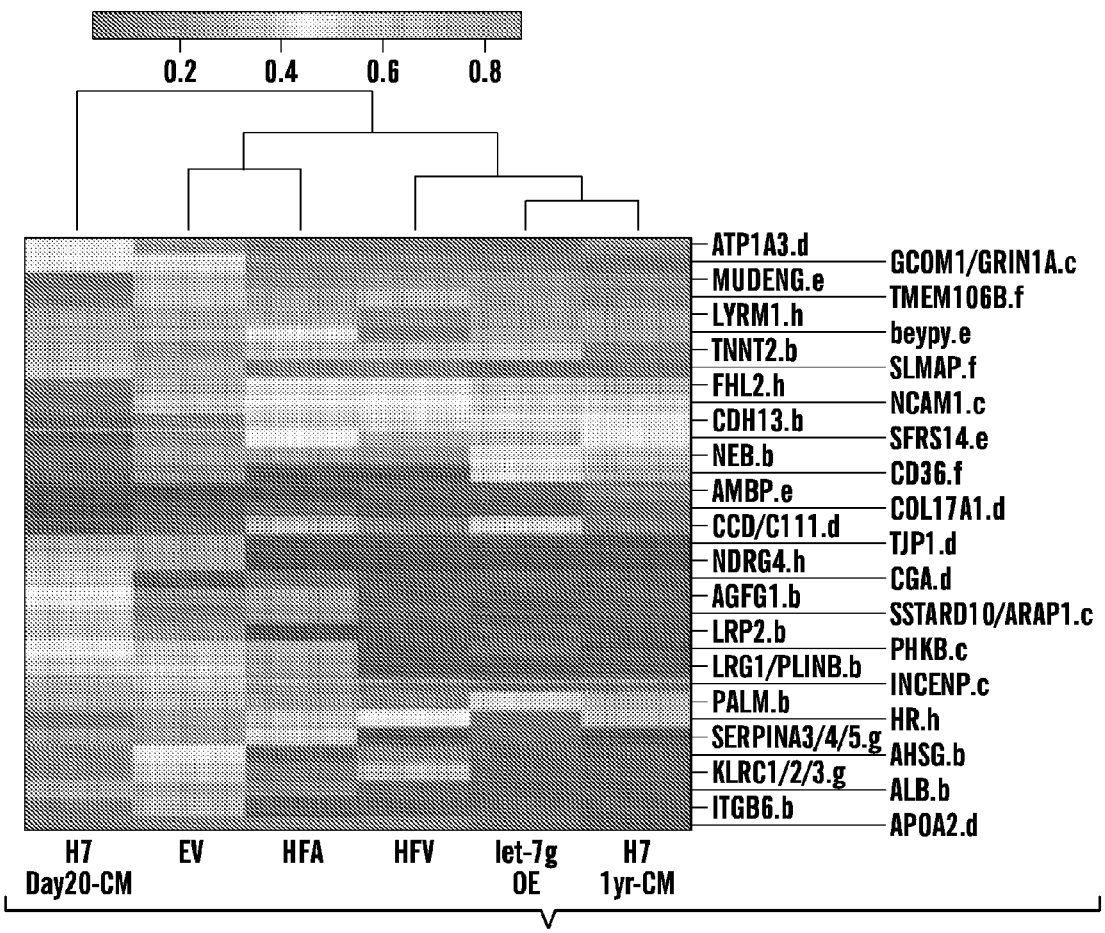
Figure 4E:
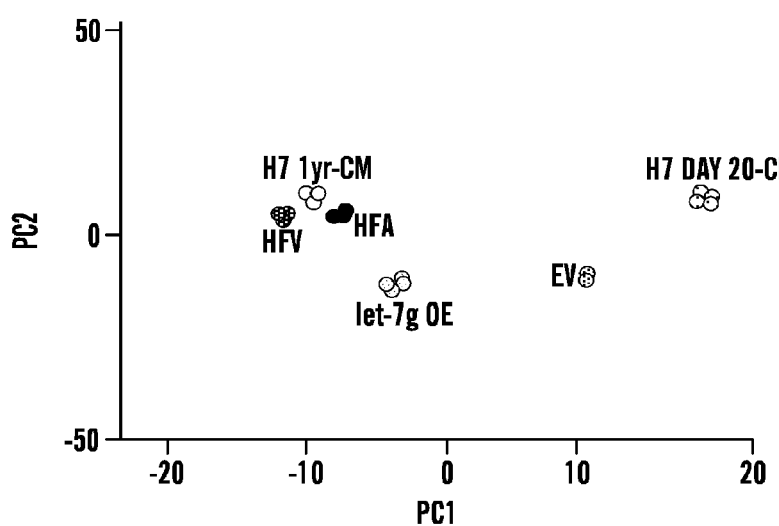
Figure 12A:
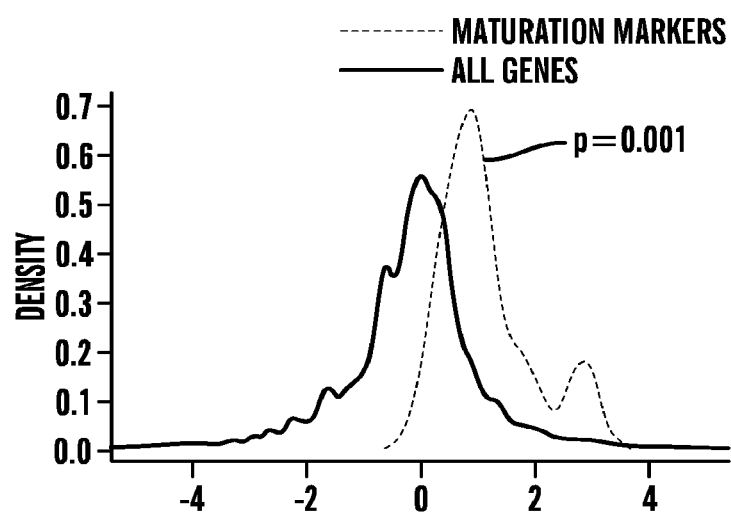
FIGS. 12A-12B Overexpression of let-7 results in accelerated maturation.
Figure 12B:
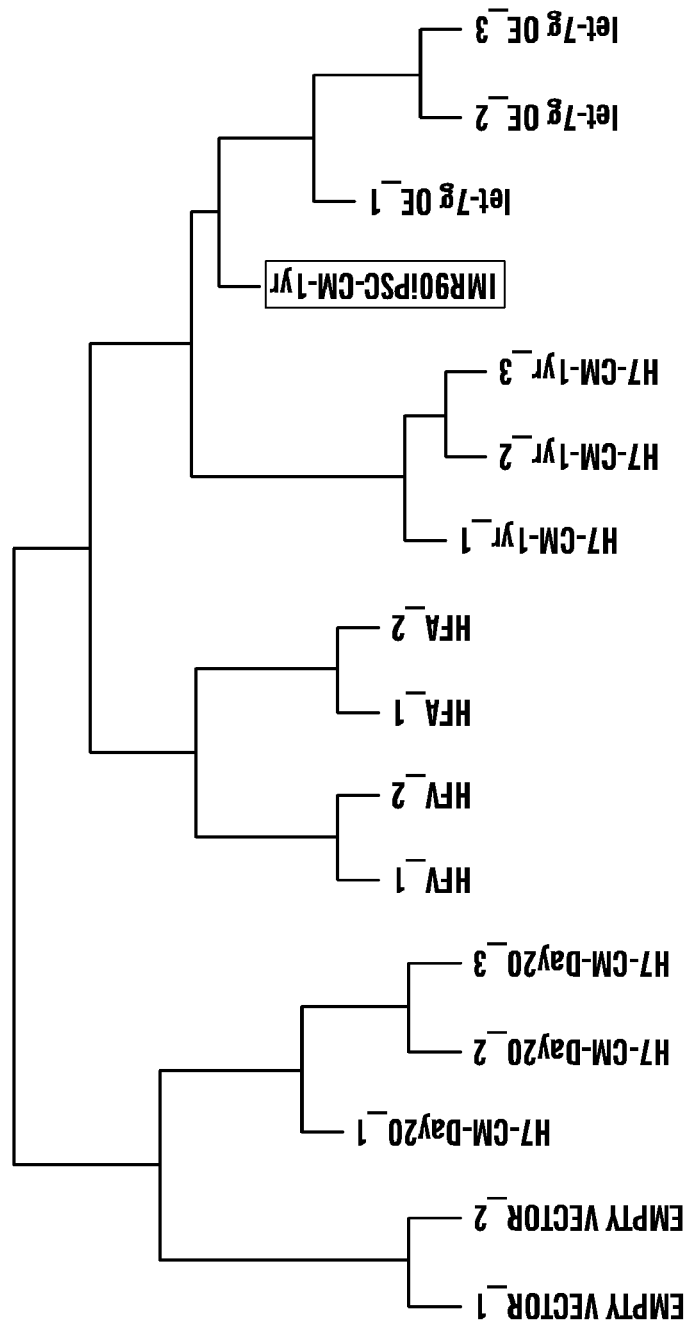
Figure 13:
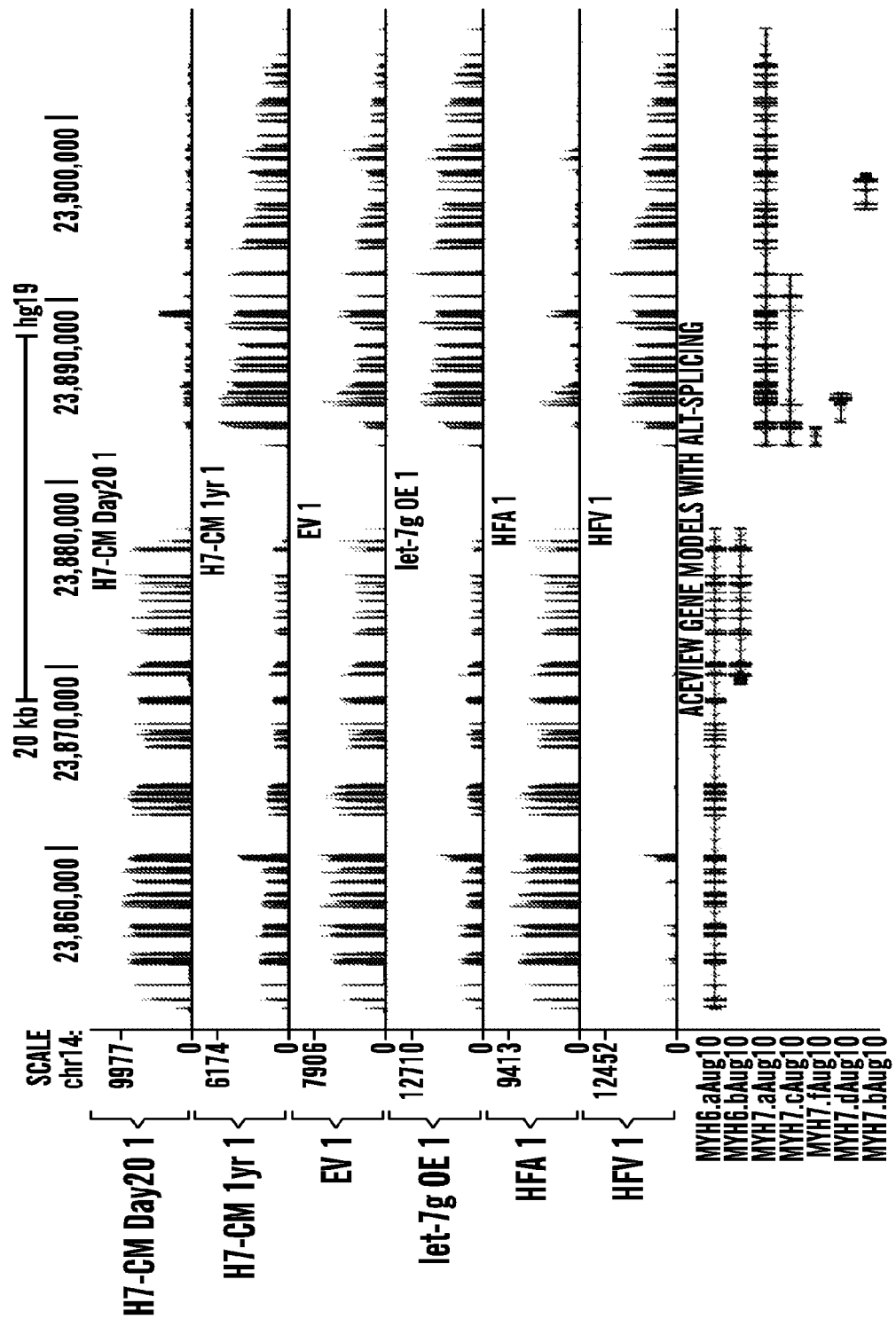
FIG. 13 Let-7 OE in CMs results in isoform switch from myosin heavy chain (MyH) 6 (alpha; fast-twitch) to 7 (beta; slow-twitch) similar to that seen in 1 yr CMs and fetal ventricle sample. Screenshot from the UCSC genome browser showing detected isoform switching. The top 6 tracks show read coverage (i.e., number of reads covering each position) on the y-axis for replicate 1 of the RNAseq data for each condition. Lower tracks give a representation of isoforms annotated by ACEVIEW™.
Figure 14:
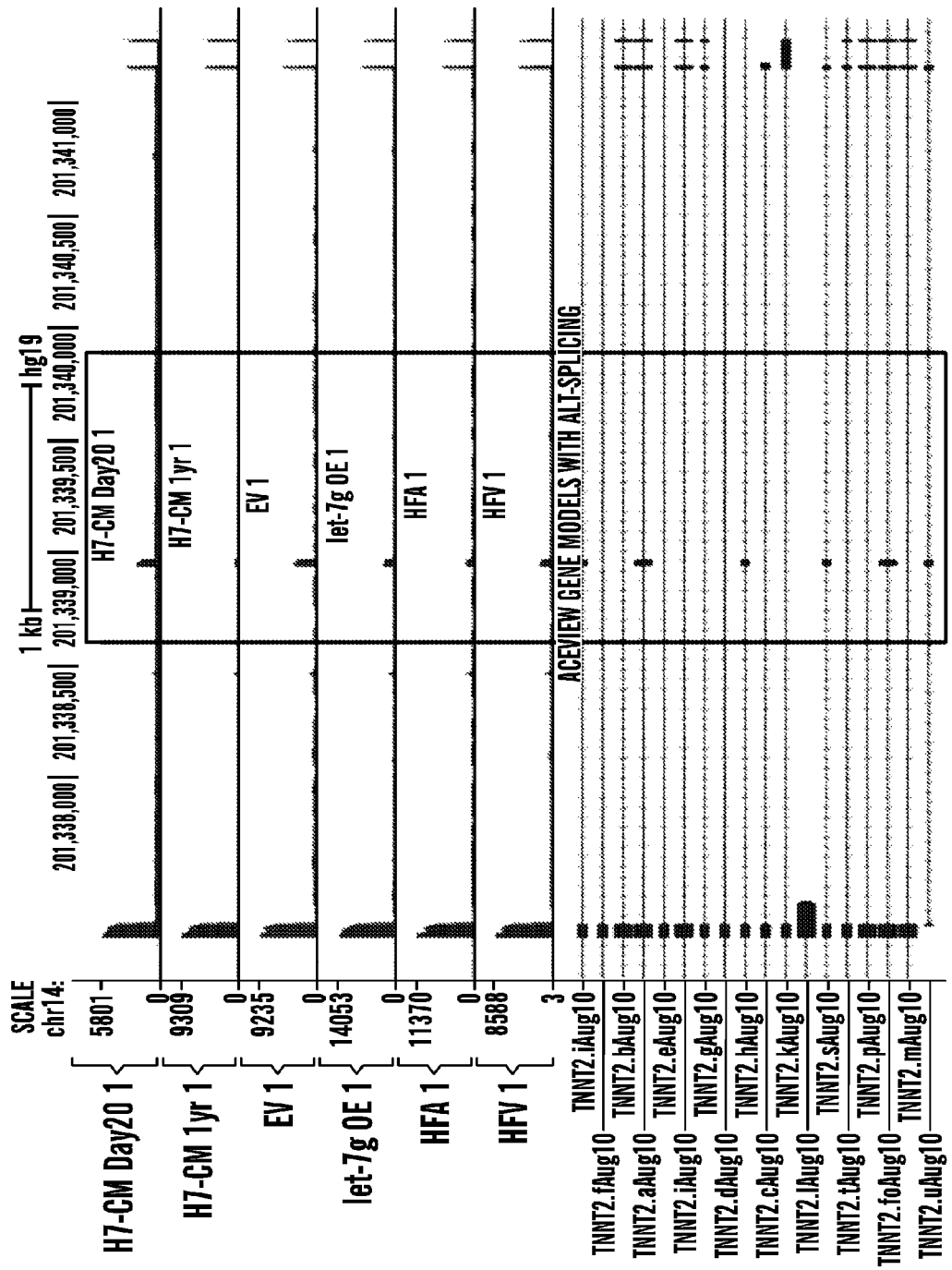
FIG. 14 Putative alternative spliced variant of Cardiac Troponin T2 in let-7g OE CMs resembles that seen in 1 yr CMs and fetal samples. Screenshot from the UCSC genome browser is similar in layout to the one shown in FIG. 11, but focused on a portion of the Troponin T type 2 locus (TNNT2). One exon (marked in a box) is included in the TNNT2.a isoform, but excluded from the TNNT2.b isoform (ACEVIEW™ annotations; lower tracks). Read coverage (i.e., number of reads covering each position, shown in the y-axis for replicate 1 of each condition in the upper tracks) shows increased exclusion of this exon in let-7 OE and mature samples compared to day 20 and empty vector. Detailed analysis by ISOLATOR™ attributes most of this change to a shift from TNNT2.a to TNNT2.b. ISOLATOR™ predictions account for factors not visible these screen shots, including variability across replicates, reds crossing splice junctions, etc.

To further understand the effects of let-7 OE during cardiomyocyte maturation at a molecular level, the inventors carried out whole genome transcriptome profiling of let-7g OE CMs and corresponding EV control CMs using an ILLUMINA™ RNA sequencing platform. Consistent with qPCR data, several known maturation markers such as RYR2, MYH7, KCNJ2 showed an increased expression in the let-7g OE CMs compared to EV control (FIG. 4A, 12A). Using expression values for the genes that belonged to the 12 pathways (FIG. 1E), the inventors carried out a 2D-PCA comparing let-7g OE CMs and EV control CMs with H7-CMs at day 20 and 1 yr, IMR90iPSC-CMs at 1 yr and 3 month old HFA and HFV samples. This analysis clearly separated the day 20-CMs from 1yr-CMs derived from H7 and IMR90iPSCs and HFA and HFV in dimension 1 (41% variance) indicating that dimension 1 portrays the effect of maturation (FIG. 4B, 12B). Significantly, let-7g OE was closer to 1 yr than the EV and day 20 CMs in the first dimension indicating that over expression of let-7g does indeed result in accelerated maturation. Further evidence of let-7g directed maturation was observed from known isoform changes accompanying cardiomyocyte maturation, such as shifts in myosin heavy chain (MYH6/MYH7)[29] (FIG. 13). Further, a new differential splicing analysis tool[30] used by the inventors shows a total of 1404 unique genes to be differentially spliced between H7-CM day 20 and one or more of the other samples (FIG. 4C). Focusing on the 34 differentially spliced genes in common among H7-CM-1yr, let-7 OE and fetal samples (FIG. 4C), the inventors identified the single transcript of each showing the greatest absolute change in proportion between H7-CM day 20 and the above three samples (data not shown). As seen in FIG. 4D, the changes in these single transcripts are clearly aligned with the developmental chronology of these samples and more interestingly these change cluster let-7g OE CMs with H7-CM 1 yr and ventricular samples. The same pattern emerges from analysis of the relative expression levels of all 377 isoforms (data not shown) of these 34 genes again showing that the developmental chronology of the samples is well captured by principal component 1. In short, there are concerted and dynamic changes in splicing during maturation. The fact that both differential splicing and differential expression analyses cluster let-7 OE CMs with H71yr-CM and fetal samples, clearly strengthens the finding that let-7 is critical for maturation. Interestingly, among the 34 genes, several have been shown to be involved in cardiogenesis including CD36[31], TNNT2[32], CDH13[33] (FIG. 14).

Example 4

Let-7 Promotes hESC-CM Maturation by Acting as a Metabolic Switch

Figure 4F:
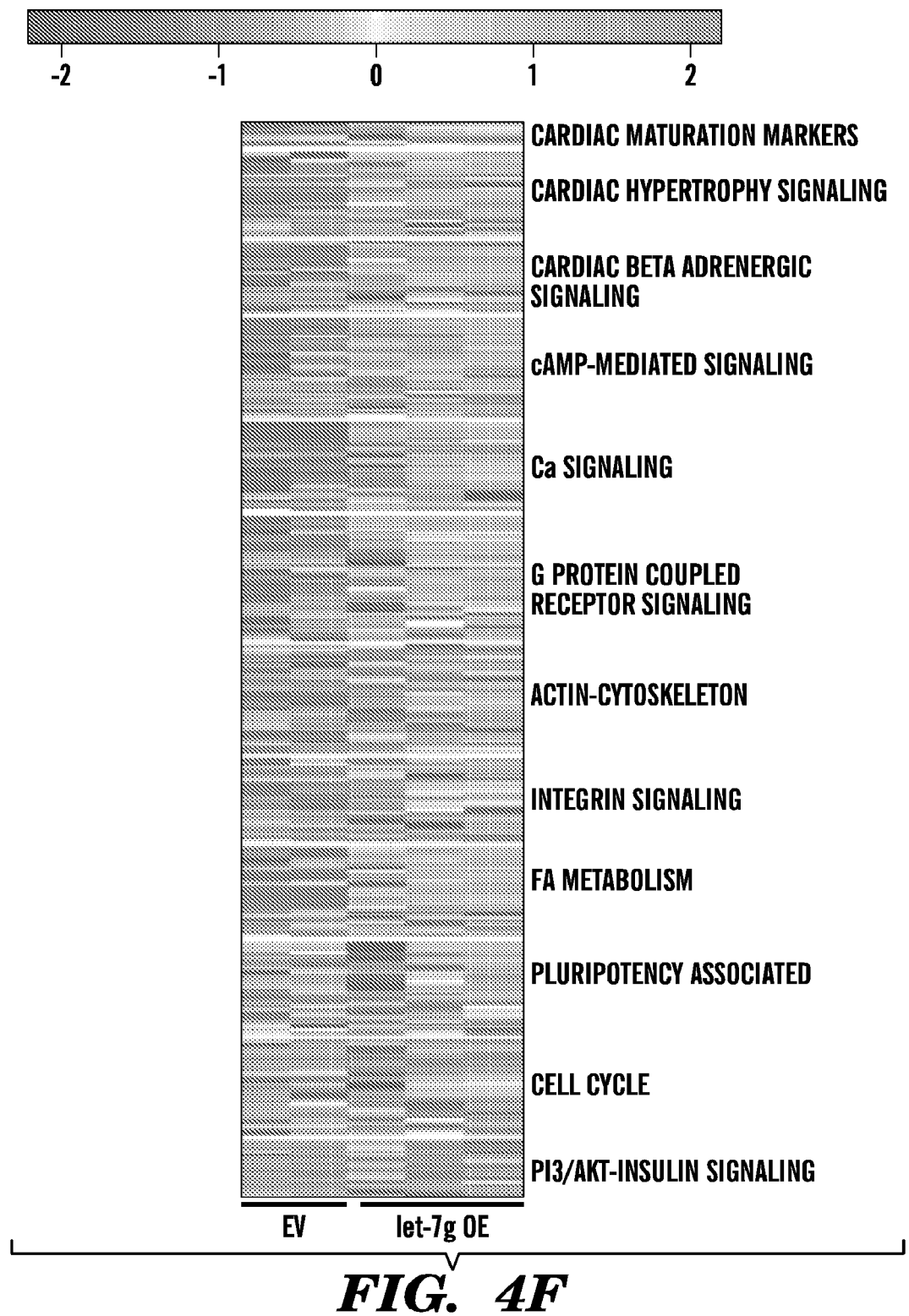
Figure 4G:
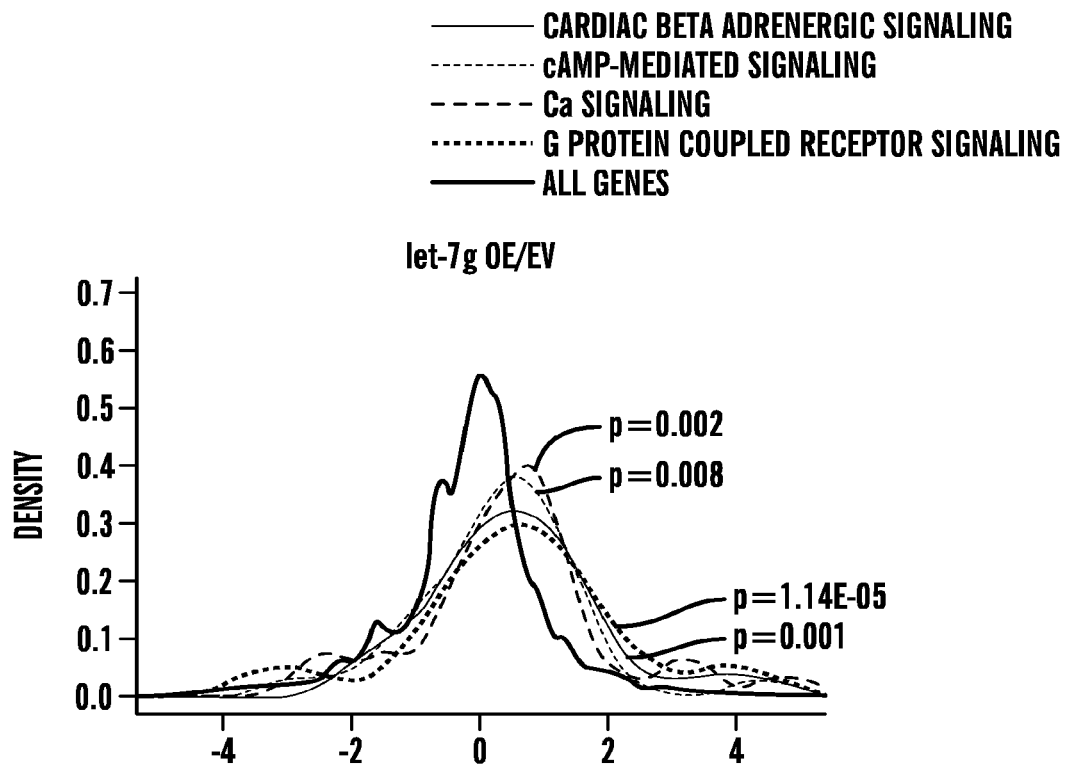
Figure 5A:
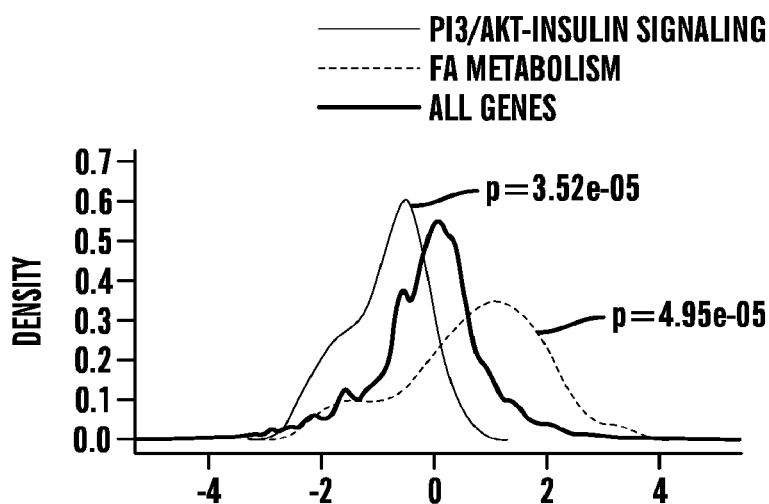
FIGS. 5A-5G Let-7 over expression results in down-regulation of PI3/AKT/Insulin pathway and up-regulation of FA metabolism. Comparisons were done between let-7OE and EV control for all assays (FIG. 5A) Density plots using R generated with fold change expression (let-7g OE/EV) of genes for FA metabolism and PI3/AKT/Insulin signaling.
Figure 5B:
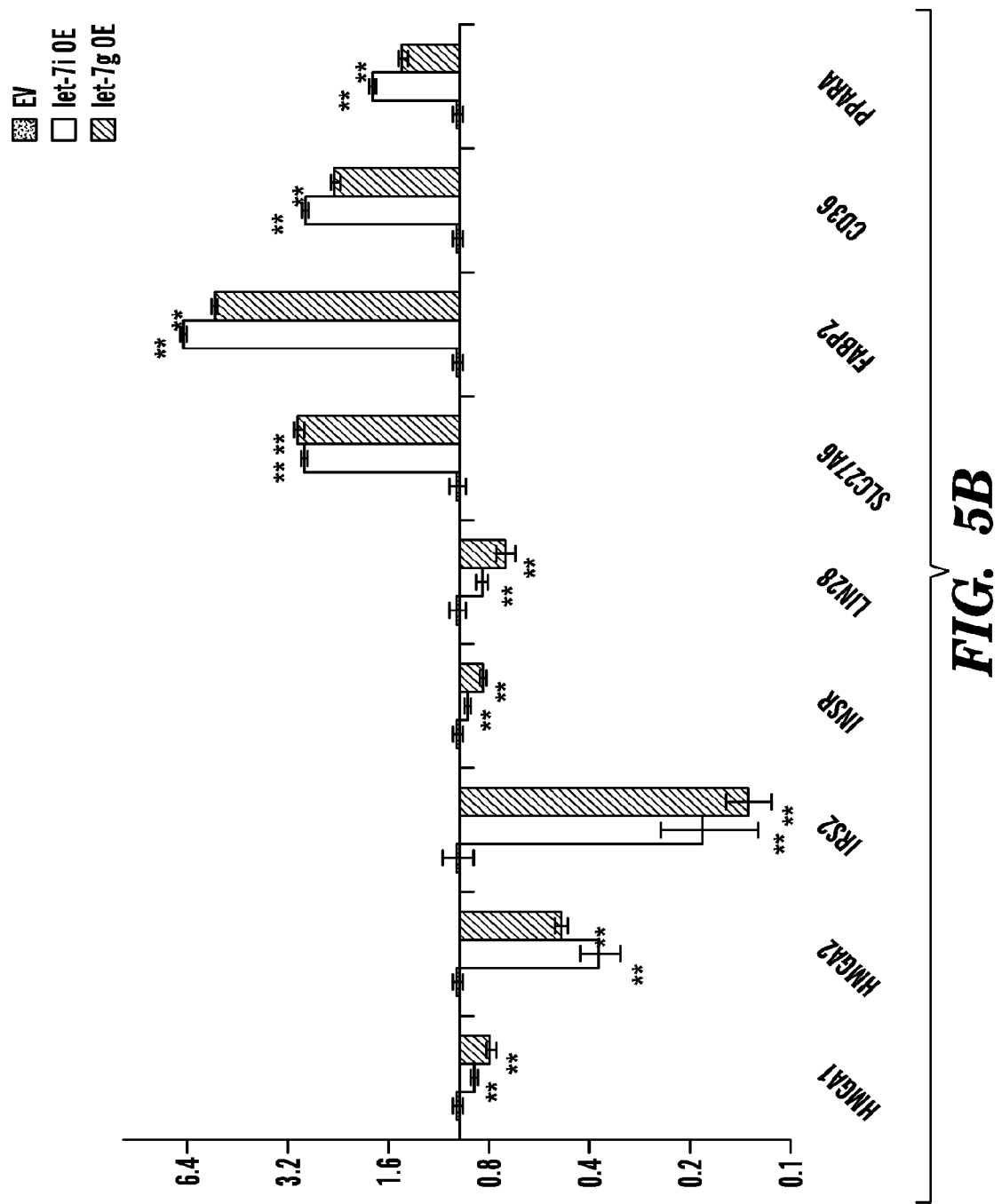
Figure 5C:
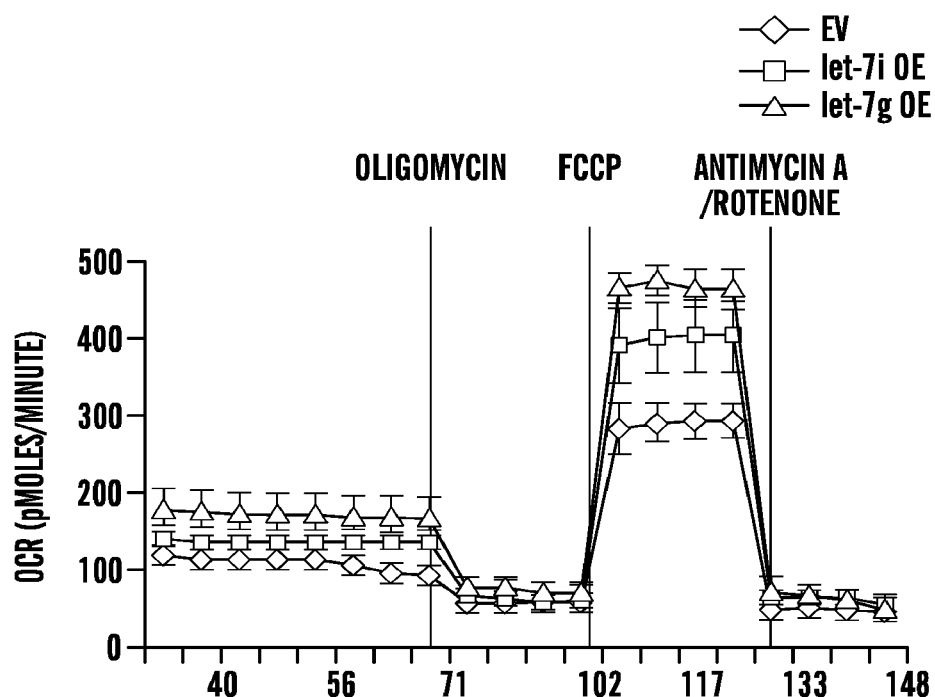
Figure 5D:
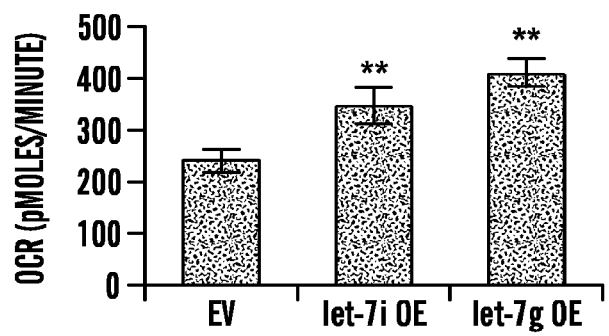
Figure 5E:
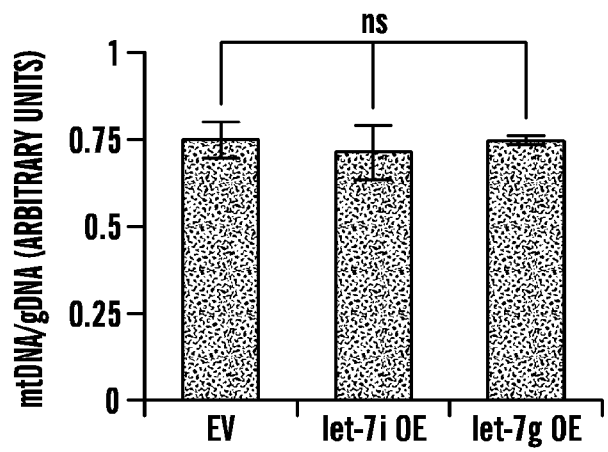
Figure 5F:
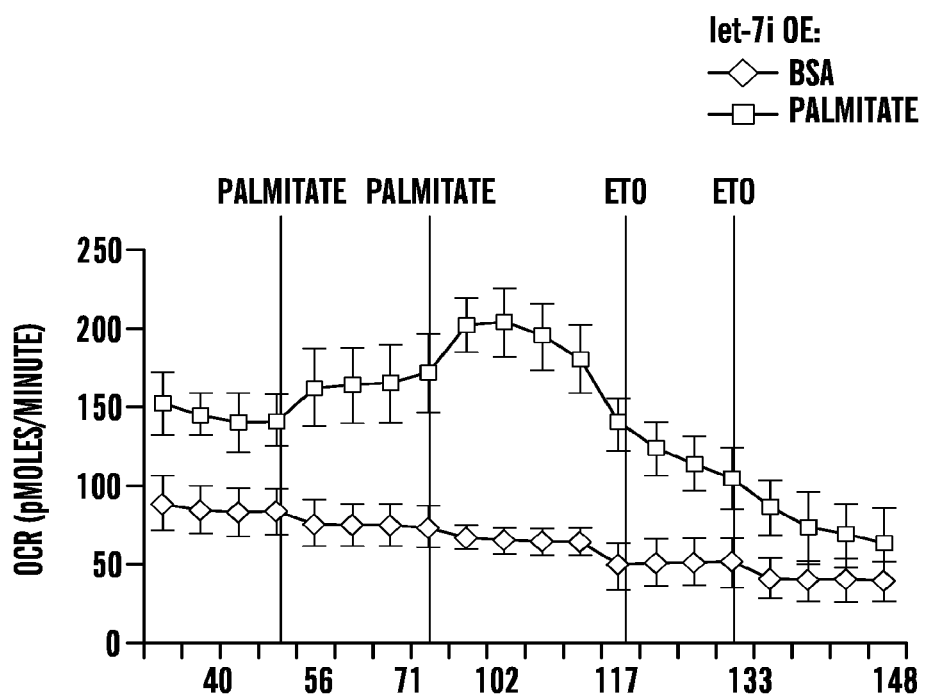
Figure 5G:
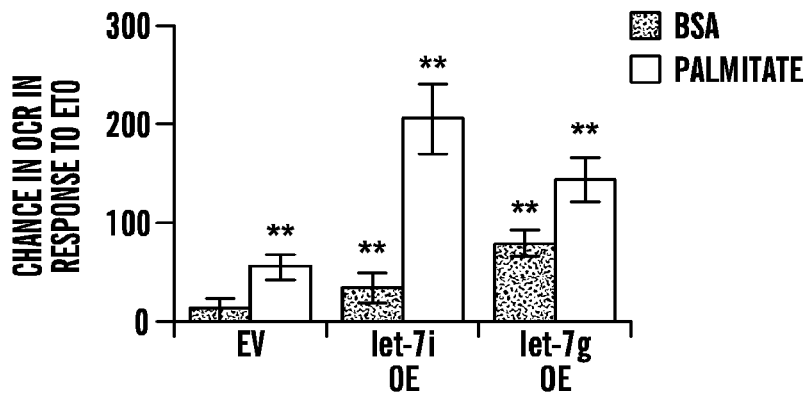
Figure 15A:
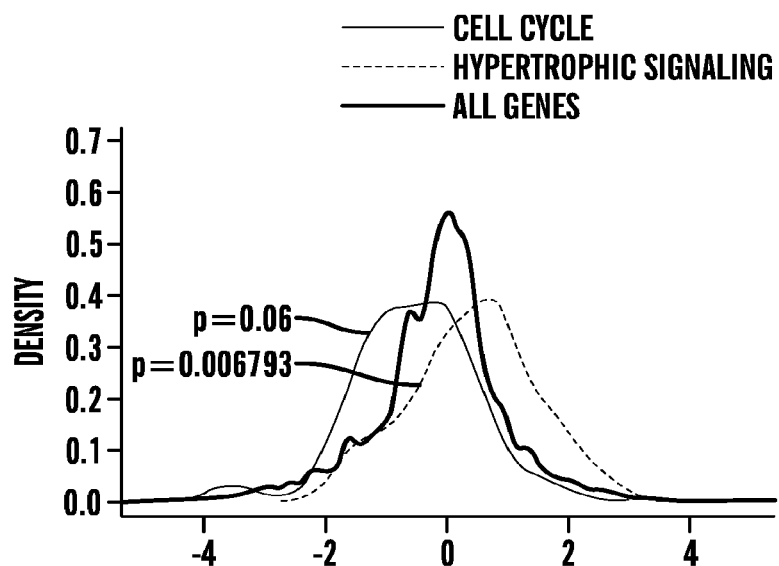
FIGS. 15A-15B Let-7 OE mimics gene expression profile observed during in vitro cardiac maturation. Density plots for representative categories of signaling pathways in let-7 OE CM samples. In each plot, black line indicates the entire gene set and the colored lines indicate the different categories.
Figure 15B:
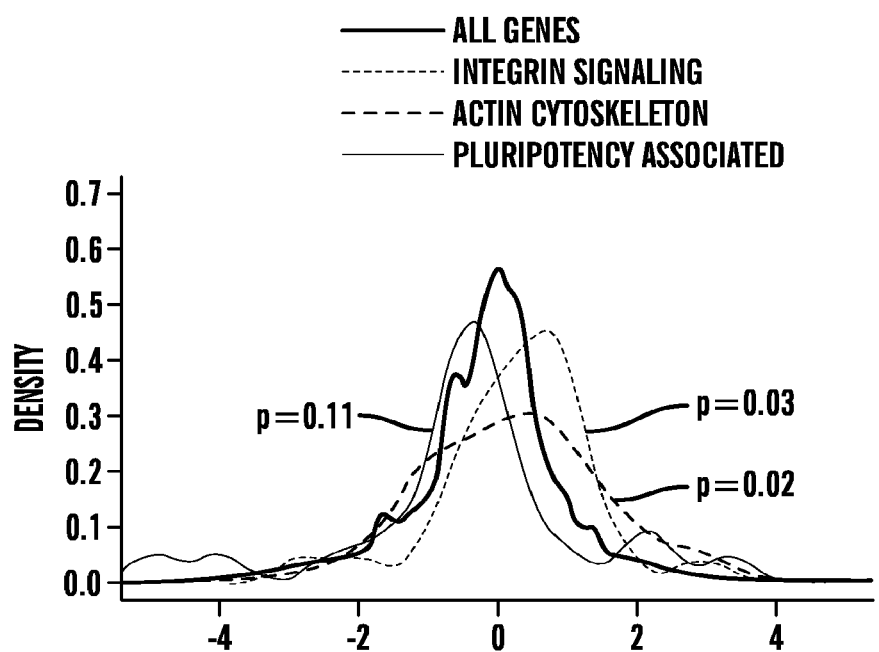
Figure 16A:
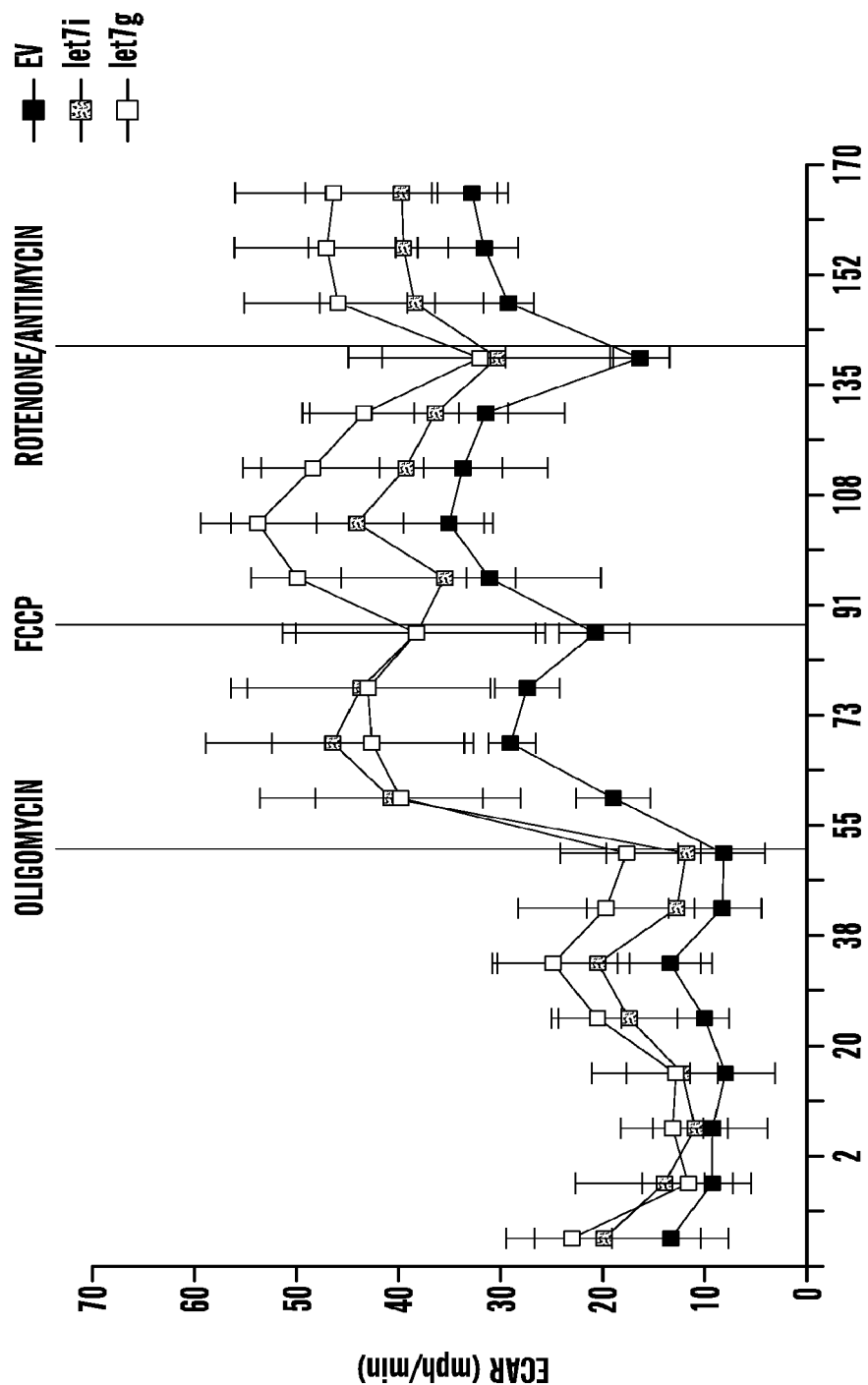
FIGS. 16A-16B Let-7 OE does not increase efficiency of glucose usage. Quantification of ECAR change in EV control and let-7 OE cardiomyocytes after (FIG. 16A) oligomycin addition in mito stress assay.
Figure 16B:
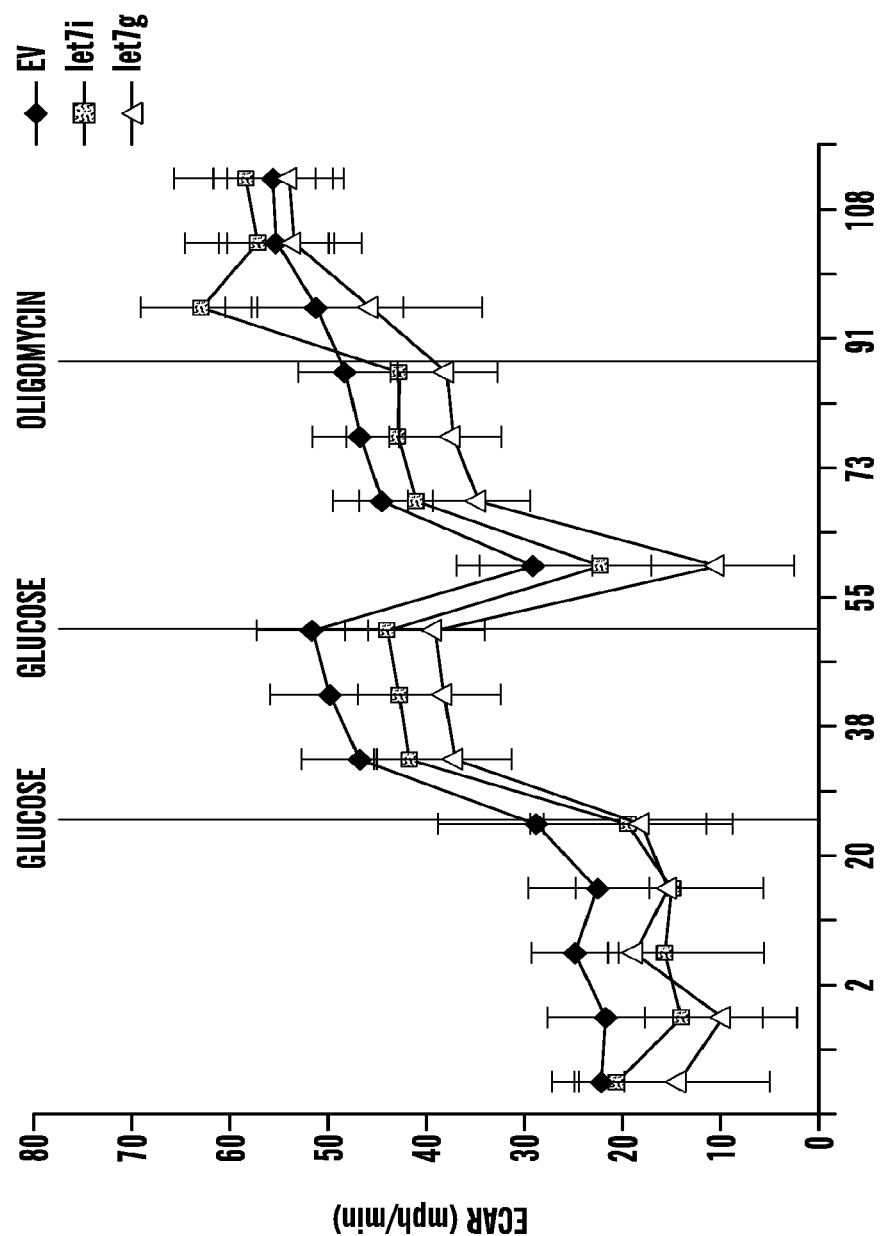

To understand the molecular signaling components of maturation program that are modulated in let-7g OE CMs, the inventors probed the differential expression data further using density plots for each of the 12 pathways previously identified (FIG. 4F). Pathways related to Ca$^{2+}$ signaling, G protein coupled receptor signaling, cAMP mediated signaling and cardiac beta adrenergic signaling and hypertrophic signaling were significantly up regulated in let-7 OE CMs similar to that seen in 1yr-CMs and fetal heart tissue samples (FIG. 4G and FIG. 15A). Importantly, FA metabolism rates were significantly up-regulated whereas PI3/AKT/Insulin signaling was significantly down-regulated in the let-7g OE CMs in comparison to EV control (FIG. 5A). However, programs related to cell cycle, pluripotency, actin-cytoskeleton and integrin signaling, while not significantly changed, showed the right trends (FIGS. 15A-15B). The inverse relationship between FA metabolism and PI3/AKT/insulin signaling in let-7g OE CMs was similar to that observed in the 1 yr old CMs and consistent with the metabolic switch seen in maturing CMs in in vivo studies. The inventors validated by qPCR in the let-7 OE CMs the down-regulation of candidate let-7 targets in the insulin pathway and up-regulation of candidates of FA metabolism (FIG. 5B). To test the functional relevance for these gene expression changes, the inventors carried out metabolic analysis of let-7 OE CMs vs. EV control using the SEA HORSE™ metabolic flux assay. First, mitochondrial maximal respiration capacity was analyzed by measuring the oxygen consumption rate (OCR), a metabolic parameter representing the mitochondrial respiration levels. To record the maximum activity of the electron transport chain uncoupled from ATP synthesis, mitochondrial ATP synthase was inhibited with oligomycin, then maximum mitochondrial respiration was measured after addition of the proton gradient discharger, carbonyl cyanide 4-(trifluoromethoxy)phenylhydrazone (FCCP). The OCR changes were significantly greater after FCCP treatment in let-7i OE and let-7g OE CMs compared to EV control samples (FIGS. 5C, 5D). Increased mitochondrial respiration can be due to increased mitochondrial copy number or increased mitochondrial activity, for example due to higher efficiency of glucose or fatty acid usage as energy substrates. The inventors determined mitochondrial genome copy number by qPCR and found that let-7 OE had no effect on this parameter (FIG. 5E). Interestingly, a fatty acid stress test using palmitate revealed that the let-7g OE and let-7i OE CMs have greater OCR increase in response to palmitate than EV control (FIG. 5F, 5G). To investigate whether the let-7 OE CMs also utilize glucose more efficiently, the extracellular acidification rate (ECAR) was determined. No significant difference was observed in the maximum ECAR change after adding oligomycin in the glucose stress assay for let-7 OE compared to EV control (FIG. 16). These experiments clearly indicate that let-7 OE specifically increases the efficiency of palmitate usage, which is an important sign of maturation. Together these data indicate that let-7 family of miRNA likely induces in vitro CM maturation in part by promoting a higher utilization of fatty acid to meet their increased energy demands.

REFERENCES

1. Snir, M. et al. Assessment of the ultrastructural and proliferative properties of human embryonic stem cell-derived cardiomyocytes. Am J Physiol Heart Circ Physiol 285, H2355-2363 (2003).
2. Robertson, C., Tran, D. D. & George, S. C. Concise review: maturation phases of human pluripotent stem cell-derived cardiomyocytes. Stem cells 31, 829-837 (2013).
3. Burridge, P. W., Keller, G., Gold, J. D. & Wu, J. C. Production of de novo cardiomyocytes: human pluripotent stem cell differentiation and direct reprogramming. Cell Stem Cell 10, 16-28 (2012).
4. Laflamme, M. A. et al. Cardiomyocytes derived from human embryonic stem cells in pro-survival factors enhance function of infarcted rat hearts. Nat Biotechnol 25, 1015-1024 (2007).
5. Beqqali, A., Kloots, J., Ward-van Oostwaard, D., Mummery, C. & Passier, R. Genome-wide transcriptional profiling of human embryonic stem cells differentiating to cardiomyocytes. Stem cells 24, 1956-1967 (2006).
6. Davis, R. P., van den Berg, C. W., Casini, S., Braam, S. R. & Mummery, C. L. Pluripotent stem cell models of cardiac disease and their implication for drug discovery and development. Trends in molecular medicine 17, 475-484 (2011).
7. Cao, F. et al. Transcriptional and functional profiling of human embryonic stem cell-derived cardiomyocytes. PloS one 3, e3474 (2008).
8. Yang, X., Pabon, L. & Murry, C. E. Engineering adolescence: maturation of human pluripotent stem cell-derived cardiomyocytes. Circ Res 114, 511-523 (2014).
9. Lundy, S. D., Zhu, W. Z., Regnier, M. & Laflamme, M. A. Structural and functional maturation of cardiomyocytes derived from human pluripotent stem cells. Stem cells and development 22, 1991-2002 (2013).
10. Mihic, A. et al. The effect of cyclic stretch on maturation and 3D tissue formation of human embryonic stem cell-derived cardiomyocytes. Biomaterials 35, 2798-2808 (2014).
11. Kuppusamy, K. T., Sperber, H. & Ruohola-Baker, H. MicroRNA regulation and role in stem cell maintenance, cardiac differentiation and hypertrophy. Curr Mol Med 13, 757-764 (2013).
12. Espinoza-Lewis, R. A. & Wang, D. Z. MicroRNAs in heart development. Curr Top Dev Biol 100, 279-317 (2012).
13. Wilson, K. D. et al. Dynamic microRNA expression programs during cardiac differentiation of human embryonic stem cells: role for miR-499. Circ Cardiovasc Genet 3, 426-435 (2010).
14. Gan, L., Schwengberg, S. & Denecke, B. MicroRNA profiling during cardiomyocyte-specific differentiation of murine embryonic stem cells based on two different miRNA array platforms. PloS one 6, e25809 (2011).
15. Tulloch, N. L. et al. Growth of engineered human myocardium with mechanical loading and vascular coculture. Circ Res 109, 47-59 (2011).
16. Chong, J. J. et al. Progenitor cells identified by PDGFR-alpha expression in the developing and diseased human heart. Stem cells and development 22, 1932-1943 (2013).
17. Fearnley, C. J., Roderick, H. L. & Bootman, M. D. Calcium signaling in cardiac myocytes. Cold Spring Harb Perspect Biol 3, a004242 (2011).
18. Lopaschuk, G. D., Ussher, J. R., Folmes, C. D., Jaswal, J. S. & Stanley, W. C. Myocardial fatty acid metabolism in health and disease. Physiol Rev 90, 207-258 (2010).
19. van der Vusse, G. J., van Bilsen, M. & Glatz, J. F. Cardiac fatty acid uptake and transport in health and disease. Cardiovasc Res 45, 279-293 (2000).
20. DeBosch, B. J. & Muslin, A. J. Insulin signaling pathways and cardiac growth. Journal of molecular and cellular cardiology 44, 855-864 (2008).
21. Ahuja, P., Sdek, P. & MacLellan, W. R. Cardiac myocyte cell cycle control in development, disease, and regeneration. Physiol Rev 87, 521-544 (2007).
22. Foldes, G. et al. Modulation of human embryonic stem cell-derived cardiomyocyte growth: a testbed for studying human cardiac hypertrophy? Journal of molecular and cellular cardiology 50, 367-376 (2011).
23. Brodsky, V., Chernyaev, A. L. & Vasilyeva, I. A. Variability of the cardiomyocyte ploidy in normal human hearts. Virchows Arch B Cell Pathol Incl Mol Pathol 61, 289-294 (1991).
24. Olivetti, G. et al. Aging, cardiac hypertrophy and ischemic cardiomyopathy do not affect the proportion of mononucleated and multinucleated myocytes in the human heart. Journal of molecular and cellular cardiology 28, 1463-1477 (1996).
25. Kellogg, D. R. Wee 1-dependent mechanisms required for coordination of cell growth and cell division. J Cell Sci 116, 4883-4890 (2003).
26. Opie, L. H. Metabolism of the heart in health and disease. 3. Am Heart J 77, 383-410 (1969).
27. Rodriguez, M. L., Graham, B. T., Pabon, L. M., Han, S. J., Murry, C. E., Sniadecki, N. J. Measuring the contractile forces of human induced pluripotent stem cell-derived cardiomyocytes with arrays of microposts. Journal of Biomechanical Engineering, In Press (2014).
28. Kllegman, R. M., Stanton, B. F., Schor, N. F., Gerne, J. W., Behrman, R. E. 1529-1536 (2012).
29. Xu, X. Q., Soo, S. Y., Sun, W. & Zweigerdt, R. Global expression profile of highly enriched cardiomyocytes derived from human embryonic stem cells. Stem cells 27, 2163-2174 (2009).
30. Jones, D., Ruzzo, W. L. Isolator: analysis of splicing and transcription in RNA-seq experiments. In preparation
31. Carley, A. N. & Kleinfeld, A. M. Fatty acid (FFA) transport in cardiomyocytes revealed by imaging unbound FFA is mediated by an FFA pump modulated by the CD36 protein. The Journal of biological chemistry 286, 4589-4597 (2011).
32. Gomes, A. V. et al. Cardiac troponin T isoforms affect the Ca(2+) sensitivity of force development in the presence of slow skeletal troponin I: insights into the role of troponin T isoforms in the fetal heart. The Journal of biological chemistry 279, 49579-49587 (2004).
33. Denzel, M. S. et al. T-cadherin is critical for adiponectin-mediated cardioprotection in mice. The Journal of clinical investigation 120, 4342-4352 (2010).

34. Lopaschuk, G. D. & Jaswal, J. S. Energy metabolic phenotype of the cardiomyocyte during development, differentiation, and postnatal maturation. J Cardiovasc Pharmacol 56, 130-140 (2010).
35. Zhu, H. et al. The Lin28/let-7 axis regulates glucose metabolism. Cell 147, 81-94 (2011).
36. Kim, C. et al. Studying arrhythmogenic right ventricular dysplasia with patient-specific iPSCs. Nature 494, 105-110 (2013).
37. Worringer, K. A. et al. The let-7/LIN-41 Pathway Regulates Reprogramming to Human Induced Pluripotent Stem Cells by Controlling Expression of Prodifferentiation Genes. Cell Stem Cell 14, 40-52 (2014).
38. McMahon, A. P., Champion, J. E., McMahon, J. A. & Sukhatme, V. P. Developmental expression of the putative transcription factor Egr-1 suggests that Egr-1 and c-fos are coregulated in some tissues. Development 108, 281-287 (1990).
39. Wang, C., Dostanic, S., Servant, N. & Chalifour, L. E. Egr-1 negatively regulates expression of the sodium-calcium exchanger-1 in cardiomyocytes in vitro and in vivo. Cardiovasc Res 65, 187-194 (2005).
40. Chang, H. M. et al. Trim71 cooperates with microRNAs to repress Cdkn1a expression and promote embryonic stem cell proliferation. Nat Commun 3, 923 (2012).
41. La Torre, A., Georgi, S. & Reh, T. A. Conserved microRNA pathway regulates developmental timing of retinal neurogenesis. Proceedings of the National Academy of Sciences of the United States of America 110, E2362-2370 (2013).

In this study, for the first time, the inventors demonstrate that let-7 family miRNAs promote the maturation of hESC derived CMs. A wide range of functional, physiological and molecular parameters indicate that members of the let-7 family can significantly enhance a number of functional properties relevant to CM maturation. Previous in vivo studies have shown that CMs start utilizing fatty acid as their main source of energy when they transition from fetal to postnatal state[34]. However, this is the first study to demonstrate a similar metabolic switch in CMs matured in vitro and also specifies let-7 family miRNAs to be critical in this switch. Overexpression of let-7g and let-7i specifically accelerates the CM's capacity to utilize fatty acid as a major energy source without affecting the mitochondrial copy number or improving the efficiency of glycolysis. Since these metabolic and functional changes mimic changes during postnatal maturation, and without wishing to be bound by theory, the inventors posit that induction of let-7 in young CMs results in changes that are equivalent to physiological hypertrophy[34]. To further dissect the mechanism of let-7 function in this process the inventors identified several known let-7 targets from the PI3/AKT/insulin pathway[35] to be significantly down-regulated during CM maturation and let-7 OE. Repression of the PI3/AKT/insulin pathway may accelerate the ability of the CMs to start using fatty acid as their predominant energy substrate. Kim et al.[36] (2013) for the first time showed that in order to establish an adult-onset disease model using patient-specific IPSC-derived CMs, it was necessary to first induce adult like metabolism in these cells by exogenously providing a lipid based cocktail. The present study has identified an endogenous molecule that can promote this metabolic transition and thus aid in studying iPSC derived CMs as disease models in an adult setting.

Figure 6:
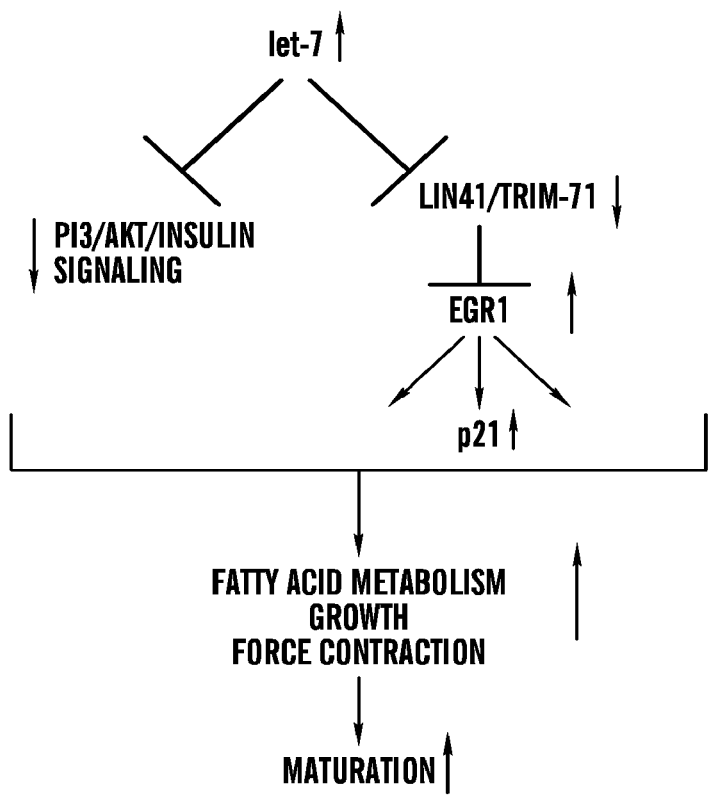
FIG. 6 Proposed model for let-7 action in in vitro hESC-CM maturation. Let-7 inhibits its targets from the PI3/AKT/Insulin pathway and TRIM-71/LIN-41. Inhibition of TRIM-71/LIN41 further results in the upregulation of EGR1. Down regulation of the insulin pathway and upregulation of EGR1 likely regulate multitude of genes that could culminate with increased FA metabolism, growth and force of contraction resulting in cardiac maturation. The arrows on the side of the each of the regulators indicate the direction of change when let-7 is induced.
Figure 7A:
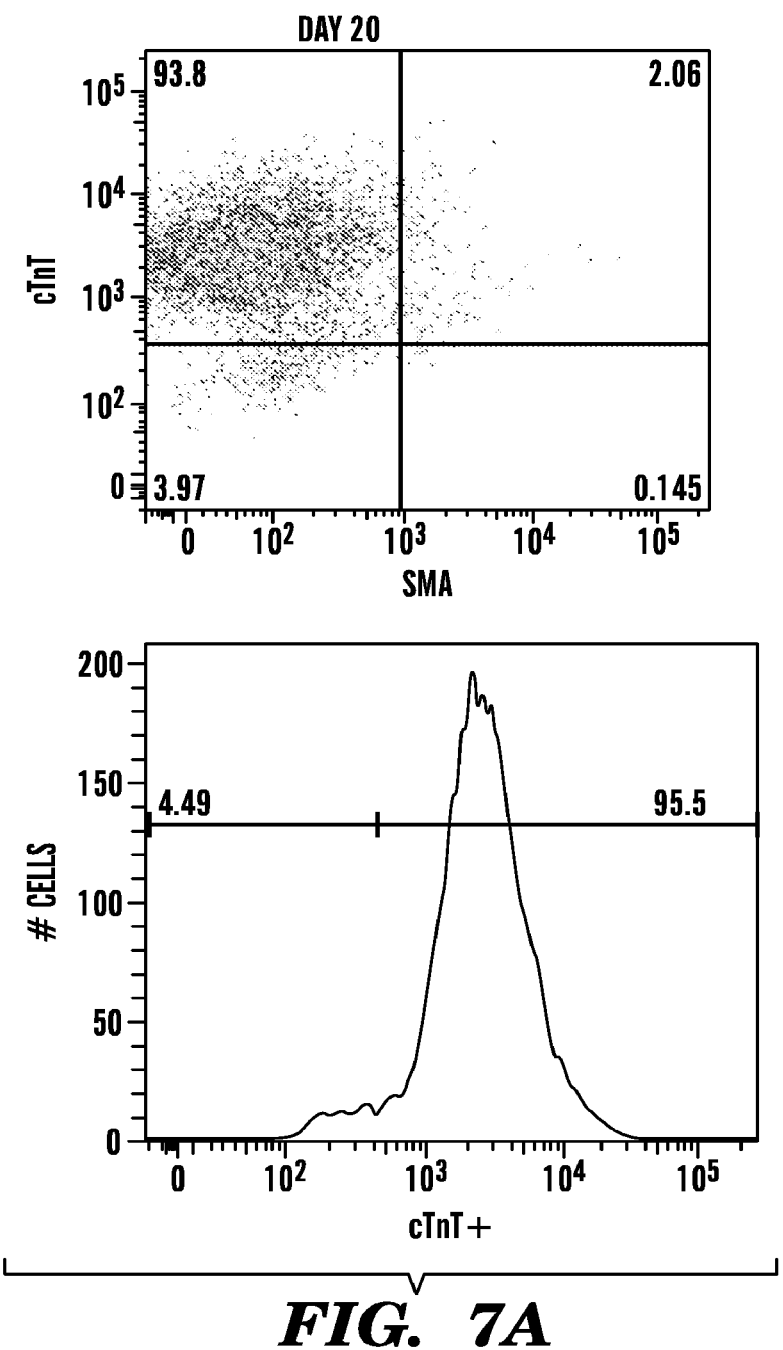
FIGS. 7A-7D Representative flow cytometry analysis of hESC-CMs at day 20 (FIGS. 7A, 7C), 1 yr old (FIG. 7B) cEHT (FIG. 7D) that demonstrated greater that 70% cardiac purity. cTnT: Cardiac troponin T; SMA: Smooth muscle actin.
Figure 7B:
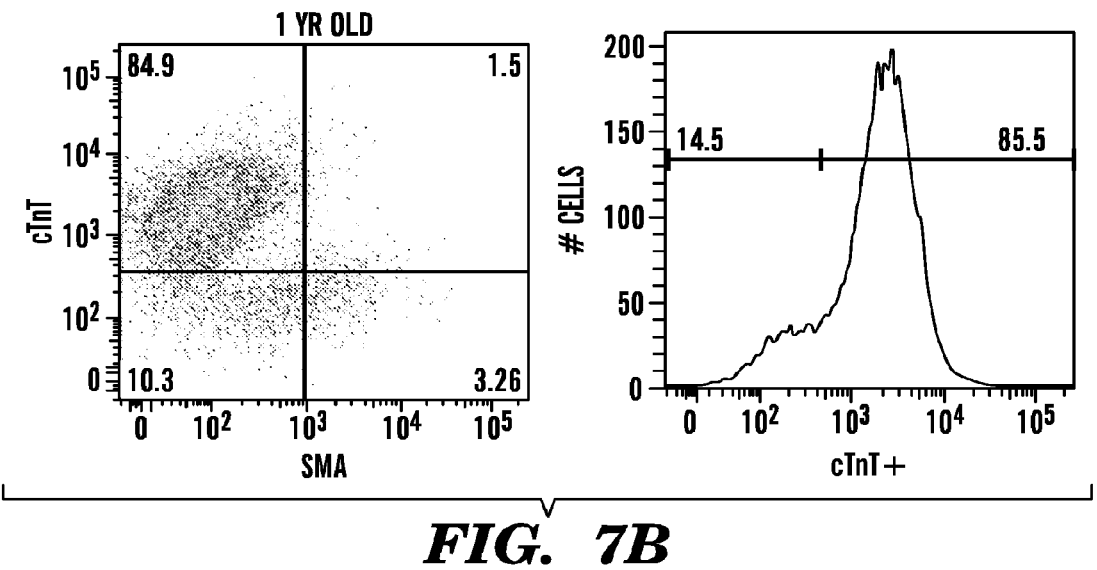
Figure 7C:
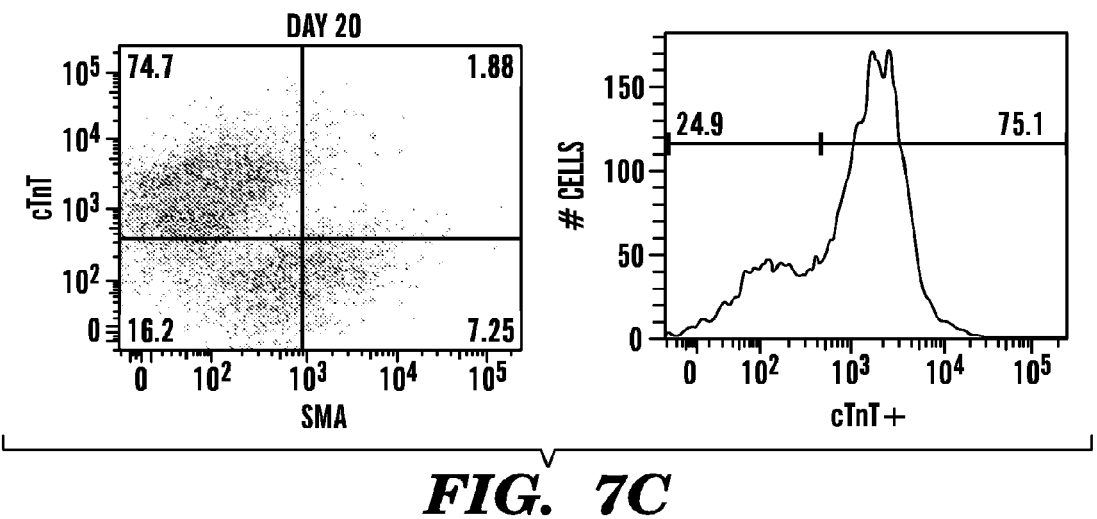
Figure 7D:
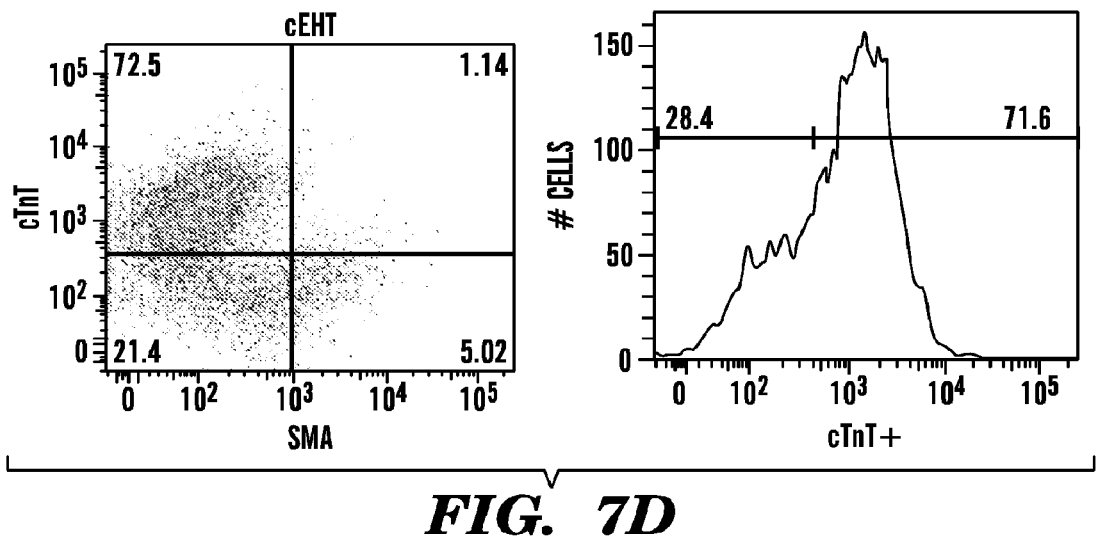
Figure 8A:
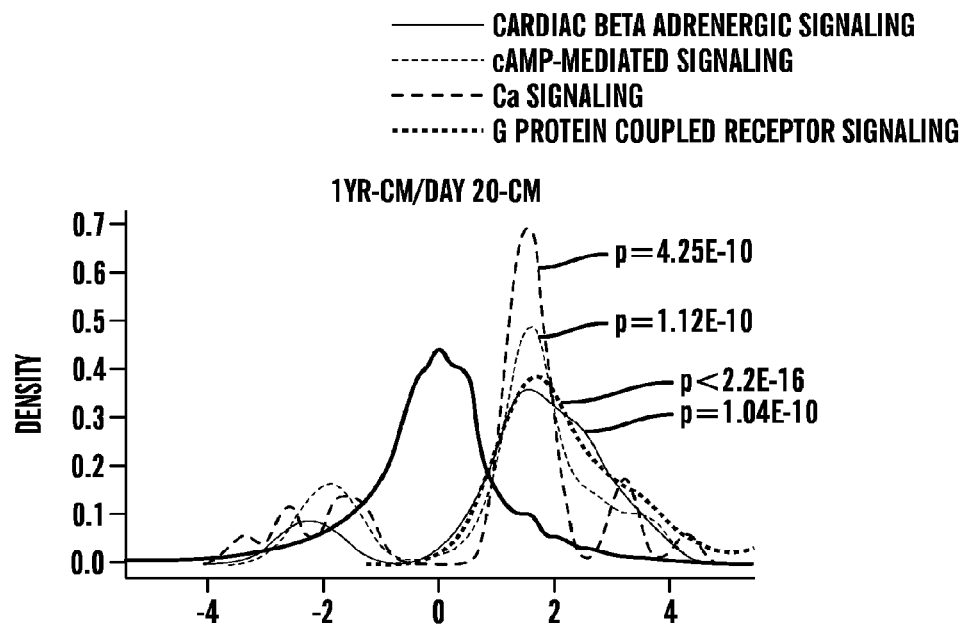
FIGS. 8A-8F Density plots generated using fold change expression (x-axis indicates $log_2$ fold change) of genes in 1 yr (FIGS. 8A, 8D), HFA (FIGS. 8B, 8E) and HFV (FIGS. 8C, 8F) relative to day 20 cardiomyocytes. Black line indicates the entire gene set and colored lines indicated various pathways.
Figure 8B:
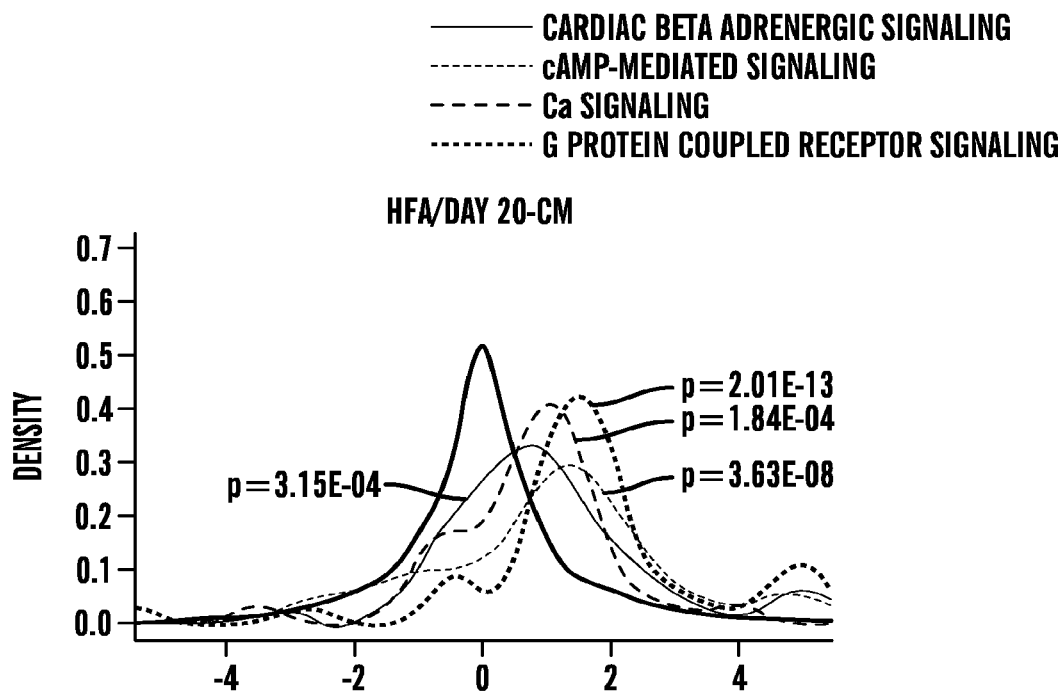
Figure 8C:
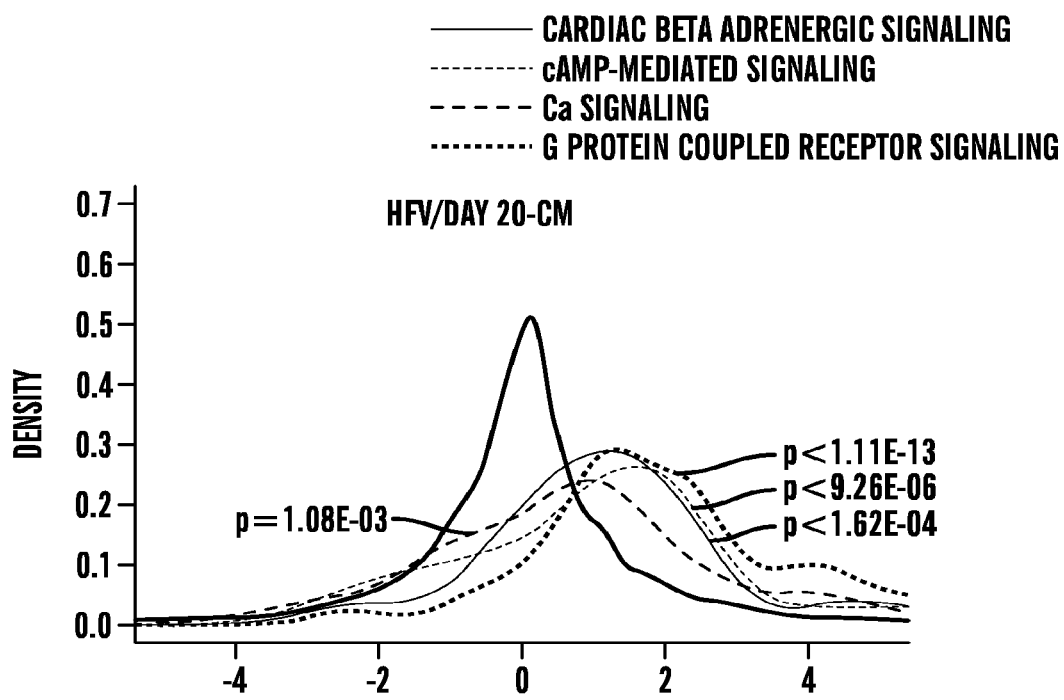
Figure 8D:
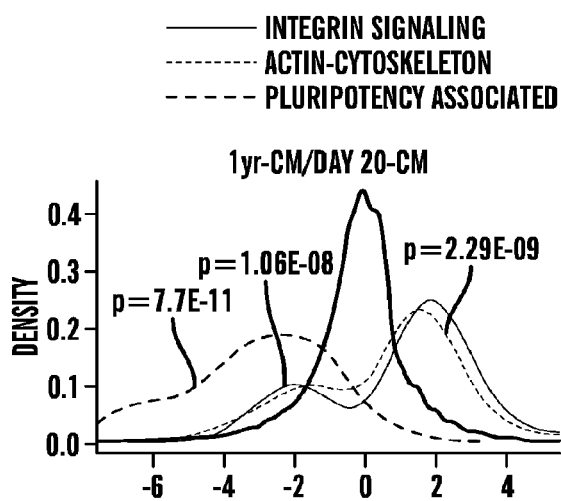
Figure 8E:
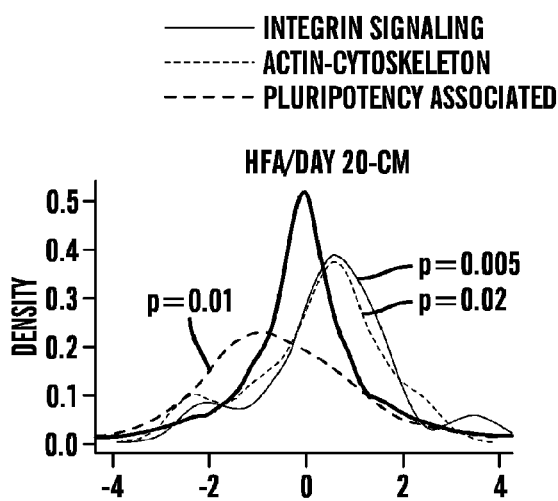
Figure 8F:
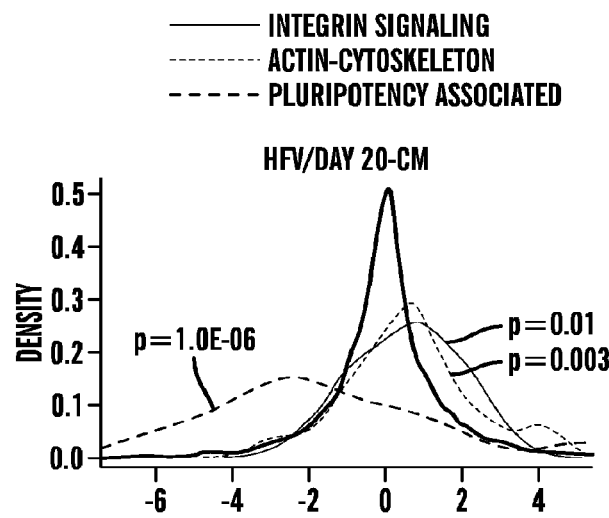
Figure 17:
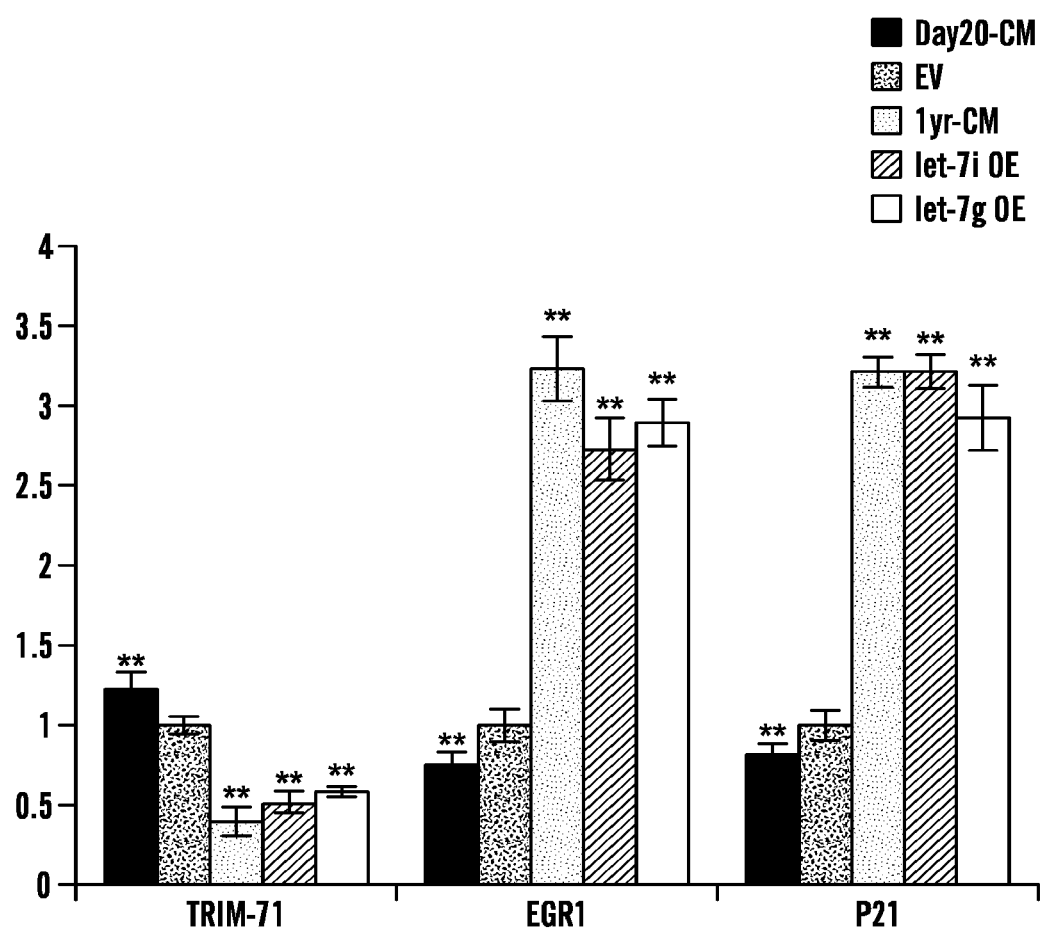
FIG. 17 Let-7 regulates multiple pathways potentially important for cardiac maturation. qPCR verification to demonstrate that let-7 OE down-regulates TRIM71 and up-regulates EGR1 and p21.
Figure 18:
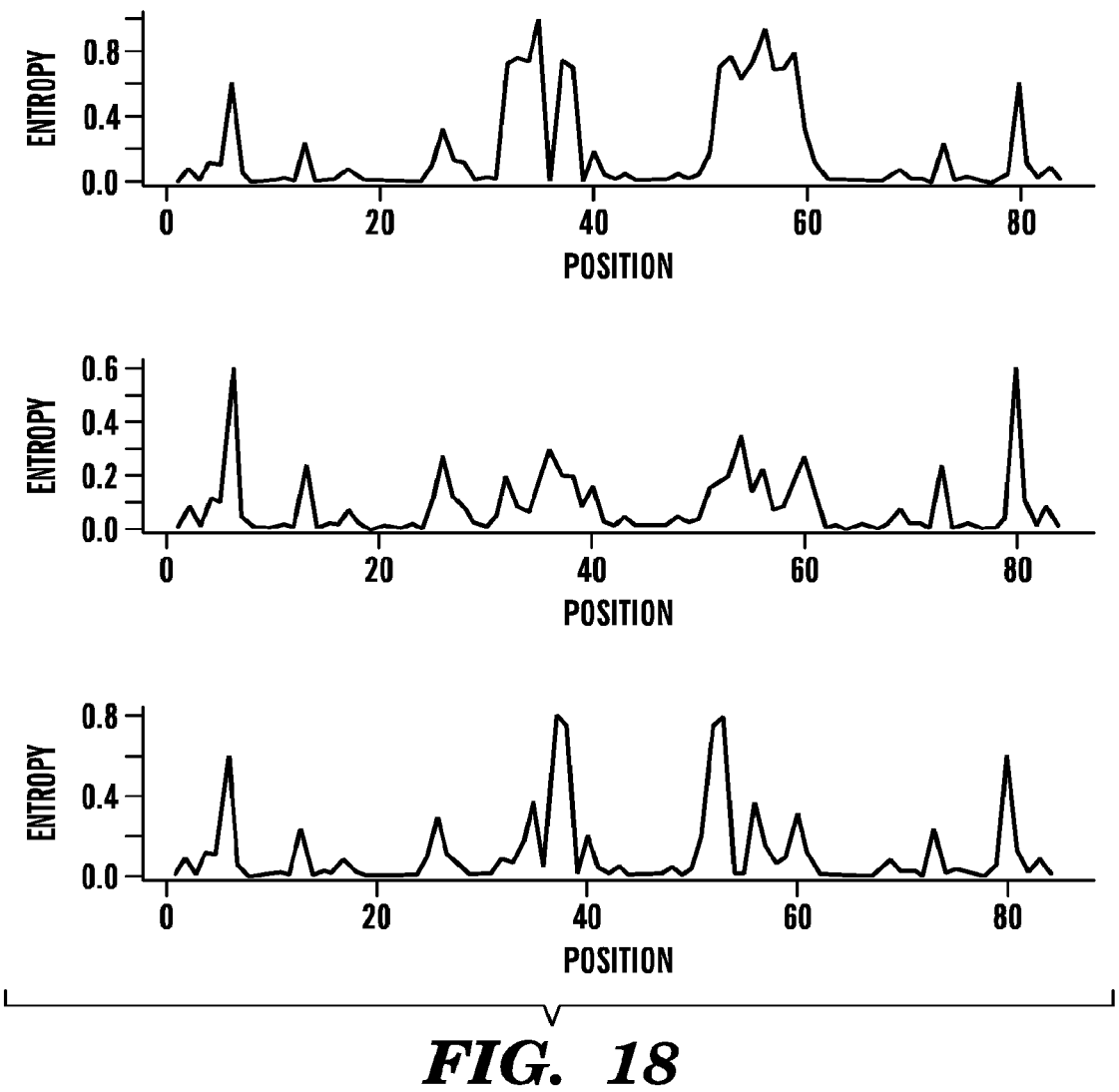
FIG. 18 shows modified versions of the hsa-let-7g (i.e., human) sequence designed by making mutations in the terminal loop region of the hsa-let-7g sequence in order to disrupt the GGAG motif (bold underscored) which has been identified as a LIN28 binding site (Nam et al. 2011). The mutations were specifically designed to make the hairpin structurally and thermodynamically as similar to the wild type hsa-let-7g as possible, making them different from previously published modified versions of let-7g, which were not thermodynamically optimized. Shown are two examples of such designs (version E and I). Mutation sites are identified in bold and enlarged text.
Figure 18:
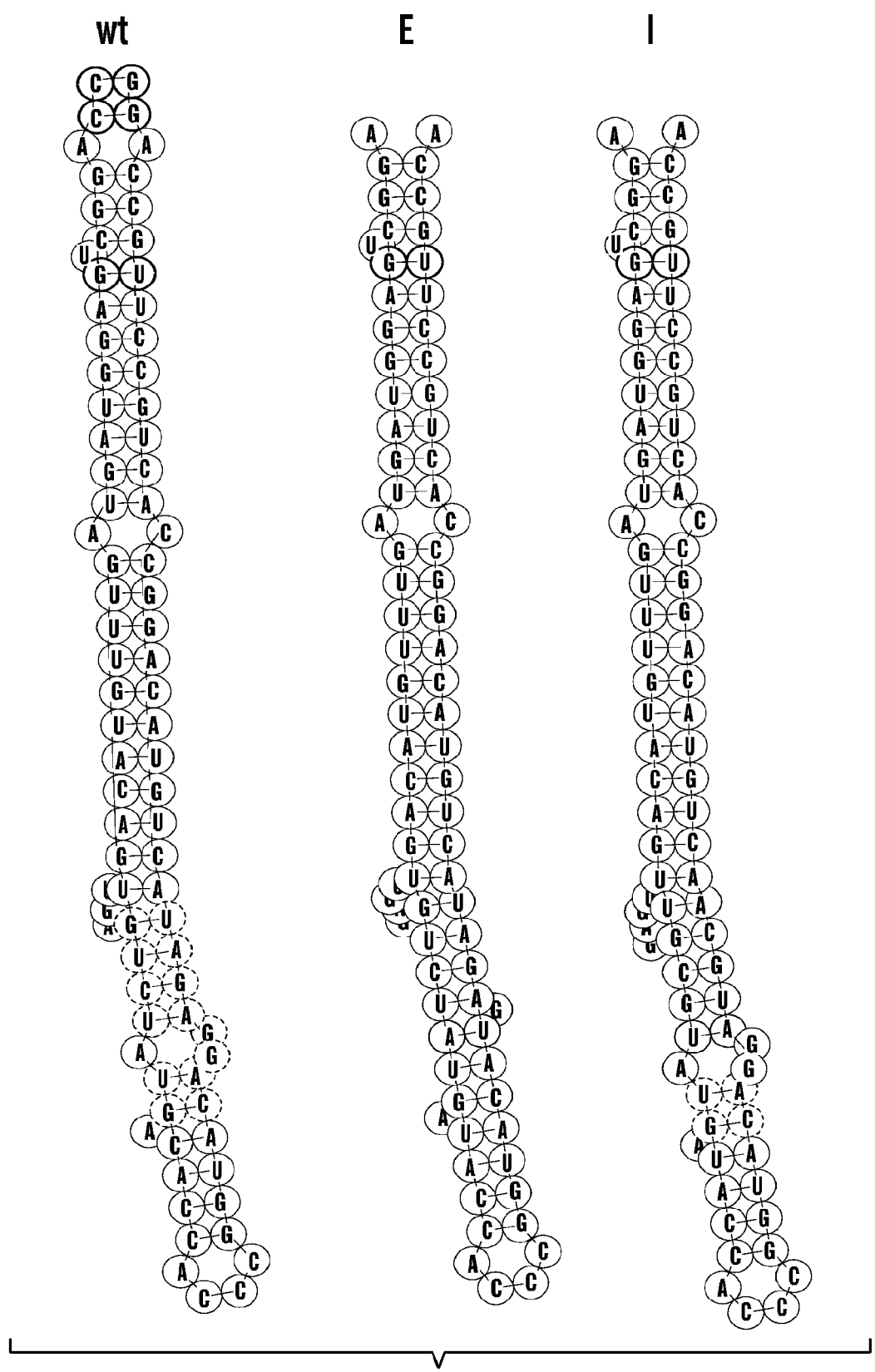
Figure 19A:
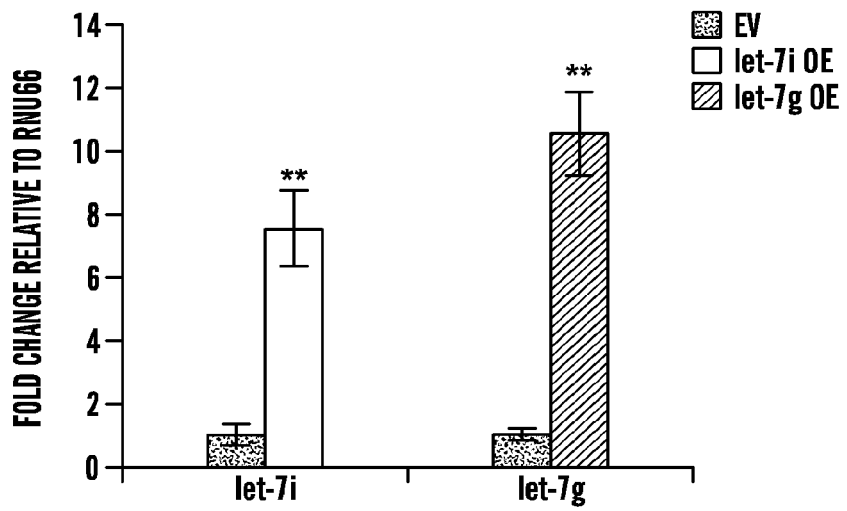
FIGS. 19A-19B show let-7 over-expression (OE) in IMR90 iPSC derived cardiomyocytes (IMR90 iPSC-CMs). A pLKO-lentiviral based system was used to overexpress let-7g and let-7i in IMR90-iPSC-CMs for up to 2 weeks.
Figure 19B:
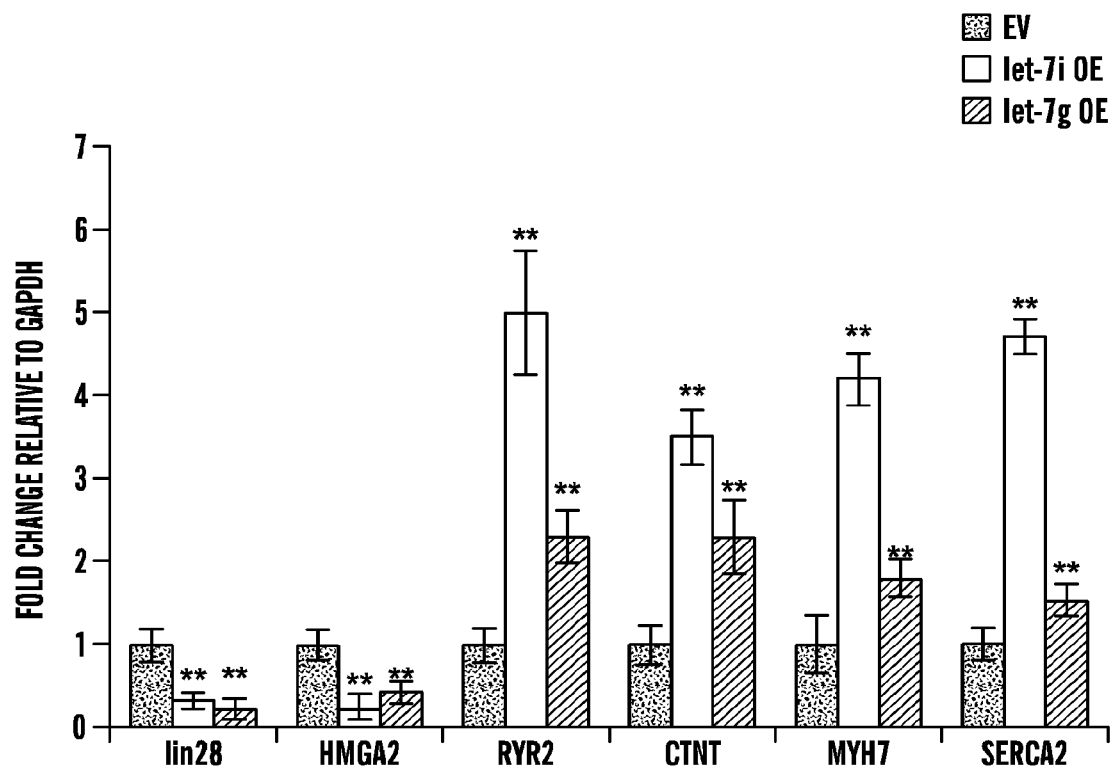
Figure 20A:
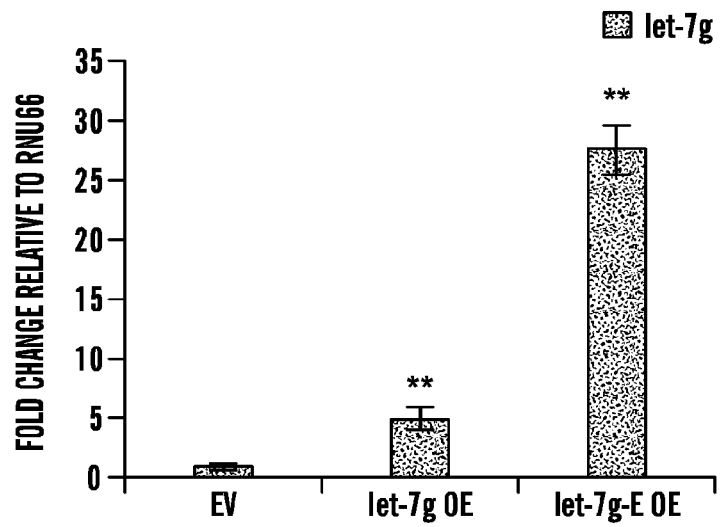
FIGS. 20A-20B Modified let-7g (let-7g-E) is more efficient in generating mature let-7g in HECT293FT cells. Let-7g and a modified version of let-7g (plko-let-7g-E) were induced in hect 293 FT cells by introducing plko-let-7g and plko-let-7g-E plasmids with lipofectamine transient transfection assay. 24 hrs after transfection, cells were tested for mature let-7g expression.
Figure 20B:
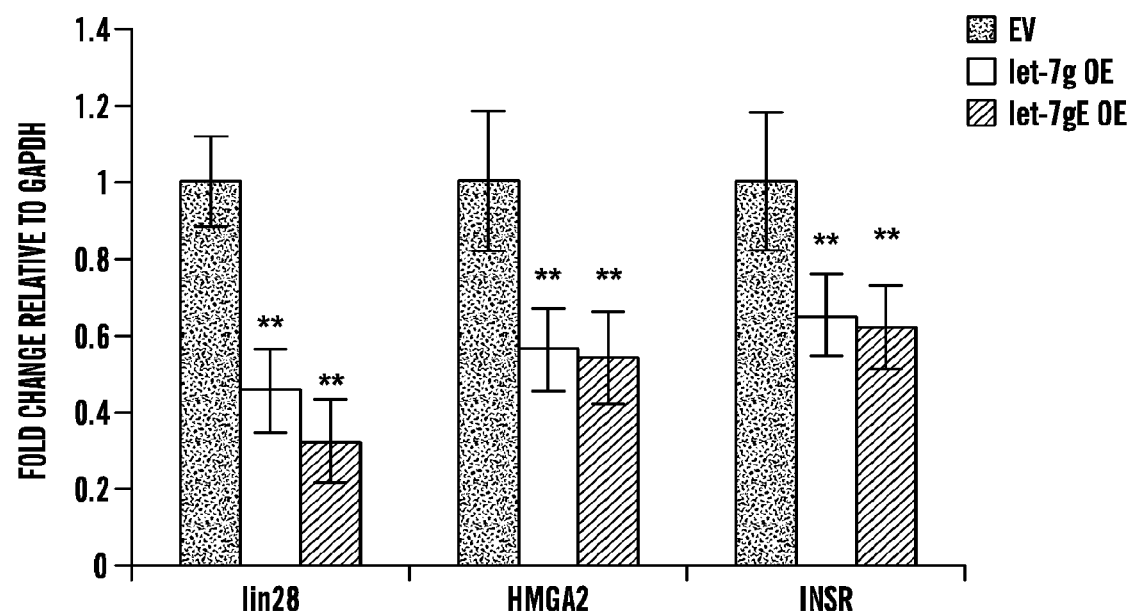
Figure 21A:
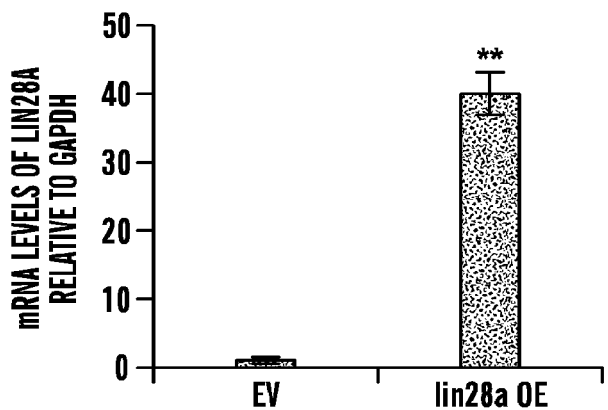
FIGS. 21A-21H Let-7 is required for hESC-CM maturation.
Figure 21B:
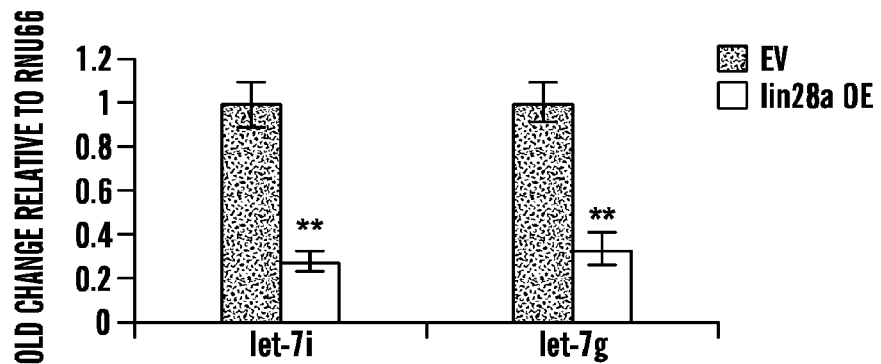
Figure 21C:
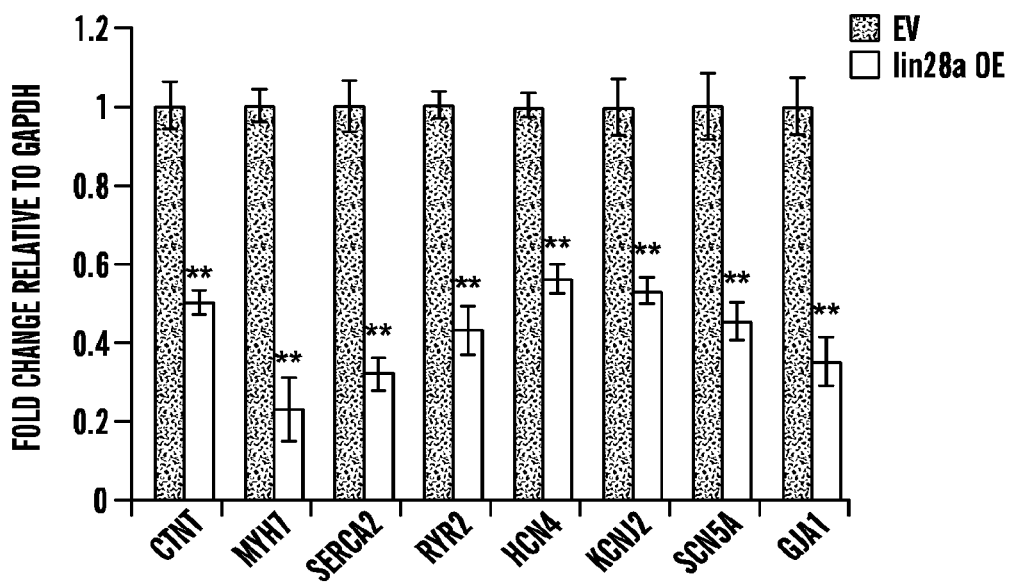
Figure 21D:
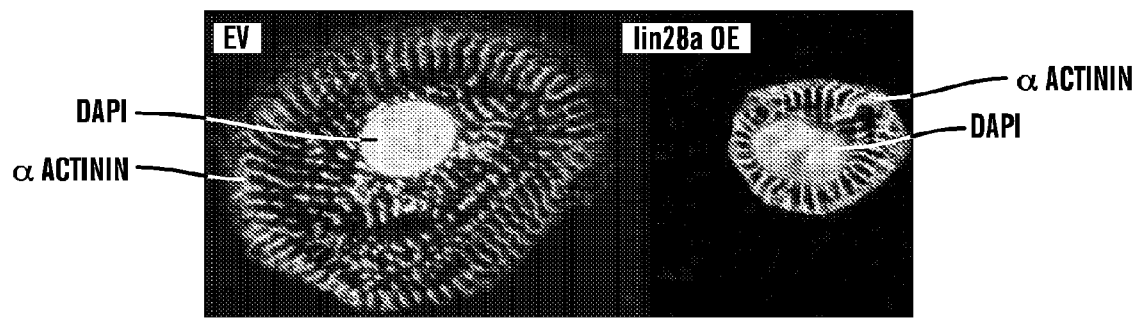
Figure 21E:
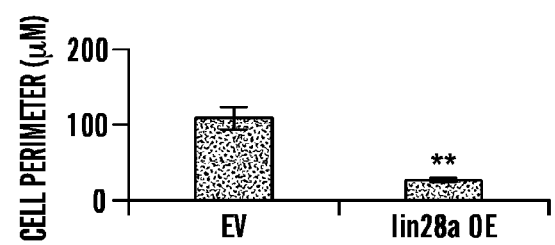
Figure 21F:
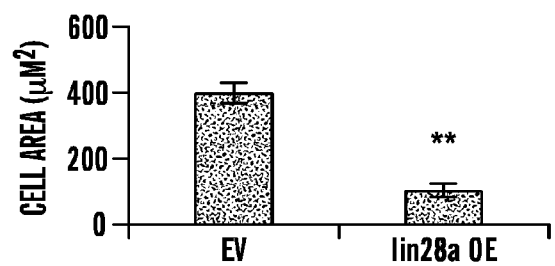
Figure 21G:
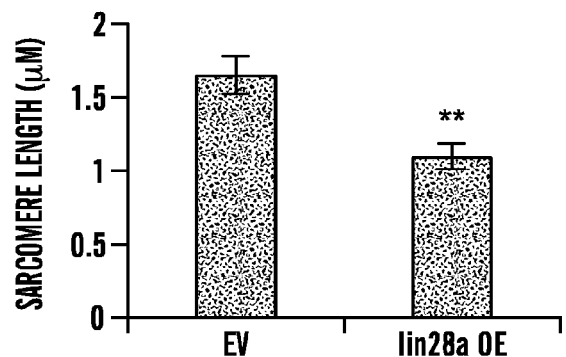
Figure 21H:
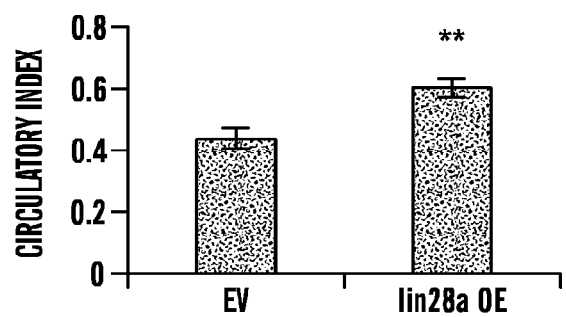
Figure 22A:
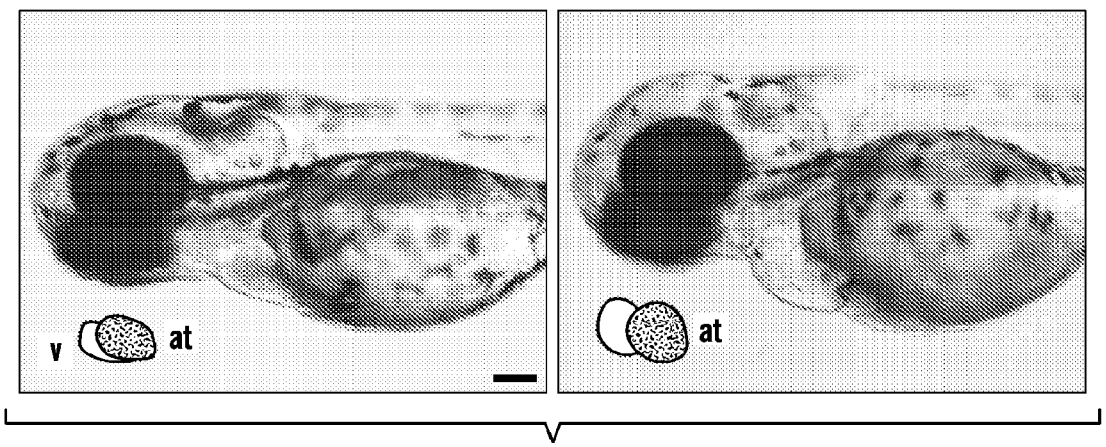
FIGS. 22A-22D Let-7 OE accelerates CM maturation.
Figure 22B:
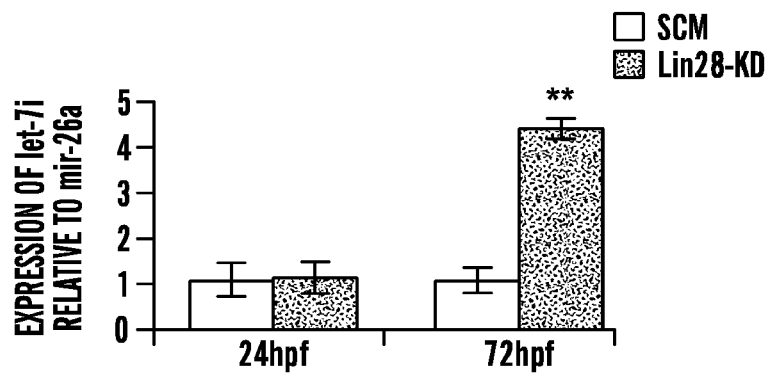
Figure 22C:
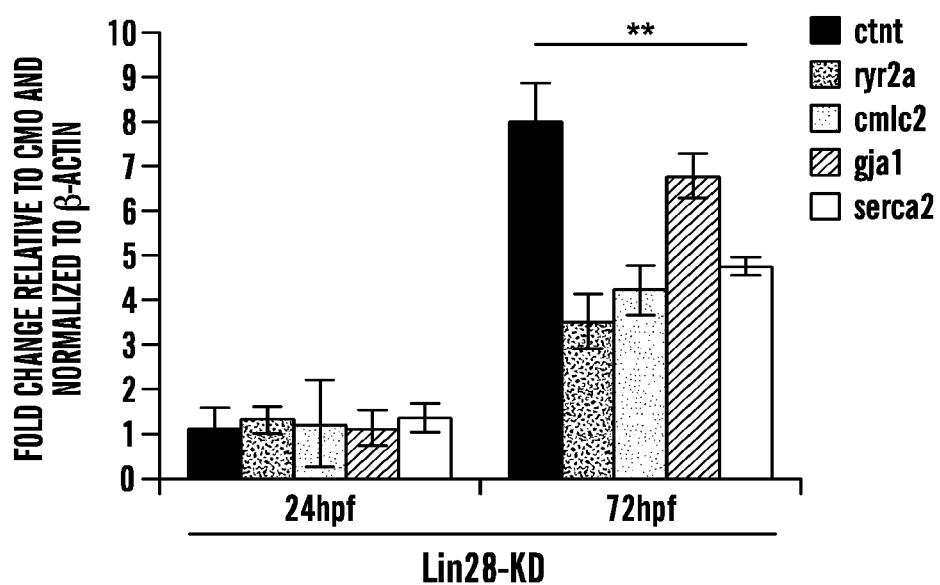
Figure 22D:
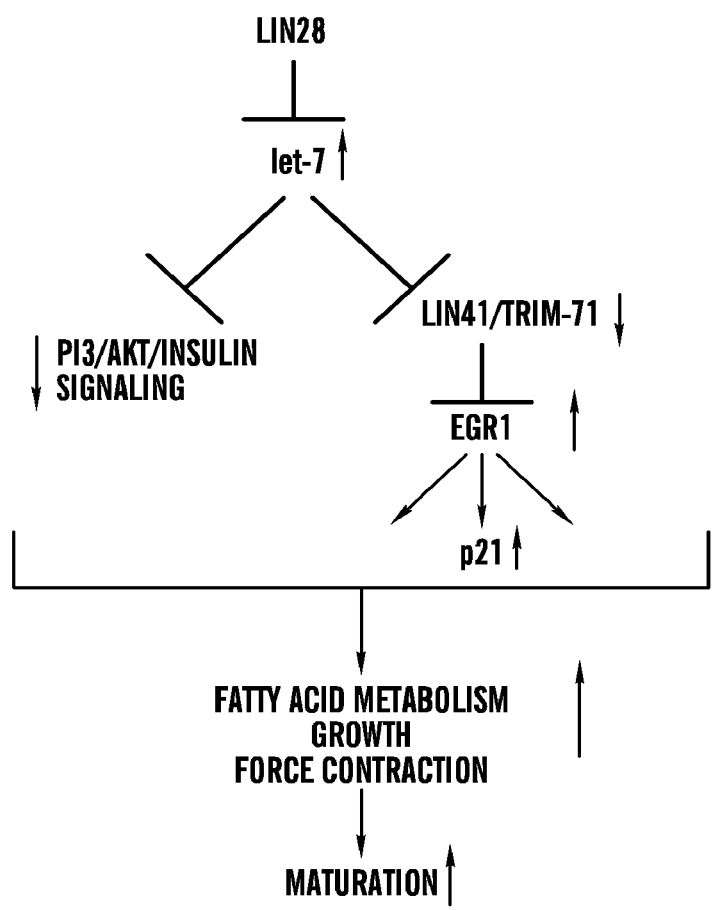

Maturation of CMs is complex and bound to be regulated by multiple pathways acting simultaneously. In this context, let-7 is well suited candidate as it regulates a multitude of other target genes that could potentially promote maturation. One such target is TRIM71/LIN41 that is repressed in both mature CMs as well as in let-7 OE CMs (Supplementary FIG. 11). Down-regulation of TRIM71/LIN41 is known to up-regulate a general differentiation transcription factor EGR1[37] that is shown to function in mature heart.[38, 39] In addition, TRIM71 down-regulation allows up-regulation of p21 (Cdkn1a), a repressor of G1 to S transition in cell cycle[40] which again is an indicator of cardiac maturation. Both EGR1 and p21 are significantly up regulated in let-7 OE CM (FIG. 17). Thus, let-7 function in CM maturation is an excellent example of microRNA's multipronged function as a developmental switch. Changes in both insulin signaling pathway and TRIM71 could play critical roles in the let-7 induced maturation process (FIG. 6).

Let-7 miRNA(s) can be combined with other approaches to establish cells that even more closely mimic mature human cardiomyocytes.

Example 5

Exemplary Materials and Methods

Cell Culture

Undifferentiated human embryonic stem cell (hESCs) lines H7 (NIHhESCC-10-0061) and RUES2 (NIHhESC-09-0013) were expanded using mouse embryonic fibroblast-conditioned medium with 5 ng/ml basic fibroblast growth factor. H7-CMs were derived using previously reported protocols[1-3]. RUES2-CMs were used for all functional analyses and these were derived using a cardiac progenitor cell differentiation protocol[4] derived from previously reported monolayer directed differentiation methods[1, 5, 6]. In brief, this involves the induction of a monolayer of hESCs with activin A and bone morphogenetic protein-4 (BMP4) under serum- and insulin-free conditions. During the early stages of differentiation, the cells were also exposed to the Wnt agonist CHIR 99021 followed by the Wnt antagonist Xav939. From 7 days of in vitro differentiation, the cells were fed every alternate day with serum-free RPMI-B27 plus insulin media. After 20 days of in vitro differentiation, the cells were trypsinized and replated. Only those cell preparations that had at least 70% cardiac troponin T-positive CMs (as observed by flow cytometry) were used for further experiments. For experiments where the H7-CMs were cultured for around a year, the cells were replated after the $3^{rd}$ and 11th month from day 0. At the $11^{th}$ month, FACS analysis for cTnT was conducted and the CMs were split into three parts and were cultured as three independent replicates for another 1.5 months after which they were harvested for RNA extraction. IMR90iPSC-CMs cultured for 1 yr were replated at day 20 and split every 2 months for 12 months before harvesting for RNA extraction. To generate engineered cardiac tissue, the inventors used the procedure reported by Tulloch et al.[2] In brief, day 20 CMs are suspended in the collagen gel at 10,000/μl, and rod-shaped constructs of 25 μl (1 mm radius×8 mm length) were generated by casting in a preformed mold and warming to 37° C. The ends of the mold contain Velcro-like micro-fiber loops, and these become impregnated with gel+cell mixture. These tabs allow the constructs to be maintained under static tension, which facilitates alignment and differentiation of the CMs. The constructs were maintained in the serum-free RPMI-B27 plus glutamine media up to 2 weeks. For let-7 overexpression analysis, the CMs were transduced with the virus carrying the pLKO-let-7 or empty vector control pLKO plasmid at day 12 of the directed differentiation protocol. After overnight transduction the virus was removed, cells were rinsed with PBS and new media added. The samples were analyzed at day 30 from the initiation of differentiation.

Immunocytochemistry and Morphological Analysis

All morphological analyses were carried out using at least 50 cells. Cells replated in chamber slides were fixed in 4% paraformaldehyde for 15 minutes followed by PBS wash. The fixed cells were blocked for an hour with 1.5% normal goat serum and incubated O/N with mouse alpha actinin (sigma) primary antibody. The primary antibody was rinsed with PBS and incubated with secondary antibody (Alexa fluor 488 [Goat anti mouse]) for an hour followed by nuclear staining using DAPI. For cell area and perimeter measurements, images were acquired and processed using ZEISS™ AXIO fluorescent microscope and AXIOVISION™ software. For sarcomere length, images were acquired and processed using LEICA™ TCS-SPE confocal microscope and LEICA™ software. These confocal images were used to select 1-2 myofibrils per cell with at least ten continuous, well-recognized alpha-actinin bands and divided the length value by the number of sarcomeres. The images were further analyzed using IMAGE J™ software.

Flow Cytometry

Cardiomyocytes were fixed in 4% paraformaldehyde for 10 minutes and labeled using the following primary antibodies—human anti-cTnT PE (R&D SYSTEMS™) and human anti-SMA APC (R&D SYSTEMS™) in 0.75% saponin. These were then incubated with goat-anti-mouse IgG conjugated to phycoerythrin and donkey-anti-rabbit IgG conjugated to allophycocyanin and analyzed using a BD FACSCANTO II (BD BIOSCIENCES™) with FACSDiva software (BD BIOSCIENCES™). Data analysis was performed using FLOWJO™ software (Tree Star, Ashland, Oreg., USA).

mRNA and miRNA Sequencing Analysis

Total RNAs for HFA and HFV samples were extracted using RNAeasy mini kit (QIAGEN™)[7]. Total RNAs for all other samples were extracted with MIRNEASY™ mini kit (QIAGEN™) and were further DNAse treated with DNA-free kit (AMBION™). RNA and Small RNA libraries were prepared independently using TRUSEQ™ library preparation kits (ILLUMINA™) following the manufacturer's protocols. The samples were sequenced on 28-70 million coverage. Sequence data for miRNAs were analyzed using miRDeep2™ software[8]. Raw sequences were first trimmed for any adapter and mapped to hg19 reference genome to produce arf files. These alignments are used to identify expression levels of known and novel miRNAs in sequence data. Differential expression analysis was done using edgeR 3.2.4[9]. For mRNA sequencing analysis, mRNA reads from 1 yr old and 20 day old samples were mapped to hg19 reference genome using STAR version 2.3.010. BAM files produced by STAR were analyzed with Cufflinks version 2.1.1_11 run in de novo mode. Cufflinks output files as well as RefSeq gene models provided by UCSC were merged together using the Cuffmerge utility from the Cufflinks package.

Gene and transcript abundance was estimated using Markov chain Monte Carlo to sample from a hierarchical Bayesian model. The model includes parameters separately capturing transcription and splicing rates at the sample, condition and experiment level. Under this model, estimates from transcripts with very low data are effectively shrunk towards each other to avoid spuriously highfold-change estimates that can occur when using simple read or fragment count estimates. Expression estimates, measured in transcripts per million (TPM), and adjusted using upper quantile normalization[12], were generated for the Ensembl 74 gene annotation database[13].

Separately, statistical significance of differential expression at the gene level was analyzed using DESeq[14]. Both principle component analysis and hierarchical clustering were performed using log-transformed TPM gene expression estimates using R 3.0.2. Hierarchical clustering used Euclidean distance as the metric. Heat map for the RNA sequencing data was generated using the edgeR version 3.2.4[15] available in Bioconductor version 2.8 and for miRNA sequencing, data was generated using the multi experiment viewer[16]. Scatter plots were made using Microsoft Excel. Density plots were generated using R and. Kolmogorov-Smirnov test was used to calculate p-values[17]. The miRNA-mRNA target and pathway analysis was done using IPA software (INGENUITY SYSTEMS™).

Splice Variant Analysis

To define a set of differentially spliced genes, the inventors looked for changes in isoform proportions, defined as an isoform's expression divided by the sum of the expression of all isoforms with the same transcription start site. When considering differential splicing any gene was included with an isoform having posterior probability of at least 0.9 of a net change in proportion of ±0.3 or more between conditions. To increase the chances of detecting changes in splicing dynamics the AceView gene annotations were used, which more liberally include alternate isoforms[18].

miRNA and mRNA qPCR Analysis

Total RNAs were extracted with miRNeasy™ mini kit (QIAGEN™) or using TRIZOL™ (INVITROGEN™). RNA was DNAse treated with DNA-free kit (AMBION™). miR-let-7g and mir-let-7i taqman assays (APPLIED BIOSYSTEMS) were used for miRNAqPCRs following the manufacturer's protocol using RNU66 snoRNA as a loading control. For mRNA qPCR, reverse transcription reaction was carried out using Omniscript™ RT kit (QIAGEN™). Primers for CTNT, MYH7, RYR2, SERCA2 and GJA1 were based on Tulloch et al[2]. Primers for HCN4, KCNJ2, SCN5A, HMGA1, HMGA2, IRS2, INSR, LIN28, SLC27A6 and FABP2, CD36, PPARA, TRIM71, EGR1, CDKN1A were purchased from Real Time Primers. qPCR was performed using SYBR green chemistry and ABI 7300 Real time PCR system. Samples were normalized using GAPDH as a house keeping gene.

Lentiviral Transduction on Cardiomyocytes

For lenti-let-7 OE constructs, Pri-miR-let-7i and pri-miR-let-7g sequence was amplified from H7 genomic DNA using forward primer for let-7i-TCCGCGTGGTCCCGT; reverse primer for let-7i-ATTGTCCTCCGCGGCGC and forward primer for let-7g-AGAGTTCCTCCAGCGCTCC; reverse primer for let-7g-CCCCACTTGGCAGCTGGC, resulting in 153 bp and 154 bp products, respectively. The amplicons were cloned between AgeI and EcoRI sites of pLKO.1 TRC vector (OPEN BIOSYSTEMS™) under human U6 promoter. 293FT cells were plated one day before transfection and pLKO.1-pri-mir-let-7 was co-transfected with packaging vectors (pMK-VSVG, pMDL-G/P-RRE and pRSV-REV) in the presence of 2.5M $CaCl_2$. Medium was changed 24 hours later and the lentiviruses were harvested 48 hours after transfection. Viral transduction of CMs was performed by a spin infection technique. In brief diluted virus in the presence of hexadimethrine bromide (Polybrene, 4 μg/ml)) was added to the beating CMs at day 12 of the directed differentiation protocol. These were then subjected to centrifugation at 3000 RPM for 1 hour followed by overnight incubation with the virus.

Contractile Force Measurement

Arrays of silicone microposts were fabricated out of polydimethylsiloxane (PDMS) via a previously-described double-casting process using soft lithography from a SU8 master[19]. Each micropost within the arrays used for these studies was 6.45 μm in height, 2.3 μm in diameter, and the center to center spacing between adjacent posts was 6 µm. Prior to cell seeding, the tips of these microposts were stamped with 50 µg/ml of mouse laminin (LIFE TECHNOLOGIES™), and the remaining surfaces of the array were fluorescently stained with BSA 594 and blocked with 0.2% Pluronic F-127 (in PBS)[20]. CMs that were 1 week post pLKO-let-7 OE or EV lentiviral transfection, were seeded onto these arrays at a density of around 800,000 cells per substrate.

One week following cell seeding, muscle twitches from individual hESCs-CMs were recorded with high-speed video microscopy within a live cell chamber at 37° C. These images were acquired using a NIKON™ Ti-E upright microscope with a 60× water-immersion objective and a Hammamatsu ORCA™ camera. A custom MATLAB™ code was then used to compare each time frame of this video, to a reference fluorescent image, taken at the base plane of the posts. The twitch force at each post was subsequently calculated by multiplying the deflection of the post by the post's bending stiffness (38 nN/µm). The total twitch force produced by the cell was then determined by adding together the twitch force measured at each post beneath the cell. The average spontaneous beating frequency of the cells was determined by locating the time at which each beat reaches a maximum in the total twitch force (using the same MATLAB™ code), calculating the frequency between each sequential beat: 1/(time at which second beat occurs—time at which first beat occurs), and then averaging these frequencies across all of the measured twitch events.

Mitochondrial Functional Assay

The SEAHORSE™ XF96 extracellular flux analyzer was used to assess mitochondrial function. The plates were pre-treated with 0.1% Gelatin. At around 20 days after differentiation, the cardiomyocytes (both empty vector control and let-7 OE) were seeded onto the plates with a density of 30,000 cells per XF96 well (2,500/mm$^2$) to ensure about 90% surface coverage at the time of experiment. The SEAHORSE™ assays were carried out 3 days after the seeding onto the XF96 well plate. One hour before the assay, culture media were exchanged for base media (unbuffered DMEM (SEAHORSE™ XF Assay Media) supplemented with sodium pyruvate (GIBCO™/INVITROGEN™, 1 mM) and with 25 mM glucose (for MITOSTRESS™ assay), 25 mM glucose with 0.5 mM Carnitine for Palmitate assay. Injection of substrates and inhibitors were applied during the measurements to achieve final concentrations of 4-(trifluoromethoxy)phenylhydrazone at 1 µM (FCCP; SEAHORSE BIOSCIENCES™), oligomycin (2.5 µM), antimycin (2.5 µM) and rotenone (2.5 µM) for MITOSTRESS™ assay; 200 mM palmitate or 33 µM BSA, and 50 µM Etomoxir (ETO) for palmitate assay. The OCR values were further normalized to the number of cells present in each well, quantified by the Hoechst staining (Hoechst 33342; SIGMA-ALDRICH™) as measured using fluorescence at 355 nm excitation and 460 nm emission. Maximal OCR is defined as the change in OCR in response to FCCP compared to OCR after the addition of oligomycin. Cellular capacity to utilize Palmitate as an energy source was calculated as the OCR reduction after ETO addition. The reagents were from SIGMA™, unless otherwise indicated.

REFERENCES FOR EXAMPLE 4

1. Laflamme, M. A. et al. Cardiomyocytes derived from human embryonic stem cells in pro-survival factors enhance function of infarcted rat hearts. *Nat Biotechnol* 25, 1015-1024 (2007).
2. Tulloch, N. L. et al. Growth of engineered human myocardium with mechanical loading and vascular coculture. *Circ Res* 109, 47-59 (2011).
3. Paige, S. L. et al. A temporal chromatin signature in human embryonic stem cells identifies regulators of cardiac development. *Cell* 151, 221-232 (2012).
4. Palpant, N. J. P., L.; Robert, M.; Hadland, B.; Jones, D.; Ruzzon, W. L.; Bernstein, I.; Zheng, Y.; Murry, C. E. Activin A and BMP4 modulation of Wnt/catenin signaling directs fate specification of mesoderm derivatives from human embryonic stem cells. In preparation.
5. Lian, X. et al. Robust cardiomyocyte differentiation from human pluripotent stem cells via temporal modulation of canonical Wnt signaling. *Proceedings of the National Academy of Sciences of the United States of America* 109, E1848-1857 (2012).
6. Paige, S. L. et al. Endogenous Wnt/beta-catenin signaling is required for cardiac differentiation in human embryonic stem cells. *PloS one* 5, e11134 (2010).
7. Chong, J. J. et al. Progenitor cells identified by PDGFR-alpha expression in the developing and diseased human heart. *Stem cells and development* 22, 1932-1943 (2013).
8. Mackowiak, S. D. Identification of novel and known miRNAs in deep-sequencing data with miRDeep2. *Curr Protoc Bioinformatics* Chapter 12, Unit 12 10 (2011).
9. Robinson, M. D., McCarthy, D. J. & Smyth, G. K. edgeR: a Bioconductor package for differential expression analysis of digital gene expression data. *Bioinformatics* 26, 139-140 (2010).
10. Dobin, A. et al. STAR: ultrafast universal RNA-seq aligner. *Bioinformatics* 29, 15-21 (2013).
11. Roberts, A., Pimentel, H., Trapnell, C. & Pachter, L. Identification of novel transcripts in annotated genomes using RNA-Seq. *Bioinformatics* 27, 2325-2329 (2011).
12. Bullard, J. H., Purdom, E., Hansen, K. D. & Dudoit, S. Evaluation of statistical methods for normalization and differential expression in mRNA-Seq experiments. *BMC bioinformatics* 11, 94 (2010).
13. Flicek, P. et al. Ensembl 2014. *Nucleic acids research* 42, D749-755 (2014).
14. Anders, S. & Huber, W. Differential expression analysis for sequence count data. *Genome biology* 11, R106 (2010).
15. McCall, M. N. et al. MicroRNA profiling of diverse endothelial cell types. *BMC medical genomics* 4, 78 (2011).
16. Saeed, A. I. et al. TM4: a free, open-source system for microarray data management and analysis. *BioTechniques* 34, 374-378 (2003).
17. Wang, C., Dostanic, S., Servant, N. & Chalifour, L. E. Egr-1 negatively regulates expression of the sodium-calcium exchanger-1 in cardiomyocytes in vitro and in vivo. *Cardiovasc Res* 65, 187-194 (2005).
18. Thierry-Mieg, D. & Thierry-Mieg, J. AceView: a comprehensive cDNA-supported gene and transcripts annotation. *Genome biology* 7 Suppl 1, S12 11-14 (2006).
19. Tan, J. L. et al. Cells lying on a bed of microneedles: an approach to isolate mechanical force. *Proceedings of the National Academy of Sciences of the United States of America* 100, 1484-1489 (2003).
20. Sniadecki, N. J. & Chen, C. S. Microfabricated silicone elastomeric post arrays for measuring traction forces of adherent cells. *Methods Cell Biol* 83, 313-328 (2007).

The invention claimed is:

1. A method for inducing maturation of a cultured cardiomyocyte comprising contacting in vitro a cultured cardiomyocyte derived from a pluripotent stem cell or an induced pluripotent stem cell (iPS cell) with an isolated microRNA from the let-7 family, or with a vector that expresses said miRNA of the let-7 family, thereby inducing maturation of the cultured cardiomyocyte.

2. The method of claim 1, wherein the miRNA from the let-7 family is selected from the group consisting of: let-7a-1, let-7a-2, let-7b, let-7c, let-7d, let-7e, let-7f-1, let-7f-2, let-7g, and let-7i.

3. The method of claim 2, wherein the miRNA is let-7g or let-7i.

4. The method of claim 1, wherein the miRNA from the let-7 family is resistant to inhibition by Lin28.

5. The method of claim 1, wherein the cardiomyocyte expresses the fetal isoform of myosin heavy chain (MHC), troponin 1, or carnitine palmitoyl transferase 1 (CPT-1) prior to contacting with the miRNA.

6. The method of claim 1, wherein the maturation of the cardiomyocyte comprises a shift in the primary source of energy from glycolysis to fatty acid oxidation.

7. The method of claim 1, wherein the resulting mature cardiomyocyte expresses at least one of: cardiac troponin (cTnT), myosin heavy chain-7 (MYH7), sacrcoendoplasmic reticulum ATPAse (SERCA2a), gap junction protein alpha 1 (GJA1), or ryanodine receptor 2 (RYR2).

8. The method of claim 1, further comprising a step of administering the resulting mature cardiomyocyte to a subject in need thereof, wherein the subject has cardiac tissue damage as a result of an acute myocardial infarction, ischemia/reperfusion injury, autophagy, cardiomyopathy, dilated cardiomyopathy, heart failure, restenosis, apoptosis, or necrosis.

9. The method of claim 1, wherein the cultured cardiomyocyte is a human cardiomyocyte.

* * * * *